(12) United States Patent
Sasaki et al.

(10) Patent No.: US 6,337,306 B1
(45) Date of Patent: Jan. 8, 2002

(54) PHENOXYACETIC ACID DERIVATIVES AND THEIR USE AS HERBICIDES

(75) Inventors: Norio Sasaki; Atsushi Go, both of Ibaraki-ken; Hideshi Mukaida, Ibaraki; Yukiko Oe, Ibaraki-ken, all of (JP)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/367,043

(22) PCT Filed: Jan. 30, 1998

(86) PCT No.: PCT/EP98/00501

§ 371 Date: Nov. 5, 1999

§ 102(e) Date: Nov. 5, 1999

(87) PCT Pub. No.: WO98/34898

PCT Pub. Date: Aug. 13, 1998

(30) Foreign Application Priority Data

Feb. 6, 1997 (JP) .................................................. 9-24117

(51) Int. Cl.[7] ...................... A01N 39/02; A01N 41/10; C07C 69/736; C07C 251/54; C07C 257/04

(52) U.S. Cl. .............................. 504/314; 560/9; 560/11; 560/35; 560/60; 560/61; 560/62; 562/426; 562/429; 562/440; 562/470; 562/471; 562/472; 562/624; 504/240; 504/242; 504/244; 504/254; 504/260; 504/289; 504/291; 504/323; 504/310; 504/313; 504/315; 504/317; 504/321; 504/322; 544/321; 544/332; 546/300; 546/312; 546/335; 549/68; 549/77; 549/496; 549/480; 558/7; 558/414

(58) Field of Search .......................... 558/7, 414; 560/9, 560/11, 35, 60, 61, 62; 562/426, 429, 440, 470, 471, 472, 624; 504/310, 314, 315, 317, 321, 322, 323, 313

(56) References Cited

FOREIGN PATENT DOCUMENTS

| EP | 0212859 | 3/1987 |
|----|---------|--------|
| WO | 96/32399 | 10/1996 |
| WO | 98/03464 | 1/1998 |

*Primary Examiner*—Richard L. Raymond
(74) *Attorney, Agent, or Firm*—Burns, Doane, Swecker & Mathis, L.L.P.

(57) ABSTRACT

Phenoxyacetic acid derivatives of the formula:

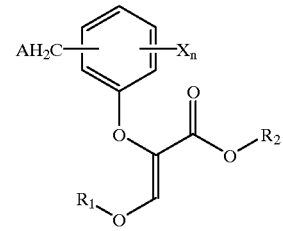

wherein $R_1$, $R_2$, $X_n$ and A are as defined herein, and a process for preparing the derivatives. The derivatives are used as herbicides.

16 Claims, No Drawings

PHENOXYACETIC ACID DERIVATIVES AND THEIR USE AS HERBICIDES

REFERENCE TO RELATED APPLICATION

The present application is a 371 of PCT/EP98/00501 filed Jan. 30, 1998.

FIELD OF THE INVENTION

This invention relates to novel phenoxyacetic acid derivatives, compositions containing them, processes and intermediates for their preparation, and their use as herbicides.

BACKGROUND ART

Japanese Patent Publication No. Sho 62-48649 discloses the preparation and fungicidal or plant growth regulator activity for the following acrylic acid ester derivatives, stereoisomers thereof, and metal complexes of general formula:

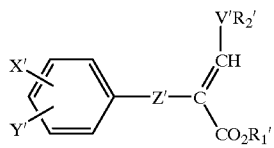

wherein, V' represents an oxygen or sulfur atom; X' and Y', may be the same or different selected from a hydrogen or halogen atom, optionally substituted alkyl, optionally substituted alkenyl, optionally substituted aryl, optionally substituted heteroring, optionally substituted alkynyl, haloalkyl, alkoxy, optionally substituted haloalkoxy, optionally substituted arylalkoxy, optionally substituted acyloxy, optionally substituted amino, acylamino, nitro, nitrile, —$CO_2R_3'$, —$CONR_4'R_5'$, or —$COR_6'$ group, or X' and Y' being at the adjacent position on a phenyl ring, may form an aromatic condensed ring or an aliphatic condensed ring optionally containing one or more hetero atoms; Z' represents optionally substituted methylene, optionally substituted amino, oxygen or sulphur and when Z' is a substituted methylene group, the substituent may join the 2-position of the phenyl ring to form a non-aromatic fused ring; $R_1'$ and $R_2'$ each independently represent an alkyl group having from one to four carbon atoms optionally substituted by one or more halogen atoms; $R_3'$, $R_4'$, $R_5'$ and $R_6'$ are the same or different groups selected from a hydrogen atom, optionally substituted alkyl, cycloalkyl, alkenyl, alkynyl, optionally substituted aryl, optionally substituted aralkyl and cycloalkyl. However it has not been disclosed or suggested that any 3-alkoxy-2-phenoxyacrylate derivatives having a substituted alkyl substituent(in particular a haloalkyl or hydroxyalkyl substituent) on the benzene ring possess useful herbicidal properties.

OBJECTS OF THE INVENTION

It is an object of the invention to provide new phenoxyacetic acid derivatives useful as herbicides, and processes for their preparation.

A second object of the invention is to provide herbicidal compositions and herbicidal methods of use for herbicidal phenoxyacetic acid derivatives.

A third object of the invention is to provide phenoxyacetic acid derivatives which possess selective herbicidal activity.

A fourth object of the invention is to provide phenoxyacetic acid derivatives effective as low dose herbicides.

A fifth object of the invention is to provide phenoxyacetic acid derivatives which possess good residual activity.

These and other objects of the invention can be achieved in whole or in part.

DESCRIPTION OF THE INVENTION

The present invention provides phenoxyacetic acid derivatives of formula

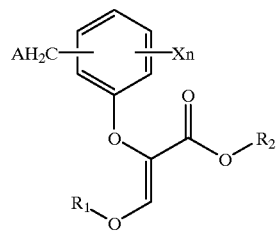

(I)

wherein:

$R_1$ and $R_2$ each represents independently a hydrogen atom, optionally substituted lower alkyl, optionally substituted lower alkenyl, optionally substituted lower alkynyl, optionally substituted cycloalkyl or —$C_mH_{2m}$ (optionally substituted phenyl);

X represents a halogen atom, cyano, lower alkoxycarbonyl, lower alkyl, lower alkenyl, lower alkynyl, cycloalkyl, lower alkoxy, lower alkylthio, lower alkylsulphinyl, lower alkylsulfonyl, lower haloalkoxycarbonyl, lower haloalkyl, lower haloalkenyl, lower haloalkynyl, halocycloalkyl, lower haloalkoxy, lower haloalkylthio, lower haloalkylsulphinyl, lower haloalkylsulfonyl, nitro, amino, lower alkylamino, lower dialkylamino, optionally substituted phenoxy, lower alkylcarbonylamino, carbamoyl, lower alkylcarbamoyl, lower dialkylcarbamoyl or SF5;

n and m represent 0, 1 or 2;

A represents halogen atom, hydroxy, or A' wherein A' represents $OR_3$, $S(O)_KR_3$; or represents a formula II:

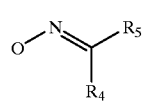

A-1

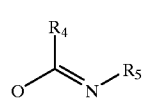

A-2

$R_3$ represents optionally substituted lower alkyl, optionally substituted lower alkenyl, optionally substituted lower alkynyl, optionally substituted cycloalkyl, optionally substituted phenyl, optionally substituted heteroaryl, optionally substituted lower alkylcarbonyl, optionally substituted lower alkenylcarbonyl, optionally substituted lower alkynylcarbonyl, optionally substituted cycloalkylcarbonyl, optionally substituted phenylcarbonyl, optionally substituted heteroarylcarbonyl, optionally substituted cycloalkenyl, optionally substituted cycloalkenylcarbonyl, —$C_pH_{2p}$ (optionally substituted phenyl), —$C_qH_{2q}$ (optionally substituted heteroaryl), —($C_rH_{2r}$) $CO_2$alkyl, —($C_sH_{2s}$) cycloalkyl, —CO($C_tH_{2t}$)Y, —($C_uH_{2u}$) $COCH_2$ (optionally substituted phenyl), —($C_fH2_f$) O (optionally substituted phenyl), —($C_gH_{2g}$) S (optionally substituted phenyl), or —($C_jH_{2j}$) O ($C_zH_{2z}$) (optionally substituted phenyl);

k represents zero, one or two;

f, g, j, z, p, q, r, s, t and u represent one or two;

Y represents optionally substituted phenyl, optionally substituted phenoxy, optionally substituted heteroaryl, optionally substituted phenylthio, alkoxy or optionally substituted heteroaryloxy;

$R_4$ represents a hydrogen atom, cyano, optionally substituted lower alkyl, optionally substituted lower alkenyl, optionally substituted lower alkynyl, optionally substituted cycloalkyl, optionally substituted phenyl, or optionally substituted heteroaryl;

$R_5$ represents optionally substituted lower alkyl, optionally substituted lower alkenyl, optionally substituted lower alkynyl, optionally substituted cycloalkyl, optionally substituted phenyl, optionally substituted lower alkoxy, optionally substituted lower alkenyloxy, optionally substituted lower alkynyloxy, optionally substituted cycloalkyloxy, optionally substituted heteroaryloxy, optionally substituted cycloalkenyloxy, , optionally substituted heteroaryl, —$C_vH_{2v}$ (optionally substituted phenyl), —$OC_wH_{2w}$ (optionally substituted phenyl), —($C_xH_{2x}$) O (optionally substituted phenyl), optionally substituted lower alkylthio, optionally substituted phenylthio, —$SC_yH_{2y}$ (optionally substituted phenyl) or optionally substituted phenoxy;

v, w, x and y represent one or two;

a geometric isomer thereof;

and agriculturally acceptable salts thereof, which possess valuable herbicidal properties.

In the phenoxyacetic acid derivatives of the present invention, there are two different stereoisomers, syn and anti [in other words, cis (Z), and trans (E) isomers] at a double bond. It will be understood that the present invention embraces both the pure isomers and mixtures thereof.

In certain cases the substituents $R_1$, $R_2$, $R_3$, $R_4$, $R_5$, A and X contribute to optical isomerism and/or stereo isomerism. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable salts with bases, include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula I containing an amino group, include salts with inorganic acids, for example hydrochlorides, sulphates, phosphates and nitrates and salts with organic acids for example acetic acid.

It is understood that in the above definitions used in formula (I) all of the optionally substituted groups may have as the optional substituent one or more halogen atoms.

It is also understood that for optionally substituted cycloalkyl, optionally substituted cycloalkenyl and for other optionally substituted groups which incorporate cycloalkyl or cycloalkenyl portions, the optional substituent may be selected from lower alkyl, lower alkenyl, lower alkynyl, lower haloalkyl and halogen.

It is also understood that for optionally substituted phenyl, optionally substituted heteroaryl, optionally substituted phenoxy, optionally substituted phenylthio, optionally substituted phenylcarbonyl, optionally substituted heteroarylcarbonyl, optionally substituted heteroaryloxy, and other optionally substituted groups which incorporate phenyl or heteroaryl portions, that the optional substituent is selected from halogen, phenoxy, lower alkyl, lower haloalkyl, cyano, lower alkoxycarbonyl, lower haloalkoxycarbonyl, lower alkoxy, lower haloalkoxy, lower alkylthio, lower haloalkylthio, lower alkylsulfinyl, lower haloalkylsulfinyl, lower alkylsulfonyl, lower haloalkylsulfonyl, nitro, alkylcarbonyl, lower alkylamino, lower dialkylamino, carbamoyl, lower alkylcarbamoyl, lower dialkylcarbamoyl and lower alkylcarbonylamino.

In the present invention, some embodiments of A, A', $R_2$, $R_3$, $R_4$, $R_5$, and X defined previously will be explained more precisely as follows.

Halogen atom means fluorine, chlorine, bromine or iodine.

Lower alkyl means a straight- or branched-chain alkyl group having from one to six carbon atoms such as methyl, ethyl, n-propyl, isopropyl, n-butyl, isobutyl, sec-butyl, tert-butyl, n-pentyl, neopentyl, tert-pentyl or hexyl.

Lower alkenyl means a straight- or branched-alkenyl group having from two to six carbon atoms, such as ethenyl, propenyl, butenyl or pentenyl.

Lower alkynyl means a straight- or branched-chain alkynyl group having from two to six carbon atoms, such as ethynyl, propynyl, butynyl, pentynyl or hexynyl.

Cycloalkyl groups have from three to six carbon atoms, such as cyclopropyl, cyclobutyl, cyclopentyl or cyclohexyl.

Cycloalkenyl groups have five or six carbon atoms namely cyclopentenyl or cyclohexenyl.

Lower alkoxy groups contain from one to six carbon atoms such as methoxy, ethoxy, propoxy, isopropoxy, butoxy or pentoxy.

Lower alkenyloxy groups have from two to six carbon atoms, such as ethenyloxy, propenyloxy, butenyloxy or pentenyloxy.

Lower alkynyloxy groups have from two to six carbon atoms, such as ethynyloxy, propynyloxy, butynyloxy, pentynyloxy or hexynyloxy.

Cycloalkyloxy groups have from three to six carbon atoms, such as cyclopropyloxy, cyclobutyloxy, cyclopentyloxy or cyclohexyloxy.

Cycloalkenyloxy groups have five or six carbon atoms, namely cyclopentenyloxy or cyclohexenyloxy.

Lower alkylthio groups contain from one to six carbon atoms, for example methylthio, ethylthio, propylthio, isopropylthio, butylthio or pentylthio.

Lower alkylsulphinyl groups have from one to six carbon atoms, for example methylsulphinyl, ethylsulphinyl, propylsulphinyl, isopropylsulphinyl, butylsulphinyl or pentylsulphinyl.

Lower alkylsulfonyl groups have from one to six carbon atoms, for example methylsulfonyl, ethylsulfonyl, propylsulfonyl, isopropylsulfonyl, butylsulfonyl or pentylsulfonyl.

Lower alkylcarbonyl groups contain from one to six carbon atoms in the alkyl portion, such as methylcarbonyl, ethylcarbonyl, propylcarbonyl, isopropylcarbonyl, butylcarbonyl or pentylcarbonyl.

Lower alkenylcarbonyl groups contain from two to six carbon atoms in the alkenyl portion; for example, ethenylcarbonyl, propenylcarbonyl, butenylcarbonyl or pentenylcarbonyl.

Lower alkynylcarbonyl groups contain from two to six carbon atoms in the alkynyl portion, for example, ethynylcarbonyl, propynylcarbonyl, butynylcarbonyl, pentynylcarbonyl or hexynylcarbonyl.

Cycloalkylcarbonyl groups contain from three to six carbon atoms in the cycloalkyl portion, for example, cyclopropylcarbonyl, cyclobutylcarbonyl, cyclopentylcarbonyl or cyclohexylcarbonyl.

Cycloalkenylcarbonyl groups contain five or six carbon atoms in the cycloalkenyl portion, namely cyclopentenylcarbonyl or cyclohexenylcarbonyl.

Lower haloalkyl groups contain from one to six carbon atoms, such as bromomethyl, difluoromethyl, dichloromethyl, trifluoromethyl, 1-chloroethyl, 2-iodoethyl, 3-chloropropyl, 2-methyl-2-chloropropyl or 2,2,2-trifluoroethyl.

Lower haloalkoxy groups contain from one to six carbon atoms, for example, trifluoromethoxy, difluoromethoxy, chlorodifluoromethoxy, 2-chloroethoxy, 1,1,2,2-tetrafluoroethoxy or 3-chloropropoxy.

Lower haloalkylthio groups contain from one to six carbon atoms, for example trifluoromethylthio, difluoromethylthio, chlorodifluoromethylthio, 2-chloroethylthio, 1,1,2,2-tetrafluoroethylthio or 3-chloropropylthio.

Lower haloalkylsulphinyl groups contain from one to six carbon atoms, for example, trifluoromethylsulphinyl, difluoromethylsulphinyl, chlorodifluoromethylsulphinyl, 2-chloroethylsulphinyl, 1,1,2,2-tetrafluoroethylsulphinyl or 3-chloropropylsulphinyl.

Lower haloalkylsulfonyl groups contain from one to six carbon atoms, for example, trifluoromethylsulfonyl, difluoromethylsulfonyl, chlorodifluoromethylsulfonyl, 2-chloroethylsulfonyl, 1,1,2,2-tetrafluoroethylsulfonyl or 3-chloropropylsulfonyl.

Lower alkoxycarbonyl groups contain from one to six carbon atoms in the alkoxy portion, for example, methoxycarbonyl, ethoxycarbonyl or isopropylcarbonyl.

Lower haloalkoxycarbonyl groups contain from one to six carbon atoms in the alkoxy portion, for example, trifluoromethoxycarbonyl, difluoromethoxycarbonyl, chlorodifluoromethoxycarbonyl, 2-chloroethoxycarbonyl, 1,1,2,2-tetrafluoroethoxycarbonyl or 3-chloropropoxycarbonyl.

Heteroaryl groups comprise a five or six membered aromatic heterocyclic ring containing from one to three hetero atoms selected from oxygen, nitrogen and sulphur, for example, furanyl, thienyl, pyrrolyl, pyrazolyl, imidazolyl, thiazolyl, pyridyl, pyrimidyl or pyridazinyl.

Heteroaryloxy groups comprise as the heteroaryl portion a five or six membered heterocyclic ring containing from one to three hetero atoms selected from oxygen, nitrogen and sulphur, for example, furanyloxy, thienyloxy, pyrrolyloxy, pyrazolyloxy, imidazolyloxy, thiazolyloxy, pyridyloxy, pyrimidyloxy or pyridazinyloxy.

Heteroarylthio groups comprise as the heteroaryl portion a five or six membered heterocyclic ring containing from one to three hetero atoms selected from oxygen, nitrogen and sulphur, for example, furanylthio, thienylthio, pyrrolylthio, pyrazolylthio, imidazolylthio, thiazolylthio, pyridylthio, pyrimidylthio or pyridazinylthio.

In addition, any group not cited above can be obtained by combination of the above atoms or groups, or by selecting from atoms or groups known per se.

Compounds of formula (I) above in which the group $CH_2A$ is located at the ortho position of the phenyl ring are preferred.

Compounds of formula (I) above in which $R_1$ and $R_2$ represent lower alkyl are preferred (preferably $R_1$ and $R_2$ represent methyl).

Compounds of formula (I) above in which X represents halogen are preferred (compounds wherein X is chlorine are especially preferred).

Compounds of formula (I) above in which A represents a group selected from halogen; hydroxy; A-1 wherein $R_4$ represents lower alkyl and $R_5$ represents —$OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl; A-2 wherein $R_4$ represents lower alkyl and $R_5$ represents —$OCH_2$ (optionally substituted phenyl); and $SR_3$ wherein $R_3$ represents optionally substituted phenyl, $CH_2$ (optionally substituted phenyl), lower alkyl or cycloalkyl, are preferred (compounds in which A represents halogen or hydroxy are especially preferred).

Preferably the compounds of formula (I) are Z isomers at the double bond which is substituted by $OR_1$.

A preferred class of compounds of formula (I) are those wherein:

$R_1$ and $R_2$ represent lower alkyl;

the group $CH_2A$ is located at the ortho position of the phenyl ring; and

A represents a group selected from halogen; hydroxy; A-1 wherein $R_4$ represents lower alkyl and $R_5$ represents —$OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl; A-2 wherein $R_4$ represents lower alkyl and $R_5$ represents —$OCH_2$ (optionally substituted phenyl); and $SR_3$ wherein $R_3$ represents optionally substituted phenyl, —$CH_2$ (optionally substituted phenyl), lower alkyl or cycloalkyl.

A further preferred class of compounds of formula (I) are those wherein:

$R_1$ and $R_2$ represent lower alkyl;

X represents halogen; and $CH_2A$ is located at the ortho position of the phenyl ring and A represents a group selected from halogen; hydroxy; A-1 wherein $R_4$ represents lower alkyl and $R_5$ represents —$OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl;

A-2 wherein $R_4$ represents lower alkyl and $R_5$ represents —$OCH_2$ (optionally substituted phenyl); and $SR_3$ wherein $R_3$ represents optionally substituted phenyl, —$CH_2$ (optionally substituted phenyl), lower alkyl or cycloalkyl.

A further preferred class of compounds of formula (I) are those wherein:

$R_1$ and $R_2$ represent lower alkyl;

X represents halogen;

$CH_2A$ is located at the ortho position of the phenyl ring; and

A represents a group selected from halogen; hydroxy; A-1 wherein $R_4$ represents lower alkyl and $R_5$ represents —$OCH_2$ (optionally substituted phenyl), optionally substituted phenoxy or lower alkyl; $OR_3$ wherein $R_3$ represents optionally substituted phenyl, lower alkylcarbonyl or lower alkyl; and A-2 where $R_4$ represents lower alkyl and $R_5$ represents —$OCH_2$ (optionally substituted phenyl).

The following compounds also form part of the invention. In the Tables 1-1, 1-2 and 1-3 it will be understood that Me means methyl; Et means ethyl; n-Pr means n-propyl; i-Pr means isopropyl; c-Pr means cyclopropyl; n-Bu means n-butyl; s-Bu means sec-butyl; i-Bu means isobutyl; t-Bu means tert-butyl; c-Bu means cyclobutyl; c-Pen means cyclopentyl; n-Hex means n-hexyl; c-Hex means cyclohexyl; Ph means phenyl; Bn means benzyl; CHCCH2 means prop-2-ynyl and CHCCH2CO means but-3-yn-1-oyl. Also where numbers appear directly after atoms or groups they are understood to be subscripts (e.g. CO2Me means $CO_2Me$, CF3 means $CF_3$ etc.).

Tables 1-1, 1-2 and 1-3 contain a total of five sets of compounds identified as follows:

Table 1-1 contains a set of 404 compounds having compound numbers from 1.1 to 1.404.

Table 1-2 contains two sets of compounds, the first set comprising of 727 compounds wherein A' represents OR3 and having compound numbers from 2.1 to 2.727. The second set comprising of a further 727 compounds wherein A' represents SR3 and having compound numbers from 3.1 to 3.727.

Table 1-3 contains two sets of compounds, the first set comprising of 720 compounds wherein A' represents A-1 and having compound numbers from 4.1 to 4.720. The second set comprising of a further 720 compounds wherein A' represents A-2 and having compound numbers from 5.1 to 5.720. Furthermore it is understood that the compounds in the following tables may represent either the Z or the E isomers at the double bond of formula (I) which is substituted by the OR1 group, or represents a mixture of both isomers.

TABLE 1-1

| No. | ACH2 | Xn | R1 | R2 |
|---|---|---|---|---|
| 1 | 2-ClCH2 | H | Me | Me |
| 2 | 2-ClCH2 | H | Me | Et |
| 3 | 2-ClCH2 | H | Me | n-Pr |
| 4 | 2-ClCH2 | H | Me | i-Pr |
| 5 | 2-ClCH2 | H | Me | n-Bu |
| 6 | 2-ClCH2 | H | Me | s-Bu |
| 7 | 2-ClCH2 | H | Me | i-Bu |
| 8 | 2-ClCH2 | H | Me | t-Bu |
| 9 | 2-ClCH2 | H | Me | c-Pr |
| 10 | 2-ClCH2 | H | Me | c-Bu |
| 11 | 2-ClCH2 | H | Me | n-Pen |
| 12 | 2-ClCH2 | H | Me | c-Pen |
| 13 | 2-ClCH2 | H | Me | n-Hex |
| 14 | 2-ClCH2 | H | Me | c-Hex |
| 15 | 2-ClCH2 | H | Me | Bn |
| 16 | 2-ClCH2 | H | Me | CH(Me)Ph |
| 17 | 2-ClCH2 | H | Me | CH2CH2Ph |
| 18 | 2-ClCH2 | H | Me | CH2CH=CH2 |
| 19 | 2-ClCH2 | H | Me | CH2(4-Cl—C6H4) |
| 20 | 2-ClCH2 | H | Me | CH2(2-Cl—C6H4) |
| 21 | 2-ClCH2 | H | Et | Me |
| 22 | 2-ClCH2 | H | Et | Et |
| 23 | 2-ClCH2 | H | Et | i-Pr |
| 24 | 2-ClCH2 | H | Et | c-Pr |
| 25 | 2-ClCH2 | H | i-Pr | Me |
| 26 | 2-ClCH2 | H | i-Pr | i-Pr |
| 27 | 2-ClCH2 | H | CH2CH=CH2 | Me |
| 28 | 2-ClCH2 | H | CH2CH=CH2 | CH2CH=CH2 |
| 29 | 2-ClCH2 | H | Bn | Me |
| 30 | 2-ClCH2 | H | Bn | Bn |
| 31 | 2-BrCH2 | H | Me | Me |
| 32 | 2-BrCH2 | H | Me | Et |
| 33 | 2-BrCH2 | H | Me | n-Pr |
| 34 | 2-BrCH2 | H | Me | i-Pr |
| 35 | 2-BrCH2 | H | Me | n-Bu |
| 36 | 2-BrCH2 | H | Me | s-Bu |
| 37 | 2-BrCH2 | H | Me | i-Bu |
| 38 | 2-BrCH2 | H | Me | t-Bu |

TABLE 1-1-continued

| No. | ACH2 | Xn | R1 | R2 |
|---|---|---|---|---|
| 39 | 2-BrCH2 | H | Ne | c-Pr |
| 40 | 2-BrCH2 | H | Me | c-Bu |
| 41 | 2-BrCH2 | H | Me | n-Pen |
| 42 | 2-BrCH2 | H | Me | c-Pen |
| 43 | 2-BrCH2 | H | Me | n-Hex |
| 44 | 2-BrCH2 | H | Me | c-Hex |
| 45 | 2-BrCH2 | H | Me | Bn |
| 46 | 2-BrCH2 | H | Me | CH(Me)Ph |
| 47 | 2-BrCH2 | H | Me | CH2CH2Ph |
| 48 | 2-BrCH2 | H | Me | CH2CH=CH2 |
| 49 | 2-BrCH2 | H | Me | CH2(4-Cl—C6H4) |
| 50 | 2-BrCH2 | H | Me | CH2(2-Cl—C6H4) |
| 51 | 2-BrCH2 | H | Et | Me |
| 52 | 2-BrCH2 | H | Et | Et |
| 53 | 2-BrCH2 | H | Et | i-Pr |
| 54 | 2-BrCH2 | H | Et | c-Pr |
| 55 | 2-BrCH2 | H | i-Pr | Me |
| 56 | 2-BrCH2 | H | i-Pr | i-Pr |
| 57 | 2-BrCH2 | H | CH2CH=CH2 | Me |
| 58 | 2-BrCH2 | H | CH2CH=CH2 | CH2CH=CH2 |
| 59 | 2-BrCH2 | H | Bn | Me |
| 60 | 2-BrCH2 | H | Bn | Bn |
| 61 | 2-BrCH2 | 3-Cl | Me | Me |
| 62 | 2-BrCH2 | 3-Cl | Me | Et |
| 63 | 2-BrCH2 | 3-Cl | Me | i-Pr |
| 64 | 2-BrCH2 | 3-Cl | Me | c-Pr |
| 65 | 2-BrCH2 | 3-Cl | Et | Me |
| 66 | 2-BrCH2 | 3-Cl | Et | Et |
| 67 | 2-BrCH2 | 3-Cl | Me | Me |
| 68 | 2-BrCH2 | 3-Cl | Me | Et |
| 69 | 2-BrCH2 | 3-Cl | Me | i-Pr |
| 70 | 2-BrCH2 | 3-Cl | Me | c-Pr |
| 71 | 2-BrCH2 | 3-Cl | Et | Me |
| 72 | 2-BrCH2 | 3-Cl | Et | Et |
| 73 | 2-BrCH2 | 4-Cl | Me | Me |
| 74 | 2-BrCH2 | 4-Cl | Me | Et |
| 75 | 2-BrCH2 | 4-Cl | Me | i-Pr |
| 76 | 2-BrCH2 | 4-Cl | Me | c-Pr |
| 77 | 2-BrCH2 | 4-Cl | Et | Me |
| 78 | 2-BrCH2 | 4-Cl | Et | Et |
| 79 | 2-BrCH2 | 5-Cl | Me | Me |
| 80 | 2-BrCH2 | 5-Cl | Me | Et |
| 81 | 2-BrCH2 | 5-Cl | Me | i-Pr |
| 82 | 2-BrCH2 | 5-Cl | Me | c-Fr |
| 83 | 2-BrCH2 | 5-Cl | Et | Me |
| 84 | 2-BrCH2 | 5-Cl | Et | Et |
| 85 | 2-BrCH2 | 6-Cl | Me | Me |
| 86 | 2-BrCH2 | 6-Cl | Me | Et |
| 87 | 2-BrCH2 | 6-Cl | Me | i-Pr |
| 88 | 2-BrCH2 | 6-Cl | Me | c-Pr |
| 89 | 2-BrCH2 | 6-Cl | Et | Me |
| 90 | 2-BrCH2 | 6-Cl | Et | Et |
| 91 | 2-ClCH2 | 3-Cl | Me | Me |
| 92 | 2-ClCH2 | 3-Cl | Me | Et |
| 93 | 2-ClCH2 | 3-Cl | Me | i-Pr |
| 94 | 2-ClCH2 | 3-Cl | Me | c-Pr |
| 95 | 2-ClCH2 | 3-Cl | Et | Me |
| 96 | 2-ClCH2 | 3-Cl | Et | Et |
| 97 | 2-ClCH2 | 3-Cl | Me | Me |
| 98 | 2-ClCH2 | 3-Cl | Me | Et |
| 99 | 2-ClCH2 | 3-Cl | Me | i-Pr |
| 100 | 2-ClCH2 | 3-Cl | Me | c-Pr |
| 101 | 2-ClCH2 | 3-Cl | Et | Me |
| 102 | 2-ClCH2 | 3-Cl | Et | Et |
| 103 | 2-ClCH2 | 4-Cl | Me | Me |
| 104 | 2-ClCH2 | 4-Cl | Me | Et |
| 105 | 2-ClCH2 | 4-Cl | Me | i-Pr |
| 106 | 2-ClCH2 | 4-Cl | Me | c-Pr |
| 107 | 2-ClCH2 | 4-Cl | Et | Me |
| 108 | 2-ClCH2 | 4-Cl | Et | Et |
| 109 | 2-ClCH2 | 5-Cl | Me | Me |
| 110 | 2-ClCH2 | 5-Cl | Me | Et |
| 111 | 2-ClCH2 | 5-Cl | Me | i-Pr |
| 112 | 2-ClCH2 | 5-Cl | Me | c-Pr |
| 113 | 2-ClCH2 | 5-Cl | Et | Me |
| 114 | 2-ClCH2 | 5-Cl | Et | Et |
| 115 | 2-ClCH2 | 6-Cl | Me | Me |

TABLE 1-1-continued

| No. | ACH2 | Xn | R1 | R2 |
|---|---|---|---|---|
| 116 | 2-ClCH2 | 6-Cl | Me | Et |
| 117 | 2-ClCH2 | 6-Cl | Me | i-Pr |
| 118 | 2-ClCH2 | 6-Cl | Me | c-Pr |
| 119 | 2-ClCH2 | 6-Cl | Et | Me |
| 120 | 2-ClCH2 | 6-Cl | Et | Et |
| 121 | 2-ClCH2 | 3-OMe | Me | Me |
| 122 | 2-ClCH2 | 3-OMe | Et | Et |
| 123 | 2-ClCH2 | 4-OMe | Me | Me |
| 124 | 2-ClCH2 | 4-OMe | Et | Et |
| 125 | 2-ClCH2 | 5-OMe | Me | Me |
| 126 | 2-ClCH2 | 5-OMe | Et | Et |
| 127 | 2-ClCH2 | 6-OMe | Me | Me |
| 128 | 2-ClCH2 | 6-OMe | Et | Et |
| 129 | 2-ClCH2 | 3-OCF3 | Me | Me |
| 130 | 2-ClCH2 | 3-OCF3 | Et | Et |
| 131 | 2-ClCH2 | 4-CO2Me | Me | Me |
| 132 | 2-ClCH2 | 4-CO2Me | Et | Et |
| 133 | 2-ClCH2 | 4-SMe | Me | Me |
| 134 | 2-ClCH2 | 4-SMe | Et | Et |
| 135 | 2-ClCH2 | 4-NO2 | Me | Me |
| 136 | 2-ClCH2 | 4-NO2 | Et | Et |
| 137 | 2-ClCH2 | 4-CF3 | Me | Me |
| 138 | 2-ClCH2 | 4-CF3 | Et | Et |
| 139 | 2-ClCH2 | 4-SOMe | Me | Me |
| 140 | 2-ClCH2 | 4-SOMe | Et | Et |
| 141 | 2-ClCH2 | 4-SO2Me | Me | Me |
| 142 | 2-ClCH2 | 4-SO2Me | Et | Et |
| 143 | 2-ClCH2 | 4,6-Cl2 | Me | Me |
| 144 | 2-ClCH2 | 4,6-Cl2 | Et | Et |
| 145 | 2-ClCH2 | 4-Me-6-Cl | Me | Me |
| 146 | 2-ClCH2 | 4-Me-6-Cl | Et | Et |
| 147 | 2-ClCH2 | 4-OMe-6-Cl | Me | Me |
| 148 | 2-ClCH2 | 4-OMe-6-Cl | Et | Et |
| 149 | 2-ClCH2 | 4,6-(NO2)2 | Me | Me |
| 150 | 2-ClCH2 | 4,6-(NO2)2 | Et | Et |
| 151 | 2-BrCH2 | 3-OMe | Me | Me |
| 152 | 2-BrCH2 | 3-OMe | Et | Et |
| 153 | 2-BrCH2 | 4-OMe | Me | Me |
| 154 | 2-BrCH2 | 4-OMe | Et | Et |
| 155 | 2-BrCH2 | 5-OMe | Me | Me |
| 156 | 2-BrCH2 | 5-OMe | Et | Et |
| 157 | 2-BrCH2 | 6-OMe | Me | Me |
| 158 | 2-BrCH2 | 6-OMe | Et | Et |
| 159 | 2-BrCH2 | 3-OCF3 | Me | Me |
| 160 | 2-BrCH2 | 3-OCF3 | Et | Et |
| 161 | 2-BrCH2 | 4-CO2Me | Me | Me |
| 162 | 2-BrCH2 | 4-CO2Me | Et | Et |
| 163 | 2-BrCH2 | 4-SMe | Me | Me |
| 164 | 2-BrCH2 | 4-SMe | Et | Et |
| 165 | 2-BrCH2 | 4-NO2 | Me | Me |
| 166 | 2-BrCH2 | 4-NO2 | Et | Et |
| 167 | 2-BrCH2 | 4-CF3 | Me | Me |
| 168 | 2-BrCH2 | 4-CF3 | Et | Et |
| 169 | 2-BrCH2 | 4-SOMe | Me | Me |
| 170 | 2-BrCH2 | 4-SOMe | Et | Et |
| 171 | 2-BrCH2 | 4-SO2Me | Me | Me |
| 172 | 2-BrCH2 | 4-SO2Me | Et | Et |
| 173 | 2-BrCH2 | 4,6-Cl2 | Me | Me |
| 174 | 2-BrCH2 | 4,6-Cl2 | Et | Et |
| 175 | 2-BrCH2 | 4-Me-6-Cl | Me | Me |
| 176 | 2-BrCH2 | 4-Me-6-Cl | Et | Et |
| 177 | 2-BrCH2 | 4-OMe-6-Cl | Me | Me |
| 178 | 2-BrCH2 | 4-OMe-6-Cl | Et | Et |
| 179 | 2-BrCH2 | 4,6-(NO2)2 | Me | Me |
| 180 | 2-BrCH2 | 4,6-(NO2)2 | Et | Et |
| 181 | 3-BrCH2 | H | Me | Me |
| 182 | 3-BrCH2 | H | Me | Et |
| 183 | 3-BrCH2 | H | Me | i-Pr |
| 184 | 3-BrCH2 | H | Me | c-Pr |
| 185 | 3-BrCH2 | H | Et | Me |
| 186 | 3-BrCH2 | H | Et | Et |
| 187 | 4-BrCH2 | H | Me | Me |
| 188 | 4-BrCH2 | H | Me | Et |
| 189 | 4-BrCH2 | H | Me | i-Pr |
| 190 | 4-BrCH2 | H | Me | c-Pr |
| 191 | 4-BrCH2 | H | Et | Me |
| 192 | 4-BrCH2 | H | Et | Et |
| 193 | 3-ClCH2 | H | Me | Me |
| 194 | 3-ClCH2 | H | Me | Et |
| 195 | 3-ClCH2 | H | Me | i-Pr |
| 196 | 3-ClCH2 | H | Me | c-Pr |
| 197 | 3-ClCH2 | H | Et | Me |
| 198 | 3-ClCH2 | H | Et | Et |
| 199 | 4-ClCH2 | H | Me | Me |
| 200 | 4-ClCH2 | H | Me | Et |
| 201 | 4-ClCH2 | H | Me | i-Pr |
| 202 | 4-ClCH2 | H | Me | c-Pr |
| 203 | 4-ClCH2 | H | Et | Me |
| 204 | 4-ClCH2 | H | Et | Et |
| 205 | 4-BrCH2 | 2-Cl | Me | Me |
| 206 | 4-BrCH2 | 2-Cl | Me | Et |
| 207 | 4-BrCH2 | 2-Cl | Et | Et |
| 208 | 4-ClCH2 | 2-Cl | Me | Me |
| 209 | 4-ClCH2 | 2-Cl | Et | Me |
| 210 | 4-ClCH2 | 2-Cl | Et | Et |
| 211 | 4-BrCH2 | 2-NO2 | Me | Me |
| 212 | 4-BrCH2 | 2-NO2 | Et | Et |
| 213 | 4-BrCH2 | 2-CF3 | Me | Me |
| 214 | 4-BrCH2 | 2-CF3 | Et | Et |
| 215 | 4-BrCH2 | 2-CO2Me | Me | Me |
| 216 | 4-BrCH2 | 2-CO2Me | Et | Et |
| 217 | 4-BrCH2 | 2,6-Cl2 | Me | Me |
| 218 | 4-BrCH2 | 2,6-Cl2 | Et | Et |
| 219 | 4-BrCH2 | 2-F | Me | Ne |
| 210 | 4-BrCH2 | 2-F | Et | Et |
| 221 | 4-BrCH2 | 2,6-F2 | Me | Me |
| 222 | 4-BrCH2 | 2,6-F2 | Et | Et |
| 223 | 4-BrCH2 | 2-Br | Me | Me |
| 224 | 4-BrCH2 | 2-Br | Et | Et |
| 225 | 4-ClCH2 | 2-NO2 | Me | Me |
| 226 | 4-ClCH2 | 2-NO2 | Et | Et |
| 227 | 4-ClCH2 | 2-CF3 | Me | Me |
| 228 | 4-ClCH2 | 2-CF3 | Et | Et |
| 229 | 4-ClCH2 | 2-CO2Me | Me | Me |
| 230 | 4-ClCH2 | 2-CO2Me | Et | Et |
| 231 | 4-ClCH2 | 2,6-Cl2 | Me | Me |
| 232 | 4-ClCH2 | 2,6-Cl2 | Et | Et |
| 233 | 4-ClCH2 | 2-F | Me | Me |
| 234 | 4-ClCH2 | 2-F | Et | Et |
| 235 | 4-ClCH2 | 2,6-F2 | Me | Me |
| 236 | 4-ClCH2 | 2,6-F2 | Et | Et |
| 237 | 4-ClCH2 | 2-Br | Me | Me |
| 238 | 4-ClCH2 | 2-Br | Et | Et |
| 239 | 4-BrCH2 | 2-Me | Me | Me |
| 240 | 4-BrCH2 | 2-Me | Et | Et |
| 241 | 3-BrCH2 | 4-Cl | Me | Me |
| 242 | 3-BrCH2 | 4-Cl | Et | Et |
| 243 | 3-BrCH2 | 4-Me | Me | Me |
| 244 | 3-BrCH2 | 4-Me | Et | Et |
| 245 | 3-BrCH2 | 4-OMe | Me | Me |
| 246 | 3-BrCH2 | 4-OMe | Et | Et |
| 247 | 3-BrCH2 | 4-SO2Me | Me | Me |
| 248 | 3-BrCH2 | 4-SO2Me | Et | Et |
| 249 | 3-ClCH2 | 4-Cl | Me | Me |
| 250 | 3-ClCH2 | 4-Cl | Et | Et |
| 251 | 3-ClCH2 | 4-Me | Me | Me |
| 252 | 3-ClCH2 | 4-Me | Et | Et |
| 253 | 3-ClCH2 | 4-OMe | Me | Me |
| 254 | 3-ClCH2 | 4-OMe | Et | Et |
| 255 | 3-ClCH2 | 4-SO2Me | Me | Me |
| 256 | 3-ClCH2 | 4-SO2Me | Et | Et |
| 257 | 3-BrCH2 | 4,6-Cl2 | Me | Me |
| 258 | 3-BrCH2 | 4,6-Cl2 | Et | Et |
| 259 | 3-ClCH2 | 4,6-Cl2 | Me | Me |
| 260 | 3-ClCH2 | 4,6-Cl2 | Et | Et |
| 261 | 3-ClCH2 | 4-Cl,6-Br | Me | Me |
| 262 | 3-ClCH2 | 4-Cl,6-Br | Et | Et |
| 263 | 3-ClCH2 | 5-Cl | Me | Me |
| 264 | 3-ClCH2 | 5-Cl | Et | Et |
| 265 | 2-ICH2 | H | Me | Me |
| 266 | 2-ICH2 | H | Et | Et |
| 267 | 3-ICH2 | H | Me | Me |
| 268 | 3-ICH2 | H | Et | Et |
| 269 | 4-ICH2 | H | Me | Me |

TABLE 1-1-continued

| No. | ACH2 | Xn | R1 | R2 |
|---|---|---|---|---|
| 270 | 4-ICH2 | H | Et | Et |
| 271 | 2-HOCH2 | H | Me | Me |
| 272 | 2-HOCH2 | H | Me | Et |
| 273 | 2-HOCH2 | H | Me | n-Pr |
| 274 | 2-HOCH2 | H | Me | i-Pr |
| 275 | 2-HOCH2 | H | Me | n-Bu |
| 276 | 2-HOCH2 | H | Me | s-Bu |
| 277 | 2-HOCH2 | H | Me | i-Bu |
| 278 | 2-HOCH2 | H | Me | t-Bu |
| 279 | 2-HOCH2 | H | Me | c-Pr |
| 280 | 2-HOCH2 | H | Me | c-Bu |
| 281 | 2-HOCH2 | H | Me | n-Pen |
| 282 | 2-HOCH2 | H | Me | c-Pen |
| 283 | 2-HOCH2 | H | Me | n-Hex |
| 284 | 2-HOCH2 | H | Me | c-Hex |
| 285 | 2-HOCH2 | H | Me | Bn |
| 286 | 2-HOCH2 | H | Me | CH(Me)Ph |
| 287 | 2-HOCH2 | H | Me | CH2CH2Ph |
| 288 | 2-HOCH2 | H | Me | CH2CH=CH2 |
| 289 | 2-HOCH2 | H | Me | CH2(4-Cl—C6H4) |
| 290 | 2-HOCH2 | H | Me | CH2(2-Cl—C6H4) |
| 291 | 2-HOCH2 | H | Et | Me |
| 292 | 2-HOCH2 | H | Et | Et |
| 293 | 2-HOCH2 | H | Et | i-Pr |
| 294 | 2-HOCH2 | H | Et | c-Pr |
| 295 | 2-HOCH2 | H | i-Pr | Me |
| 296 | 2-HOCH2 | H | i-Pr | i-Pr |
| 297 | 2-HOCH2 | H | CH2CH=CH2 | Me |
| 298 | 2-HOCH2 | H | CH2CH=CH2 | CH2CH=CH2 |
| 299 | 2-HOCH2 | H | Bn | Me |
| 300 | 2-HOCH2 | H | Bn | Bn |
| 301 | 2-HOCH2 | 3-Cl | Me | Me |
| 302 | 2-HOCH2 | 3-Cl | Me | Et |
| 303 | 2-HOCH2 | 3-Cl | Me | i-Pr |
| 304 | 2-HOCH2 | 3-Cl | Me | c-Pr |
| 305 | 2-HOCH2 | 3-Cl | Et | Me |
| 306 | 2-HOCH2 | 3-Cl | Et | Et |
| 307 | 2-HOCH2 | 3-Cl | Me | Me |
| 308 | 2-HOCH2 | 3-Cl | Me | Et |
| 309 | 2-HOCH2 | 3-Cl | Me | i-Pr |
| 310 | 2-HOCH2 | 3-Cl | Me | c-Pr |
| 311 | 2-HOCH2 | 3-Cl | Et | Me |
| 312 | 2-HOCH2 | 3-Cl | Et | Et |
| 313 | 2-HOCH2 | 4-Cl | Me | Me |
| 314 | 2-HOCH2 | 4-Cl | Me | Et |
| 315 | 2-HOCH2 | 4-Cl | Me | i-Pr |
| 316 | 2-HOCH2 | 4-Cl | Me | c-Pr |
| 317 | 2-HOCH2 | 4-Cl | Et | Me |
| 318 | 2-HOCH2 | 4-Cl | Et | Et |
| 319 | 2-HOCH2 | 5-Cl | Me | Me |
| 320 | 2-HOCH2 | 5-Cl | Me | Et |
| 321 | 2-HOCH2 | 5-Cl | Me | i-Pr |
| 322 | 2-HOCH2 | 5-Cl | Me | c-Pr |
| 323 | 2-HOCH2 | 5-Cl | Et | Me |
| 324 | 2-HOCH2 | 5-Cl | Et | Et |
| 325 | 2-HOCH2 | 6-Cl | Me | Me |
| 326 | 2-HOCH2 | 6-Cl | Me | Et |
| 327 | 2-HOCH2 | 6-Cl | Me | i-Pr |
| 328 | 2-HOCH2 | 6-Cl | Me | c-Pr |
| 329 | 2-HOCH2 | 6-Cl | Et | Me |
| 330 | 2-HOCH2 | 6-Cl | Et | Et |
| 331 | 2-HOCH2 | 3-OMe | Me | Me |
| 332 | 2-HOCH2 | 3-OMe | Et | Et |
| 333 | 2-HOCH2 | 4-OMe | Me | Me |
| 334 | 2-HOCH2 | 4-OMe | Et | Et |
| 335 | 2-HOCH2 | 5-OMe | Me | Me |
| 336 | 2-HOCH2 | 5-OMe | Et | Et |
| 337 | 2-HOCH2 | 6-OMe | Me | Me |
| 338 | 2-HOCH2 | 6-OMe | Et | Et |
| 339 | 2-HOCH2 | 3-OCF3 | Me | Me |
| 340 | 2-HOCH2 | 3-OCF3 | Et | Et |
| 341 | 2-HOCH2 | 4-CO2Me | Me | Me |
| 342 | 2-HOCH2 | 4-CO2Me | Et | Et |
| 343 | 2-HOCH2 | 4-SMe | Me | Me |
| 344 | 2-HOCH2 | 4-SMe | Et | Et |
| 345 | 2-HOCH2 | 4-NO2 | Me | Me |
| 346 | 2-HOCH2 | 4-NO2 | Et | Et |
| 347 | 2-HOCH2 | 4-CF3 | Me | Me |
| 348 | 2-HOCH2 | 4-CF3 | Et | Et |
| 349 | 2-HOCH2 | 4-SOMe | Me | Me |
| 350 | 2-HOCH2 | 4-SOMe | Et | Et |
| 351 | 2-HOCH2 | 4-SO2Me | Me | Me |
| 352 | 2-HOCH2 | 4-SO2Me | Et | Et |
| 353 | 2-HOCH2 | 4,6-Cl2 | Me | Me |
| 354 | 2-HOCH2 | 4,6-Cl2 | Et | Et |
| 355 | 2-HOCH2 | 4-Me-6-Cl | Me | Me |
| 356 | 2-HOCH2 | 4-Me-6-Cl | Et | Et |
| 357 | 2-HOCH2 | 4-OMe-6-Cl | Me | Me |
| 358 | 2-HOCH2 | 4-OMe-6-Cl | Et | Et |
| 359 | 2-HOCH2 | 4,6-(NO2)2 | Me | Me |
| 360 | 2-HOCH2 | 4,6-(NO2)2 | Et | Et |
| 361 | 3-HOCH2 | H | Me | Me |
| 362 | 3-HOCH2 | H | Me | Et |
| 363 | 3-HOCH2 | H | Me | i-Pr |
| 364 | 3-HOCH2 | H | Me | c-Pr |
| 365 | 3-HOCH2 | H | Et | Me |
| 366 | 3-HOCH2 | H | Et | Et |
| 367 | 4-HOCH2 | H | Me | Me |
| 368 | 4-HOCH2 | H | Me | Et |
| 369 | 4-HOCH2 | H | Me | i-Pr |
| 370 | 4-HOCH2 | H | Me | c-Pr |
| 371 | 4-HOCH2 | H | Et | Me |
| 372 | 4-HOCH2 | H | Et | Et |
| 373 | 4-HOCH2 | 2-Cl | Me | Me |
| 374 | 4-HOCH2 | 2-Cl | Et | Me |
| 375 | 4-HOCH2 | 2-Cl | Et | Et |
| 376 | 4-HOCH2 | 2-NO2 | Me | Me |
| 377 | 4-HOCH2 | 2-NO2 | Et | Et |
| 378 | 4-HOCH2 | 2-CF3 | Me | Me |
| 379 | 4-HOCH2 | 2-CF3 | Et | Et |
| 380 | 4-HOCH2 | 2-CO2Me | Me | Me |
| 381 | 4-HOCH2 | 2-CO2Me | Et | Et |
| 382 | 4-HOCH2 | 2,6-Cl2 | Me | Me |
| 383 | 4-HOCH2 | 2,6-Cl2 | Et | Et |
| 384 | 4-HOCH2 | 2-F | Me | Me |
| 385 | 4-HOCH2 | 2-F | Et | Et |
| 386 | 4-HOCH2 | 2,6-F2 | Me | Me |
| 387 | 4-HOCH2 | 2,6-F2 | Et | Et |
| 388 | 4-HOCH2 | 2-Br | Me | Me |
| 389 | 4-HOCH2 | 2-Br | Et | Et |
| 390 | 4-HOCH2 | 2-Br | Me | Et |
| 391 | 3-HOCH2 | 4-Cl | Me | Me |
| 392 | 3-HOCH2 | 4-Cl | Et | Et |
| 393 | 3-HOCH2 | 4-Me | Me | Me |
| 394 | 3-HOCH2 | 4-Me | Et | Et |
| 395 | 3-HOCH2 | 4-OMe | Me | Me |
| 396 | 3-HOCH2 | 4-OMe | Et | Et |
| 397 | 3-HOCH2 | 4-SO2Me | Me | Me |
| 398 | 3-HOCH2 | 4-SO2Me | Et | Et |
| 399 | 3-HOCH2 | 4,6-Cl2 | Me | Me |
| 400 | 3-HOCH2 | 4,6-Cl2 | Et | Et |
| 401 | 3-HOCH2 | 4-Cl,6-Br | Me | Me |
| 402 | 3-HOCH2 | 4-Cl,6-Br | Et | Et |
| 403 | 3-HOCH2 | 5-Cl | Me | Me |
| 404 | 3-HOCH2 | 5-Cl | Et | Et |

TABLE 1-2

| No. | position of A'CH2 | R3 | Xn | R1 | R2 |
|---|---|---|---|---|---|
| 1 | 2 | C6H5 | H | Me | Me |
| 2 | 2 | C6H5 | H | Me | Et |
| 3 | 2 | C6H5 | H | Me | i-Pr |
| 4 | 2 | C6H5 | H | Me | c-Pr |
| 5 | 2 | C6H5 | H | Et | Et |
| 6 | 2 | 2-Me—C6H4 | H | Me | Me |
| 7 | 2 | 2-Me—C6H4 | H | Me | Et |
| 8 | 2 | 2-Me—C6H4 | H | Me | i-Pr |
| 9 | 2 | 2-Me—C6H4 | H | Et | Me |
| 10 | 2 | 2-Me—C6H4 | H | Et | Et |
| 11 | 2 | 3-Me—C6H4 | H | Me | Me |
| 12 | 2 | 3-Me—C6H4 | H | Me | Et |
| 13 | 2 | 3-Me—C6H4 | H | Me | i-Pr |
| 14 | 2 | 3-Me—C6H4 | H | Et | Me |
| 15 | 2 | 3-Me—C6H4 | H | Et | Et |
| 16 | 2 | 4-Me—C6H4 | H | Me | Me |
| 17 | 2 | 4-Me—C6H4 | H | Me | Et |
| 18 | 2 | 4-Me—C6H4 | H | Me | i-Pr |
| 19 | 2 | 4-Me—C6H4 | H | Et | Me |
| 20 | 2 | 4-Me—C6H4 | H | Et | Et |
| 21 | 2 | 2-CF3—C6H4 | H | Me | Me |
| 22 | 2 | 2-CF3—C6H4 | H | Me | Et |
| 23 | 2 | 2-CF3—C6H4 | H | Me | i-Pr |
| 24 | 2 | 2-CF3—C6H4 | H | Et | Me |
| 25 | 2 | 2-CF3—C6H4 | H | Et | Et |
| 26 | 2 | 3-CF3—C6H4 | H | Me | Me |
| 27 | 2 | 3-CF3—C6H4 | H | Me | Et |
| 28 | 2 | 3-CF3—C6H4 | H | Me | i-Pr |
| 29 | 2 | 3-CF3—C6H4 | H | Et | Me |
| 30 | 2 | 3-CF3—C6H4 | H | Et | Et |
| 31 | 2 | 4-CF3—C6H4 | H | Me | Me |
| 32 | 2 | 4-CF3—C6H4 | H | Me | Et |
| 33 | 2 | 4-CF3—C6H4 | H | Et | Me |
| 34 | 2 | 4-CF3—C6H4 | H | Et | Et |
| 35 | 2 | 2-OMe—C6H4 | H | Me | Me |
| 36 | 2 | 2-OMe—C6H4 | H | Et | Et |
| 37 | 2 | 3-OMe—C6H4 | H | Me | Me |
| 38 | 2 | 3-OMe—C6H4 | H | Et | Et |
| 39 | 2 | 4-OMe—C6H4 | H | Me | Me |
| 40 | 2 | 4-OMe—C6H4 | H | Et | Et |
| 41 | 2 | 2-OCF3—C6H4 | H | Me | Me |
| 42 | 2 | 2-OCF3—C6H4 | H | Me | Et |
| 43 | 2 | 3-OCF3—C6H4 | H | Et | Me |
| 44 | 2 | 3-OCF3—C6H4 | H | Et | Et |
| 45 | 2 | 4-OCF3—C6H4 | H | Me | Me |
| 46 | 2 | 4-OCF3—C6H4 | H | Et | Et |
| 47 | 2 | 2-F—C6H4 | H | Me | Me |
| 48 | 2 | 2-F—C6H4 | H | Et | Et |
| 49 | 2 | 3-F—C6H4 | H | Me | Me |
| 50 | 2 | 3-F—C6H4 | H | Et | Et |
| 51 | 2 | 4-F—C6H4 | H | Me | Me |
| 52 | 2 | 4-F—C6H4 | H | Me | Et |
| 53 | 2 | 2-Br—C6H4 | H | Et | Me |
| 54 | 2 | 2-Br—C6H4 | H | Et | Et |
| 55 | 2 | 4-Br—C6H4 | H | Me | Me |
| 56 | 2 | 4-Br—C6H4 | H | Et | Et |
| 57 | 2 | 2,4-Cl2—C6H3 | H | Me | Me |
| 58 | 2 | 2,4-Cl2—C6H3 | H | Et | Et |
| 59 | 2 | 2-CN—C6H4 | H | Me | Me |
| 60 | 2 | 2-CN—C6H4 | H | Et | Et |
| 61 | 2 | 3-CN—C6H4 | H | Me | Me |
| 62 | 2 | 3-CN—C6H4 | H | Et | Et |
| 63 | 2 | 4-CN—C6H4 | H | Me | Me |
| 64 | 2 | 4-CN—C6H4 | H | Et | Et |
| 65 | 2 | 2-CO2Me—C6H4 | H | Me | Me |
| 66 | 2 | 2-CO2Me—C6H4 | H | Et | Et |
| 67 | 2 | 3-CO2Me—C6H4 | H | Me | Me |
| 68 | 2 | 3-CO2Me—C6H4 | H | Et | Et |
| 69 | 2 | 4-CO2Me—C6H4 | H | Me | Me |
| 70 | 2 | 4-CO2Me—C6H4 | H | Et | Et |
| 71 | 2 | 2-NO2—C6H4 | H | Me | Me |
| 72 | 2 | 2-NO2—C6H4 | H | Me | Et |
| 73 | 2 | 3-NO2—C6H4 | H | Et | Me |
| 74 | 2 | 3-NO2—C6H4 | H | Et | Et |
| 75 | 2 | 4-NO2—C6H4 | H | Me | Me |
| 76 | 2 | 4-NO2—C6H4 | H | Et | Et |

TABLE 1-2-continued

| No. | position of A'CH2 | R3 | Xn | R1 | R2 |
|---|---|---|---|---|---|
| 77 | 2 | 2-SO2Me—C6H4 | H | Me | Me |
| 78 | 2 | 2-SO2Me—C6H4 | H | Et | Et |
| 79 | 2 | 3-SO2Me—C6H4 | H | Me | Me |
| 80 | 2 | 3-SO2Me—C6H4 | H | Et | Et |
| 81 | 2 | 4-SO2Me—C6H4 | H | Me | Me |
| 82 | 2 | 4-SO2Me—C6H4 | H | Me | Et |
| 83 | 2 | 2-Sme—C6H4 | H | Et | Me |
| 84 | 2 | 2-Sme—C6H4 | H | Et | Et |
| 85 | 2 | 3-Sme—C6H4 | H | Me | Me |
| 86 | 2 | 3-Sme—C6H4 | H | Et | Et |
| 87 | 2 | 4-Sme—C6H4 | H | Me | Me |
| 88 | 2 | 4-Sme—C6H4 | H | Et | Et |
| 89 | 2 | 4-SOMe—C6H4 | H | Me | Me |
| 90 | 2 | 2-SOMe—C6H4 | H | Et | Et |
| 91 | 2 | 2,3-Cl2—C6H3 | H | Me | Me |
| 92 | 2 | 2,3-Cl2—C6H3 | H | Et | Et |
| 93 | 2 | 2,5-Cl2—C6H3 | H | Me | Me |
| 94 | 2 | 2,5-Cl2—C6H3 | H | Et | Et |
| 95 | 2 | 2,6-Cl2—C6H3 | H | Me | Me |
| 96 | 2 | 2,6-Cl2—C6H3 | H | Et | Et |
| 97 | 2 | 2,4,6-Cl3—C6H2 | H | Me | Me |
| 98 | 2 | 2,4,6-Cl3—C6H2 | H | Et | Et |
| 99 | 2 | 2-Cl,4-CO2Me—C6H3 | H | Me | Me |
| 100 | 2 | 2-Cl,4-CO2Me—C6H3 | H | Et | Et |
| 101 | 2 | 3-Cl,4-CO2Me—C6H3 | H | Me | Me |
| 102 | 2 | 3-Cl,4-CO2Me—C6H3 | H | Me | Et |
| 103 | 2 | 4-Cl,2-CO2Me—C6H3 | H | Et | Me |
| 104 | 2 | 4-Cl,2-CO2Me—C6H3 | H | Et | Et |
| 105 | 2 | 2-Cl,4-CF3—C6H3 | H | Me | Me |
| 106 | 2 | 2-Cl,4-CF3—C6H3 | H | Et | Et |
| 107 | 2 | C6F5 | H | Me | Me |
| 108 | 2 | C6F5 | H | Et | Et |
| 109 | 2 | 2-CN,4-Cl—C6H3 | H | Me | Me |
| 110 | 2 | 2-CN,4-Cl—C6H3 | H | Et | Et |
| 111 | 2 | 2-COMe—C6H4 | H | Me | Me |
| 112 | 2 | 2-COMe—C6H4 | H | Me | Et |
| 113 | 2 | 3-COMe—C6H4 | H | Et | Me |
| 114 | 2 | 3-COMe—C6H4 | H | Et | Et |
| 115 | 2 | 4-COMe—C6H4 | H | Me | Me |
| 116 | 2 | 4-COMe—C6H4 | H | Et | Et |
| 117 | 2 | 2,4-Cl2,3-Me—C6H2 | H | Me | Me |
| 118 | 2 | 2,4-Cl2,3-Me—C6H2 | H | Et | Et |
| 119 | 2 | 2,4,5-Cl3—C6H2 | H | Me | Me |
| 120 | 2 | 2,4,5-Cl3—C6H2 | H | Et | Et |
| 121 | 2 | C6H5 | 4-Cl | Me | Me |
| 122 | 2 | C6H5 | 4-Cl | Et | Et |
| 123 | 2 | 2-Cl—C6H4 | 4-Cl | Me | Me |
| 124 | 2 | 2-Cl—C6H4 | 4-Cl | Et | Et |
| 125 | 2 | 3-Cl—C6H4 | 4-Cl | Me | Me |
| 126 | 2 | 3-Cl—C6H4 | 4-Cl | Et | Et |
| 127 | 2 | 4-Cl—C6H4 | 4-Cl | Me | Me |
| 128 | 2 | 4-Cl—C6H4 | 4-Cl | Et | Et |
| 129 | 2 | 2-Me—C6H4 | 4-Cl | Me | Me |
| 130 | 2 | 2-Me—C6H4 | 4-Cl | Et | Et |
| 131 | 2 | 3-Me—C6H4 | 4-Cl | Me | Me |
| 132 | 2 | 3-Me—C6H4 | 4-Cl | Et | Et |
| 133 | 2 | 4-Me—C6H4 | 4-Cl | Me | Me |
| 134 | 2 | 4-Me—C6H4 | 4-Cl | Et | Et |
| 135 | 2 | 2-Me—C6H4 | 4-Cl | Me | H |
| 136 | 2 | 2-CF3—C6H4 | 4-Cl | Et | Et |
| 137 | 2 | 3-CF3—C6H4 | 4-Cl | Me | Me |
| 138 | 2 | 3-CF3—C6H4 | 4-Cl | Et | Et |
| 139 | 2 | 4-CF3—C6H4 | 4-Cl | Me | Me |
| 140 | 2 | 4-CF3—C6H4 | 4-Cl | Et | Et |
| 141 | 2 | 2-OMe—C6H4 | 4-Cl | Me | Me |
| 142 | 2 | 2-OMe—C6H4 | 4-Cl | Et | Et |
| 143 | 2 | 3-OMe—C6H4 | 4-Cl | Me | Me |
| 144 | 2 | 3-OMe—C6H4 | 4-Cl | Et | Et |
| 145 | 2 | 4-OMe—C6H4 | 4-Cl | Me | Me |
| 146 | 2 | 4-OMe—C6H4 | 4-Cl | Et | Et |
| 147 | 2 | 2-OCF3—C6H4 | 4-Cl | Me | Me |
| 148 | 2 | 2-OCF3—C6H4 | 4-Cl | Et | Et |
| 149 | 2 | 3-OCF3—C6H4 | 4-Cl | Me | Me |
| 150 | 2 | 3-OCF3—C6H4 | 4-Cl | Et | Et |
| 151 | 2 | 4-OCF3—C6H4 | 4-Cl | Me | Me |
| 152 | 2 | 4-OCF3—C6H4 | 4-Cl | Et | Et |

TABLE 1-2-continued

| No. | position of A'CH2 | R3 | Xn | R1 | R2 |
|---|---|---|---|---|---|
| 153 | 2 | 2-Br—C6H4 | 4-Cl | Me | Me |
| 154 | 2 | 2-Br—C6H4 | 4-Cl | Et | Et |
| 155 | 2 | 3-Br—C6H4 | 4-Cl | Me | Me |
| 156 | 2 | 3-Br—C6H4 | 4-Cl | Et | Et |
| 157 | 2 | 4-Br—C6H4 | 4-Cl | Me | Me |
| 158 | 2 | 4-Br—C6H4 | 4-Cl | Et | Et |
| 159 | 2 | 2-CO2Me—C6H4 | 4-Cl | Me | Me |
| 160 | 2 | 2-CO2Me—C6H4 | 4-Cl | Et | Et |
| 161 | 2 | 3-CO2Me—C6H4 | 4-Cl | Me | Me |
| 162 | 2 | 3-CO2Me—C6H4 | 4-Cl | Et | Et |
| 163 | 2 | 4-CO2Me—C6H4 | 4-Cl | Me | Me |
| 164 | 2 | 4-CO2Me—C6H4 | 4-Cl | Et | Et |
| 165 | 2 | 2-CN—C6H4 | 4-Cl | Me | Me |
| 166 | 2 | 2-CN—C6H4 | 4-Cl | Et | Et |
| 167 | 2 | 3-CN—C6H4 | 4-Cl | Me | Me |
| 168 | 2 | 3-CN—C6H4 | 4-Cl | Et | Et |
| 169 | 2 | 4-CN—C6H4 | 4-Cl | Me | Me |
| 170 | 2 | 4-CN—C6H4 | 4-Cl | Et | Et |
| 171 | 2 | 2-COMe—C6H4 | 4-Cl | Me | Me |
| 172 | 2 | 2-COMe—C6H4 | 4-Cl | Et | Et |
| 173 | 2 | 3-COMe—C6H4 | 4-Cl | Me | Me |
| 174 | 2 | 3-COMe—C6H4 | 4-Cl | Et | Et |
| 175 | 2 | 4-COMe—C6H4 | 4-Cl | Me | Me |
| 176 | 2 | 4-COMe—C6H4 | 4-Cl | Et | Et |
| 177 | 2 | 2-NO2—C6H4 | 4-Cl | Me | Me |
| 178 | 2 | 2-NO2—C6H4 | 4-Cl | Et | Et |
| 179 | 2 | 3-NO2—C6H4 | 4-Cl | Me | Me |
| 180 | 2 | 3-NO2—C6H4 | 4-Cl | Et | Et |
| 181 | 2 | 4-NO2—C6H4 | 4-Cl | Me | Me |
| 182 | 2 | 4-NO2—C6H4 | 4-Cl | Et | Et |
| 183 | 2 | 2,4-Cl2—C6H3 | 4-Cl | Me | Me |
| 184 | 2 | 2,4-Cl2—C6H3 | 4-Cl | Et | Et |
| 185 | 2 | 2,4-F2—C6H3 | 4-Cl | Me | Me |
| 186 | 2 | 2,4-F2—C6H3 | 4-Cl | Et | Et |
| 187 | 2 | 2,4,6-Cl3—C6H2 | 4-Cl | Me | Me |
| 188 | 2 | 2,4,6-Cl3—C6H2 | 4-Cl | Et | Et |
| 189 | 2 | 2-Cl,4-CO2Me—C6H3 | 4-Cl | Me | Me |
| 190 | 2 | 2-Cl,4-CO2Me—C6H3 | 4-Cl | Et | Et |
| 191 | 2 | 3-Cl,4-CO2Me—C6H3 | 4-Cl | Me | Me |
| 192 | 2 | 3-Cl,4-CO2Me—C6H3 | 4-Cl | Et | Et |
| 193 | 2 | 4-Cl,2-CO2Me—C6H3 | 4-Cl | Me | Me |
| 194 | 2 | 4-Cl,2-CO2Me—C6H3 | 4-Cl | Et | Et |
| 195 | 2 | 2-Cl,4-CF3—C6H3 | 4-Cl | Me | Me |
| 196 | 2 | 2-Cl,4-CF3—C6H3 | 4-Cl | Et | Et |
| 197 | 2 | C6F5 | 4-Cl | Me | Me |
| 198 | 2 | C6F5 | 4-Cl | Et | Et |
| 199 | 2 | 2-CN,4-Cl—C6H3 | 4-Cl | Me | Me |
| 200 | 2 | 2-CN,4-Cl—C6H3 | 4-Cl | Et | Et |
| 201 | 2 | 2,4-Cl2,3-Me—C6H2 | 4-Cl | Me | Me |
| 202 | 2 | 2,4-Cl2,3-Me—C6H2 | 4-Cl | Et | Et |
| 203 | 2 | C6H5 | 4-Br | Me | Me |
| 204 | 2 | C6H5 | 4-Br | Et | Et |
| 205 | 2 | C6H5 | 4-NO2 | Me | Me |
| 206 | 2 | C6H5 | 4-NO2 | Et | Et |
| 207 | 2 | C6H5 | 4,6-Cl2 | Me | Me |
| 208 | 2 | C6H5 | 4,6-Cl2 | Et | Et |
| 209 | 2 | C6H5 | 4-F | Me | Me |
| 210 | 2 | C6H5 | 4-F | Et | Et |
| 211 | 3 | C6H5 | H | Me | Me |
| 212 | 3 | C6H5 | H | Et | Et |
| 213 | 3 | 2-Me—C6H4 | H | Me | Me |
| 214 | 3 | 2-Me—C6H4 | H | Et | Et |
| 215 | 3 | 3-Me—C6H4 | H | Me | Me |
| 216 | 3 | 3-Me—C6H4 | H | Et | Et |
| 217 | 3 | 4-Me—C6H4 | H | Me | Me |
| 218 | 3 | 4-Me—C6H4 | H | Et | Et |
| 219 | 3 | 2-CF3—C6H4 | H | Me | Me |
| 220 | 3 | 2-CF3—C6H4 | H | Et | Et |
| 221 | 3 | 3-CF3—C6H4 | H | Me | Me |
| 222 | 3 | 3-CF3—C6H4 | H | Et | Et |
| 223 | 3 | 4-CF3—C6H4 | H | Me | Me |
| 224 | 3 | 4-CF3—C6H4 | H | Et | Et |
| 225 | 3 | 2-OMe—C6H4 | H | Me | Me |
| 226 | 3 | 2-OMe—C6H4 | H | Et | Et |
| 227 | 3 | 3-OMe—C6H4 | H | Me | Me |
| 228 | 3 | 3-OMe—C6H4 | H | Et | Et |

TABLE 1-2-continued

| No. | position of A'CH2 | R3 | Xn | R1 | R2 |
|---|---|---|---|---|---|
| 229 | 3 | 4-OMe—C6H4 | H | Me | Me |
| 230 | 3 | 4-OMe—C6H4 | H | Et | Et |
| 231 | 3 | 2-OCF3—C6H4 | H | Me | Me |
| 232 | 3 | 2-OCF3—C6H4 | H | Et | Et |
| 233 | 3 | 3-OCF3—C6H4 | H | Me | Me |
| 234 | 3 | 3-OCF3—C6H4 | H | Et | Et |
| 235 | 3 | 4-OCF3—C6H4 | H | Me | Me |
| 236 | 3 | 4-OCF3—C6H4 | H | Et | Et |
| 237 | 3 | 2-F—C6H4 | H | Me | Me |
| 238 | 3 | 2-F—C6H4 | H | Et | Et |
| 239 | 3 | 3-F—C6H4 | H | Me | Me |
| 240 | 3 | 3-F—C6H4 | H | Et | Et |
| 241 | 3 | 4-F—C6H4 | H | Me | Me |
| 242 | 3 | 4-F—C6H4 | H | Et | Et |
| 243 | 3 | 2-Br—C6H4 | H | Me | Me |
| 244 | 3 | 2-Br—C6H4 | H | Et | Et |
| 245 | 3 | 4-Br—C6H4 | H | Me | Me |
| 246 | 3 | 4-Br—C6H4 | H | Et | Et |
| 247 | 3 | 2,4-Cl2—C6H3 | H | Me | Me |
| 248 | 3 | 2,4-Cl2—C6H3 | H | Et | Et |
| 249 | 3 | 2-CN—C6H4 | H | Me | Me |
| 250 | 3 | 2-CN—C6H4 | H | Et | Et |
| 251 | 3 | 3-CN—C6H4 | H | Me | Me |
| 252 | 3 | 3-CN—C6H4 | H | Et | Et |
| 253 | 3 | 4-CN—C6H4 | H | Me | Me |
| 254 | 3 | 4-CN—C6H4 | H | Et | Et |
| 255 | 3 | 2-CO2Me—C6H4 | H | Me | Me |
| 256 | 3 | 2-CO2Me—C6H4 | H | Et | Et |
| 257 | 3 | 3-CO2Me—C6H4 | H | Me | Me |
| 258 | 3 | 3-CO2Me—C6H4 | H | Et | Et |
| 259 | 3 | 4-CO2Me—C6H4 | H | Me | Me |
| 260 | 3 | 4-CO2Me—C6H4 | H | Et | Et |
| 261 | 3 | 2-NO2—C6H4 | H | Me | Me |
| 262 | 3 | 2-NO2—C6H4 | H | Et | Et |
| 263 | 3 | 3-NO2—C6H4 | H | Me | Me |
| 264 | 3 | 3-NO2—C6H4 | H | Et | Et |
| 265 | 3 | 4-NO2—C6H4 | H | Me | Me |
| 266 | 3 | 4-NO2—C6H4 | H | Et | Et |
| 267 | 3 | 2-SO2Me—C6H4 | H | Me | Me |
| 268 | 3 | 2-SO2Me—C6H4 | H | Et | Et |
| 269 | 3 | 3-SO2Me—C6H4 | H | Me | Me |
| 270 | 3 | 3-SO2Me—C6H4 | H | Et | Et |
| 271 | 3 | 4-SO2Me—C6H4 | H | Me | Me |
| 272 | 3 | 4-SO2Me—C6H4 | H | Et | Et |
| 273 | 3 | 2-SMe—C6H4 | H | Me | Me |
| 274 | 3 | 2-SMe—C6H4 | H | Et | Et |
| 275 | 3 | 3-SMe—C6H4 | H | Me | Me |
| 276 | 3 | 3-SMe—C6H4 | H | Et | Et |
| 277 | 3 | 4-SMe—C6H4 | H | Me | Me |
| 278 | 3 | 4-SMe—C6H4 | H | Et | Et |
| 279 | 3 | 4-SOMe—C6H4 | H | Me | Me |
| 280 | 3 | 2-SOMe—C6H4 | H | Et | Et |
| 281 | 3 | 2,3-Cl2—C6H3 | H | Me | Me |
| 282 | 3 | 2,3-Cl2—C6H3 | H | Et | Et |
| 283 | 3 | 2,5-Cl2—C6H3 | H | Me | Me |
| 284 | 3 | 2,5-Cl2—C6H3 | H | Et | Et |
| 285 | 3 | 2,6-Cl2—C6H3 | H | Me | Me |
| 286 | 3 | 2,6-Cl2—C6H3 | H | Et | Et |
| 287 | 3 | 2,4,6-Cl3—C6H2 | H | Me | Me |
| 288 | 3 | 2,4,6-Cl3—C6H2 | H | Et | Et |
| 289 | 3 | 2-Cl,4-CO2Me—C6H3 | H | Me | Me |
| 290 | 3 | 2-Cl,4-CO2Me—C6H3 | H | Et | Et |
| 291 | 3 | 3-Cl,4-CO2Me—C6H3 | H | Me | Me |
| 292 | 3 | 3-Cl,4-CO2Me—C6H3 | H | Et | Et |
| 293 | 3 | 4-Cl,2-CO2Me—C6H3 | H | Me | Me |
| 294 | 3 | 4-Cl,2-CO2Me—C6H3 | H | Et | Et |
| 295 | 3 | 2-Cl,4-CF3—C6H3 | H | Me | Me |
| 296 | 3 | 2-Cl,4-CF3—C6H3 | H | Et | Et |
| 297 | 3 | C6F5 | H | Me | Me |
| 298 | 3 | C6F5 | H | Et | Et |
| 299 | 3 | 2-CN,4-Cl—C6H3 | H | Me | Me |
| 300 | 3 | 2-CN,4-Cl—C6H3 | H | Et | Et |
| 301 | 3 | 2-COMe—C6H4 | H | Me | Me |
| 302 | 3 | 2-COMe—C6H4 | H | Et | Et |
| 303 | 3 | 3-COMe—C6H4 | H | Me | Me |
| 304 | 3 | 3-COMe—C6H4 | H | Et | Et |

TABLE 1-2-continued

| No. | position of A'CH2 | R3 | Xn | R1 | R2 |
|---|---|---|---|---|---|
| 305 | 3 | 4-COMe—C6H4 | H | Me | Me |
| 306 | 3 | 4-COMe—C6H4 | H | Et | Et |
| 307 | 3 | 2,4-Cl2,3-Me—C6H2 | H | Me | Me |
| 308 | 3 | 2,4-Cl2,3-Me—C6H2 | H | Et | Et |
| 309 | 3 | 2,4,5-Cl3—C6H2 | H | Me | Me |
| 310 | 3 | 2,4,5-Cl3—C6H2 | H | Et | Et |
| 311 | 3 | C6H5 | 4-Cl | Me | Me |
| 312 | 3 | C6H5 | 4-Cl | Et | Et |
| 313 | 3 | C6H5 | 2,4-Cl2 | Me | Me |
| 314 | 3 | C6H5 | 2,4-Cl2 | Et | Et |
| 315 | 3 | 2-Me—C6H4 | 4-Cl | Me | Me |
| 316 | 3 | 2-Me—C6H4 | 4-Cl | Et | Et |
| 317 | 3 | 2-Me—C6H4 | 2,4-Cl2 | Me | Me |
| 318 | 3 | 2-Me—C6H4 | 2,4-Cl2 | Et | Et |
| 319 | 3 | 3-CF3—C6H4 | 4-Cl | Me | Me |
| 320 | 3 | 3-CF3—C6H4 | 4-Cl | Et | Et |
| 321 | 3 | 3-CF3—C6H4 | 2,4-Cl2 | Me | Me |
| 322 | 3 | 3-CF3—C6H4 | 2,4-Cl2 | Et | Et |
| 323 | 3 | 3-CF3—C6H4 | 4-OMe | Me | Me |
| 324 | 3 | 3-CF3—C6H4 | 4-OMe | Et | Et |
| 325 | 3 | 3-Me—C6H4 | 4-Cl | Me | Me |
| 326 | 3 | 3-Me—C6H4 | 4-Cl | Et | Et |
| 327 | 3 | 4-Me—C6H4 | 4-Cl | Me | Me |
| 328 | 3 | 4-Me—C6H4 | 4-Cl | Et | Et |
| 329 | 3 | 4-CF3—C6H4 | 4-Cl | Me | Me |
| 330 | 3 | 4-CF3—C6H4 | 4-Cl | Et | Et |
| 331 | 4 | C6H5 | H | Me | Me |
| 332 | 4 | C6H5 | H | Et | Et |
| 333 | 4 | 2-Me—C6H4 | H | Me | Me |
| 334 | 4 | 2-Me—C6H4 | H | Et | Et |
| 335 | 4 | 3-Me—C6H4 | H | Me | Me |
| 336 | 4 | 3-Me—C6H4 | H | Et | Et |
| 337 | 4 | 4-Me—C6H4 | H | Me | Me |
| 338 | 4 | 4-Me—C6H4 | H | Et | Et |
| 339 | 4 | 2-CF3—C6H4 | H | Me | Me |
| 340 | 4 | 2-CF3—C6H4 | H | Et | Et |
| 341 | 4 | 3-CF3—C6H4 | H | Me | Me |
| 342 | 4 | 3-CF3—C6H4 | H | Et | Et |
| 343 | 4 | 4-CF3—C6H4 | H | Me | Me |
| 344 | 4 | 4-CF3—C6H4 | H | Et | Et |
| 345 | 4 | 2-OMe—C6H4 | H | Me | Me |
| 346 | 4 | 2-OMe—C6H4 | H | Et | Et |
| 347 | 4 | 3-OMe—C6H4 | H | Me | Me |
| 348 | 4 | 3-OMe—C6H4 | H | Et | Et |
| 349 | 4 | 4-OMe—C6H4 | H | Me | Me |
| 350 | 4 | 4-OMe—C6H4 | H | Et | Et |
| 351 | 4 | 2-OCF3—C6H4 | H | Me | Me |
| 352 | 4 | 2-OCF3—C6H4 | H | Et | Et |
| 353 | 4 | 3-OCF3—C6H4 | H | Me | Me |
| 354 | 4 | 3-OCF3—C6H4 | H | Et | Et |
| 355 | 4 | 4-OCF3—C6H4 | H | Me | Me |
| 356 | 4 | 4-OCF3—C6H4 | H | Et | Et |
| 357 | 4 | 2-F—C6H4 | H | Me | Me |
| 358 | 4 | 2-F—C6H4 | H | Et | Et |
| 359 | 4 | 3-F—C6H4 | H | Me | Me |
| 360 | 4 | 3-F—C6H4 | H | Et | Et |
| 361 | 4 | 4-F—C6H4 | H | Me | Me |
| 362 | 4 | 4-F—C6H4 | H | Et | Et |
| 363 | 4 | 2-Br—C6H4 | H | Me | Me |
| 364 | 4 | 2-Br—C6H4 | H | Et | Et |
| 365 | 4 | 4-Br—C6H4 | H | Me | Me |
| 366 | 4 | 4-Br—C6H4 | H | Et | Et |
| 367 | 4 | 2,4-Cl2—C6H3 | H | Me | Me |
| 368 | 4 | 2,4-Cl2—C6H3 | H | Et | Et |
| 369 | 4 | 2-CN—C6H4 | H | Me | Me |
| 370 | 4 | 2-CN—C6H4 | H | Et | Et |
| 371 | 4 | 3-CN—C6H4 | H | Me | Me |
| 372 | 4 | 3-CN—C6H4 | H | Et | Et |
| 373 | 4 | 4-CN—C6H4 | H | Me | Me |
| 374 | 4 | 4-CN—C6H4 | H | Et | Et |
| 375 | 4 | 2-CO2Me—C6H4 | H | Me | Me |
| 376 | 4 | 2-CO2Me—C6H4 | H | Et | Et |
| 377 | 4 | 3-CO2Me—C6H4 | H | Me | Me |
| 378 | 4 | 3-CO2Me—C6H4 | H | Et | Et |
| 379 | 4 | 4-CO2Me—C6H4 | H | Me | Me |
| 380 | 4 | 4-CO2Me—C6H4 | H | Et | Et |

TABLE 1-2-continued

| No. | position of A'CH2 | R3 | Xn | R1 | R2 |
|---|---|---|---|---|---|
| 381 | 4 | 2-NO2—C6H4 | H | Me | Me |
| 382 | 4 | 2-NO2—C6H4 | H | Et | Et |
| 383 | 4 | 3-NO2—C6H4 | H | Me | Me |
| 384 | 4 | 3-NO2—C6H4 | H | Et | Et |
| 385 | 4 | 4-NO2—C6H4 | H | Me | Me |
| 386 | 4 | 4-NO2—C6H4 | H | Et | Et |
| 387 | 4 | 2-SO2Me—C6H4 | H | Me | Me |
| 388 | 4 | 2-SO2Me—C6H4 | H | Et | Et |
| 389 | 4 | 3-SO2Me—C6H4 | H | Me | Me |
| 390 | 4 | 3-SO2Me—C6H4 | H | Et | Et |
| 391 | 4 | 4-SO2Me—C6H4 | H | Me | Me |
| 392 | 4 | 4-SO2Me—C6H4 | H | Et | Et |
| 393 | 4 | 2-SMe—C6H4 | H | Me | Me |
| 394 | 4 | 2-SMe—C6H4 | H | Et | Et |
| 395 | 4 | 3-SMe—C6H4 | H | Me | Me |
| 396 | 4 | 3-SMe—C6H4 | H | Et | Et |
| 397 | 4 | 4-SMe—C6H4 | H | Me | Me |
| 398 | 4 | 4-SMe—C6H4 | H | Et | Et |
| 399 | 4 | 4-SOMe—C6H4 | H | Me | Me |
| 400 | 4 | 2-SOMe—C6H4 | H | Et | Et |
| 401 | 4 | 2,3-Cl2—C6H3 | H | Me | Me |
| 402 | 4 | 2,3-Cl2—C6H3 | H | Et | Et |
| 403 | 4 | 2,5-Cl2—C6H3 | H | Me | Me |
| 404 | 4 | 2,5-Cl2—C6H3 | H | Et | Et |
| 405 | 4 | 2,6-Cl2—C6H3 | H | Me | Me |
| 406 | 4 | 2,6-Cl2—C6H3 | H | Et | Et |
| 407 | 4 | 2,4,6-Cl3—C6H2 | H | Me | Me |
| 408 | 4 | 2,4,6-Cl3—C6H2 | H | Et | Et |
| 409 | 4 | 2-Cl,4-CO2Me—C6H3 | H | Me | Me |
| 410 | 4 | 2-Cl,4-CO2Me—C6H3 | H | Et | Et |
| 411 | 4 | 3-Cl,4-CO2Me—C6H3 | H | Me | Me |
| 412 | 4 | 3-Cl,4-CO2Me—C6H3 | H | Et | Et |
| 413 | 4 | 4-Cl,2-CO2Me—C6H3 | H | Me | Me |
| 414 | 4 | 4-Cl,2-CO2Me—C6H3 | H | Et | Et |
| 415 | 4 | 2-Cl,4-CF3—C6H3 | H | Me | Me |
| 416 | 4 | 2-Cl,4-CF3—C6H3 | H | Et | Et |
| 417 | 4 | C6F5 | H | Me | Me |
| 418 | 4 | C6F5 | H | Et | Et |
| 419 | 4 | 2-CN,4-Cl—C6H3 | H | Me | Me |
| 420 | 4 | 2-CN,4-Cl—C6H3 | H | Et | Et |
| 421 | 4 | 2-COMe—C6H4 | H | Me | Me |
| 422 | 4 | 2-COMe—C6H4 | H | Et | Et |
| 423 | 4 | 3-COMe—C6H4 | H | Me | Me |
| 424 | 4 | 3-COMe—C6H4 | H | Et | Et |
| 425 | 4 | 4-COMe—C6H4 | H | Me | Me |
| 426 | 4 | 4-COMe—C6H4 | H | Et | Et |
| 427 | 4 | 2,4-Cl2,3-Me—C6H2 | H | Me | Me |
| 428 | 4 | 2,4-Cl2,3-Me—C6H2 | H | Et | Et |
| 429 | 4 | 2,4,5-Cl3—C6H2 | H | Me | Me |
| 430 | 4 | 2,4,5-Cl3—C6H2 | H | Et | Et |
| 431 | 4 | C6H5 | 2,6-Cl2 | Me | Me |
| 432 | 4 | C6H5 | 2,6-Cl2 | Et | Et |
| 433 | 4 | 2-Me—C6H4 | 2,6-Cl2 | Me | Me |
| 434 | 4 | 2-Me—C6H4 | 2,6-Cl2 | Et | Et |
| 435 | 4 | 3-CF3—C6H4 | 2,6-Cl2 | Me | Me |
| 436 | 4 | 3-CF3—C6H4 | 2,6-Cl2 | Et | Et |
| 437 | 4 | 3-Me—C6H4 | 2,6-Cl2 | Me | Me |
| 438 | 4 | 3-Me—C6H4 | 2,6-Cl2 | Et | Et |
| 439 | 4 | 4-Me—C6H4 | 2,6-Cl2 | Me | Me |
| 440 | 4 | 4-Me—C6H4 | 2,6-Cl2 | Et | Et |
| 441 | 4 | 2-CF3—C6H4 | 2,6-Cl2 | Me | Me |
| 442 | 4 | 2-CF3—C6H4 | 2,6-Cl2 | Et | Et |
| 443 | 4 | 4-CF3—C6H4 | 2,6-Cl2 | Me | Me |
| 444 | 4 | 4-CF3—C6H4 | 2,6-Cl2 | Et | Et |
| 445 | 4 | 3-OMe—C6H4 | 2-CF3 | Me | Me |
| 446 | 4 | 3-OMe—C6H4 | 2-CF3 | Et | Et |
| 447 | 4 | 4-OMe—C6H4 | 2-CF3 | Me | Me |
| 448 | 4 | 4-OMe—C6H4 | 2-CF3 | Et | Et |
| 449 | 4 | 4-OCF3—C6H4 | 2-CF3 | Me | Me |
| 450 | 4 | 4-OCF3—C6H4 | 2-CF3 | Et | Et |
| 451 | 4 | C6H5 | 2-Cl | Me | Me |
| 452 | 4 | C6H5 | 2-Cl | Et | Et |
| 453 | 4 | 2-Me—C6H4 | 2-Cl | Me | Me |
| 454 | 4 | 2-Me—C6H4 | 2-Cl | Et | Et |
| 455 | 4 | 3-Me—C6H4 | 2-Cl | Me | Me |
| 456 | 4 | 3-Me—C6H4 | 2-Cl | Et | Et |

TABLE 1-2-continued

| No. | position of A'CH2 | R3 | Xn | R1 | R2 |
|---|---|---|---|---|---|
| 457 | 4 | 4-Me—C6H4 | 2-Cl | Me | Me |
| 458 | 4 | 4-Me—C6H4 | 2-Cl | Et | Et |
| 459 | 4 | 2-CF3—C6H4 | 2-Cl | Me | Me |
| 460 | 4 | 2-CF3—C6H4 | 2-Cl | Et | Et |
| 461 | 4 | 3-CF3—C6H4 | 2-Cl | Me | Me |
| 462 | 4 | 3-CF3—C6H4 | 2-Cl | Et | Et |
| 463 | 4 | 4-CF3—C6H4 | 2-Cl | Me | Me |
| 464 | 4 | 4-CF3—C6H4 | 2-Cl | Et | Et |
| 465 | 4 | 2-OMe—C6H4 | 2-Cl | Me | Me |
| 466 | 4 | 2-OMe—C6H4 | 2-Cl | Et | Et |
| 467 | 4 | 3-OMe—C6H4 | 2-Cl | Me | Me |
| 468 | 4 | 3-OMe—C6H4 | 2-Cl | Et | Et |
| 469 | 4 | 4-OMe—C6H4 | 2-Cl | Me | Me |
| 470 | 4 | 4-OMe—C6H4 | 2-Cl | Et | Et |
| 471 | 4 | 2-OCF3—C6H4 | 2-Cl | Me | Me |
| 472 | 4 | 2-OCF3—C6H4 | 2-Cl | Et | Et |
| 473 | 4 | 3-OCF3—C6H4 | 2-Cl | Me | Me |
| 474 | 4 | 3-OCF3—C6H4 | 2-Cl | Et | Et |
| 475 | 4 | 4-OCF3—C6H4 | 2-Cl | Me | Me |
| 476 | 4 | 4-OCF3—C6H4 | 2-Cl | Et | Et |
| 477 | 4 | 2-F—C6H4 | 2-Cl | Me | Me |
| 478 | 4 | 2-F—C6H4 | 2-Cl | Et | Et |
| 479 | 4 | 3-F—C6H4 | 2-Cl | Me | Me |
| 480 | 4 | 3-F—C6H4 | 2-Cl | Et | Et |
| 481 | 4 | 4-F—C6H4 | 2-Cl | Me | Me |
| 482 | 4 | 4-F—C6H4 | 2-Cl | Et | Et |
| 483 | 4 | 2-Br—C6H4 | 2-Cl | Me | Me |
| 484 | 4 | 2-Br—C6H4 | 2-Cl | Et | Et |
| 485 | 4 | 4-Br—C6H4 | 2-Cl | Me | Me |
| 486 | 4 | 4-Br—C6H4 | 2-Cl | Et | Et |
| 487 | 4 | 2,4-Cl2—C6H3 | 2-Cl | Me | Me |
| 488 | 4 | 2,4-Cl2—C6H3 | 2-Cl | Et | Et |
| 489 | 4 | 2-CN—C6H4 | 2-Cl | Me | Me |
| 490 | 4 | 2-CN—C6H4 | 2-Cl | Et | Et |
| 491 | 4 | 3-CN—C6H4 | 2-Cl | Me | Me |
| 492 | 4 | 3-CN—C6H4 | 2-Cl | Et | Et |
| 493 | 4 | 4-CN—C6H4 | 2-Cl | Me | Me |
| 494 | 4 | 4-CN—C6H4 | 2-Cl | Et | Et |
| 495 | 4 | 2-CO2Me—C6H4 | 2-Cl | Me | Me |
| 496 | 4 | 2-CO2Me—C6H4 | 2-Cl | Et | Et |
| 497 | 4 | 3-CO2Me—C6H4 | 2-Cl | Me | Me |
| 498 | 4 | 3-CO2Me—C6H4 | 2-Cl | Et | Et |
| 499 | 4 | 4-CO2Me—C6H4 | 2-Cl | Me | Me |
| 500 | 4 | 4-CO2Me—C6H4 | 2-Cl | Et | Et |
| 501 | 4 | 2-NO2—C6H4 | 2-Cl | Me | Me |
| 502 | 4 | 2-NO2—C6H4 | 2-Cl | Et | Et |
| 503 | 4 | 3-NO2—C6H4 | 2-Cl | Me | Me |
| 504 | 4 | 3-NO2—C6H4 | 2-Cl | Et | Et |
| 505 | 4 | 4-NO2—C6H4 | 2-Cl | Me | Me |
| 506 | 4 | 4-NO2—C6H4 | 2-Cl | Et | Et |
| 507 | 4 | 2-SO2Me—C6H4 | 2-Cl | Me | Me |
| 508 | 4 | 2-SO2Me—C6H4 | 2-Cl | Et | Et |
| 509 | 4 | 3-SO2Me—C6H4 | 2-Cl | Me | Me |
| 510 | 4 | 3-SO2Me—C6H4 | 2-Cl | Et | Et |
| 511 | 4 | 4-SO2Me—C6H4 | 2-Cl | Me | Me |
| 512 | 4 | 4-SO2Me—C6H4 | 2-Cl | Et | Et |
| 513 | 4 | 2-SMe—C6H4 | 2-Cl | Me | Me |
| 514 | 4 | 2-SMe—C6H4 | 2-Cl | Et | Et |
| 515 | 4 | 3-SMe—C6H4 | 2-Cl | Me | Me |
| 516 | 4 | 3-SMe—C6H4 | 2-Cl | Et | Et |
| 517 | 4 | 4-SMe—C6H4 | 2-Cl | Me | Me |
| 518 | 4 | 4-SMe—C6H4 | 2-Cl | Et | Et |
| 519 | 4 | 4-SOMe—C6H4 | 2-Cl | Me | Me |
| 520 | 4 | 2-SOMe—C6H4 | 2-Cl | Et | Et |
| 521 | 4 | 2,3-Cl2—C6H3 | 2-Cl | Me | Me |
| 522 | 4 | 2,3-Cl2—C6H3 | 2-Cl | Et | Et |
| 523 | 4 | 2,5-Cl2—C6H3 | 2-Cl | Me | Me |
| 524 | 4 | 2,5-Cl2—C6H3 | 2-Cl | Et | Et |
| 525 | 4 | 2,6-Cl2—C6H3 | 2-Cl | Me | Me |
| 526 | 4 | 2,6-Cl2—C6H3 | 2-Cl | Et | Et |
| 527 | 4 | 2,4,6-Cl3—C6H2 | 2-Cl | Me | Me |
| 528 | 4 | 2,4,6-Cl3—C6H2 | 2-Cl | Et | Et |
| 529 | 4 | 2-Cl,4-CO2Me—C6H3 | 2-Cl | Me | Me |
| 530 | 4 | 2-Cl,4-CO2Me—C6H3 | 2-Cl | Et | Et |
| 531 | 4 | 3-Cl,4-CO2Me—C6H3 | 2-Cl | Me | Me |
| 532 | 4 | 3-Cl,4-CO2Me—C6H3 | 2-Cl | Et | Et |

TABLE 1-2-continued

| No. | position of A'CH2 | R3 | Xn | R1 | R2 |
|---|---|---|---|---|---|
| 533 | 4 | 4-Cl,2-CO2Me—C6H3 | 2-Cl | Me | Me |
| 534 | 4 | 4-Cl,2-CO2Me—C6H3 | 2-Cl | Et | Et |
| 535 | 4 | 2-Cl,4-CF3—C6H3 | 2-Cl | Me | Me |
| 536 | 4 | 2-Cl,4-CF3—C6H3 | 2-Cl | Et | Et |
| 537 | 4 | C6F5 | 2-Cl | Me | Me |
| 538 | 4 | C6F5 | 2-Cl | Et | Et |
| 539 | 4 | 2-CN,4-Cl—C6H3 | 2-Cl | Me | Me |
| 540 | 4 | 2-CN,4-Cl—C6H3 | 2-Cl | Et | Et |
| 541 | 4 | 2-COMe—C6H4 | 2-Cl | Me | Me |
| 542 | 4 | 2-COMe—C6H4 | 2-Cl | Et | Et |
| 543 | 4 | 3-COMe—C6H4 | 2-Cl | Me | Me |
| 544 | 4 | 3-COMe—C6H4 | 2-Cl | Et | Et |
| 545 | 4 | 4-COMe—C6H4 | 2-Cl | Me | Me |
| 546 | 4 | 4-COMe—C6H4 | 2-Cl | Et | Et |
| 547 | 4 | 2,4-Cl2,3-Me—C6H2 | 2-Cl | Me | Me |
| 548 | 4 | 2,4-Cl2,3-Me—C6H2 | 2-Cl | Et | Et |
| 549 | 4 | 2,4,5-Cl3—C6H2 | 2-Cl | Me | Me |
| 550 | 4 | 2,4,5-Cl3—C6H2 | 2-Cl | Et | Et |
| 551 | 4 | C6H5 | 2-CF3 | Me | Me |
| 552 | 4 | C6H5 | 2-CF3 | Et | Et |
| 553 | 4 | 2-Me—C6H4 | 2-CF3 | Me | Me |
| 554 | 4 | 2-Me—C6H4 | 2-CF3 | Et | Et |
| 555 | 4 | 3-CF3—C6H4 | 2-CF3 | Me | Me |
| 556 | 4 | 3-CF3—C6H4 | 2-CF3 | Et | Et |
| 557 | 4 | 3-Me—C6H4 | 2-CF3 | Me | Me |
| 558 | 4 | 3-Me—C6H4 | 2-CF3 | Et | Et |
| 559 | 4 | 4-Me—C6H4 | 2-CF3 | Me | Me |
| 560 | 4 | 4-Me—C6H4 | 2-CF3 | Et | Et |
| 561 | 4 | 2-CF3—C6H4 | 2-CF3 | Me | Me |
| 562 | 4 | 2-CF3—C6H4 | 2-CF3 | Et | Et |
| 563 | 4 | 4-CF3—C6H4 | 2-CF3 | Me | Me |
| 564 | 4 | 4-CF3—C6H4 | 2-CF3 | Et | Et |
| 565 | 4 | 3-OMe—C6H4 | 2,6-Cl2 | Me | Me |
| 566 | 4 | 3-OMe—C6H4 | 2,6-Cl2 | Et | Et |
| 567 | 4 | 4-OMe—C6H4 | 2,6-Cl2 | Me | Me |
| 568 | 4 | 4-OMe—C6H4 | 2,6-Cl2 | Et | Et |
| 569 | 4 | 4-OCF3—C6H4 | 2,6-Cl2 | Me | Me |
| 570 | 4 | 4-OCF3—C6H4 | 2,6-Cl2 | Et | Et |
| 571 | 2 | Me | H | Me | Me |
| 572 | 2 | Et | H | Me | Me |
| 573 | 2 | n-Pr | H | Me | Me |
| 574 | 2 | i-Pr | H | Me | Me |
| 575 | 2 | c-Pr | H | Me | Me |
| 576 | 2 | n-Bu | H | Me | Me |
| 577 | 2 | i-Bu | H | Me | Me |
| 578 | 2 | s-Bu | H | Me | Me |
| 579 | 2 | t-Bu | H | Me | Me |
| 580 | 2 | c-Bu | H | Me | Me |
| 581 | 2 | c-Pen | H | Me | Me |
| 582 | 2 | c-Hex | H | Me | Me |
| 583 | 2 | CH2=CHCH2 | H | Me | Me |
| 584 | 2 | CH(Me)=CHCH2 | H | Me | Me |
| 585 | 2 | CHCCH2 | H | Me | Me |
| 586 | 2 | MeO2CCH2 | H | Me | Me |
| 587 | 2 | MeO2CCH(Me) | H | Me | Me |
| 588 | 2 | c-HexCH2 | H | Me | Me |
| 589 | 2 | Bn | H | Me | Me |
| 590 | 2 | 2-Me—C6H4CH2 | H | Me | Me |
| 591 | 2 | 3-Cl—C6H4CH(Me) | H | Me | Me |
| 592 | 2 | 4-CF3—C6H4CH2 | H | Me | Me |
| 593 | 2 | 2,4-Cl2—C6H3CH2 | H | Me | Me |
| 594 | 2 | 2-Pyridyl-CH2 | H | Me | Me |
| 595 | 2 | MeCO | H | Me | Me |
| 596 | 2 | EtCO | H | Me | Me |
| 597 | 2 | i-PrCO | H | Me | Me |
| 598 | 2 | c-PrCO | H | Me | Me |
| 599 | 2 | c-HexCO | H | Me | Me |
| 690 | 2 | PhCO | H | Me | Me |
| 601 | 2 | 4-Me—C6H4—CO | H | Me | Me |
| 602 | 2 | 3-F—C6H4—CO | H | Me | Me |
| 603 | 2 | 2-Cl—C6H4—CO | H | Me | Me |
| 604 | 2 | 3,5-Cl2—C6H3—CO | H | Me | Me |
| 605 | 2 | 2,4-Cl2-3-Me—C6H2CO | H | Me | Me |
| 606 | 2 | BnCO | H | Me | Me |
| 607 | 2 | 4-CF3—C6H4—CH2CO | H | Me | Me |
| 608 | 2 | 2-Me—C6H4CH2CO | H | Me | Me |

TABLE 1-2-continued

| No. | position of A'CH2 | R3 | Xn | R1 | R2 |
|---|---|---|---|---|---|
| 609 | 2 | PhCH(Me)CO | H | Me | Me |
| 610 | 2 | PhOCH2CO | H | Me | Me |
| 611 | 2 | PhOCH(Me)CO | H | Me | Me |
| 612 | 2 | PhSCH2CO | H | Me | Me |
| 613 | 2 | PhSCH(Me)CO | H | Me | Me |
| 614 | 2 | 2-CF3—C6H4OCH2CO | H | Me | Me |
| 615 | 2 | 3-Me—C6H4OCH2CO | H | Me | Me |
| 616 | 2 | 4-Cl—C6H4OCH2CO | H | Me | Me |
| 617 | 2 | 4-MeO—C6H4OCH(Me)CO | H | Me | Me |
| 618 | 2 | Pr | 4-Cl | Me | Me |
| 619 | 2 | MeCO | 4-Cl | Me | Me |
| 620 | 2 | EtCO | 4-Cl | Me | Me |
| 621 | 2 | c-PrCO | 4-Cl | Me | Me |
| 622 | 2 | PhCH2 | 4-Cl | Me | Me |
| 623 | 2 | PhOCH2 | 4-Cl | Me | Me |
| 624 | 2 | PhSCH2 | 4-Cl | Me | Me |
| 625 | 2 | Bn | 4-Cl | Me | Me |
| 626 | 2 | PhOCH(Me)CO | 4-Cl | Me | Me |
| 627 | 2 | PhCH2CH2 | 4-Cl | Me | Me |
| 628 | 2 | PhCH2CH2CO | 4-Br | Me | Me |
| 629 | 2 | 2-Pyridyl-OCH2CO | 4-Br | Me | Me |
| 630 | 2 | 2-Thienyl-CH2CO | 4-Br | Me | Me |
| 631 | 3 | Me | H | Me | Me |
| 632 | 3 | Et | H | Me | Me |
| 633 | 3 | i-Pr | H | Me | Me |
| 634 | 3 | n-Bu | H | Me | Me |
| 635 | 3 | c-Pr | 4-Cl | Me | Me |
| 636 | 3 | c-Pen | H | Me | Me |
| 637 | 3 | c-Hex | H | Me | Me |
| 638 | 3 | Bn | H | Me | Me |
| 639 | 3 | 2-Furyl-CH2 | H | Me | Me |
| 640 | 3 | i-PrCO | H | Me | Me |
| 641 | 3 | c-HexCO | H | Me | Me |
| 642 | 3 | 2,4-Cl2—C6H3CO | 4-NO2 | Me | Me |
| 643 | 3 | 2-Me—C6H4CH2CO | H | Me | Me |
| 644 | 3 | 4-CN—C6H4OCH2CO | H | Me | Me |
| 645 | 3 | 3-CF3—C6H4OCH(Me)CO | H | Et | Et |
| 646 | 3 | 5-CF3-2-Pyridyl-OCH2CO | H | Me | Me |
| 647 | 3 | CH2=CHCH2 | H | Me | Me |
| 648 | 3 | PhSCH(Me)CO | 4,6-Cl2 | Me | Me |
| 649 | 3 | t-BuCH2CO | H | Me | Me |
| 650 | 3 | 2-Thienyl-CH2 | H | Me | Me |
| 651 | 3 | 2,4-Cl2-3-Me—C6H2—OCH(Me)CO | H | Me | Me |
| 652 | 3 | MeOCH2CO | 4-Br | Me | Me |
| 653 | 3 | 4-MeO—C6H4—CH2 | H | Me | Me |
| 654 | 3 | 2-Me-4-Cl—C6H3—OCH(Me)CO | H | Me | Me |
| 655 | 3 | MeOCH2CH2CO | H | Me | Me |
| 656 | 3 | CHCCH2CO | H | Me | Me |
| 657 | 3 | 2-Cyclohexenyl-CO | H | Me | Me |
| 6S8 | 3 | 2-CN-4-Cl—C6H3OCH2CO | H | Me | Me |
| 659 | 3 | BnOCH2CH2 | H | Me | Me |
| 660 | 3 | 3,5-Cl2—C6H3—C(Me)2 | H | Me | Me |
| 661 | 4 | Me | H | Me | Me |
| 662 | 4 | Et | H | Me | Me |
| 663 | 4 | n-Pr | H | Me | Me |
| 664 | 4 | i-Pr | H | Me | Me |
| 665 | 4 | c-Pr | H | Me | Me |
| 666 | 4 | n-Bu | 2-CN | Me | Me |
| 667 | 4 | i-Bu | 2-CN | Me | Me |
| 668 | 4 | s-Bu | 2-CN | Et | Et |
| 669 | 4 | t-Bu | 2-CN | Me | Me |
| 670 | 4 | c-Bu | 2-CN | Me | Me |
| 671 | 4 | c-Pen | 2,5-Cl2 | Me | Me |
| 672 | 4 | c-Hex | 2,5-Cl2 | Me | Me |
| 673 | 4 | CH2=CHCH2 | 2,5-Cl2 | Me | Me |
| 674 | 4 | CH(Me)=CHCH2 | 2,5-Cl2 | Me | Me |
| 675 | 4 | CHCCH2 | 2,5-Cl2 | Me | Me |
| 676 | 4 | MeO2CCH2 | 2-CF3 | Me | Me |
| 677 | 4 | MeO2CCH(Me) | 2-CF3 | Me | Me |
| 678 | 4 | c-HexCH2 | 2-CF3 | Et | Et |
| 679 | 4 | Bn | 2-CF3 | Me | Me |
| 680 | 4 | 2-Me—C6H4CH2 | 2-CF3 | Me | Me |
| 681 | 4 | 3-Cl—C6H4CH(Me) | 2-CF3 | Me | Me |
| 682 | 4 | 4-CF3—C6H4CH2 | 2-CF3 | Me | Me |
| 683 | 4 | 2,4-Cl2—C6H3CH2 | 2-Me | Me | Me |
| 684 | 4 | 2-Pyridyl-CH2 | 2-Me | Me | Me |

TABLE 1-2-continued

| No. | position of A'CH2 | R3 | Xn | R1 | R2 |
|---|---|---|---|---|---|
| 685 | 4 | MeCO | 2-Me | Me | Me |
| 686 | 4 | EtCO | 2-Me | Me | Me |
| 687 | 4 | i-PrCO | 2-Me | Me | Me |
| 688 | 4 | c-PrCO | 2-Me | Me | Me |
| 689 | 4 | c-HexCO | 2-Me | Me | Me |
| 690 | 4 | PhCO | 2-Me | Me | Me |
| 691 | 4 | 4-Me—C6H4—CO | H | Me | Me |
| 692 | 4 | 3-F—C6H4—CO | H | Et | Et |
| 693 | 4 | 2-Cl—C6H4—CO | H | Me | Me |
| 694 | 4 | 3,5-Cl2—C6H3—CO | H | Me | Me |
| 695 | 4 | 2,4-Cl2-3-Me—C6H2CO | H | Me | Me |
| 696 | 4 | BnCO | H | Me | Me |
| 697 | 4 | 4-CF3—C6H4—CH2CO | 2-MeO | Me | Me |
| 698 | 4 | 2-Me—C6H4CH2CO | H | Me | Me |
| 699 | 4 | PhCH(Me)CO | H | Me | Me |
| 700 | 4 | PhOCH2CO | H | Me | Me |
| 701 | 4 | PhOCH(Me)CO | H | Me | Me |
| 702 | 4 | PhSCH2CO | H | Me | Me |
| 703 | 4 | PhSCH(Me)CO | H | Me | Me |
| 704 | 4 | 2-CF3—C6H4OCH2CO | H | Me | Me |
| 705 | 4 | 3-Me—C6H4OCH2CO | H | Me | Me |
| 706 | 4 | 4-Cl—C6H4OCH2CO | H | Me | Me |
| 707 | 4 | 4-MeO—C6H4OCH(Me)CO | H | Me | Me |
| 708 | 4 | Pr | 2-Cl | Me | Me |
| 709 | 4 | c-Hex | 2-Cl | Me | Me |
| 710 | 4 | EtCO | 2-NO2 | Me | Me |
| 711 | 4 | c-PrCO | 2-Br | Me | Me |
| 712 | 4 | PhCH2 | 2-NO2 | Me | Me |
| 713 | 4 | PhOCH2 | 2,6-Cl2 | Me | Me |
| 714 | 4 | 2-Me-4-Cl—C6H3—OCH(Me)CO | H | Me | Me |
| 715 | 4 | MeOCH2CH2CO | H | Me | Me |
| 716 | 4 | CHCCH2CO | H | Me | Me |
| 717 | 4 | 2-Cyclohexenyl-CO | H | Me | Me |
| 718 | 4 | 2-CN-4-Cl—C6H3OCH2CO | H | Me | Me |
| 719 | 4 | BnOCH2CH2 | H | Me | Me |
| 720 | 4 | 3,5-Cl2—C6H3—C(Me)2 | H | Me | Me |
| 721 | 2 | c-Hex | 4-Cl | Me | Me |
| 722 | 2 | 4-OMe—C6H4CH2 | 4-Cl | Me | Me |
| 723 | 2 | 3-F—C6H4 | 4-Cl | Me | Me |
| 724 | 2 | 2-thienyl | 4-Cl | Me | Me |
| 725 | 2 | Et | 4-Cl | Me | Me |
| 726 | 2 | Me | 4-Cl | Me | Me |
| 727 | 2 | n-Bu | 4-Cl | Me | Me |

TABLE 1-3

| No. | position of ACH2 | R4 | R5 | Xn | R1 | R2 |
|---|---|---|---|---|---|---|
| 1 | 2 | H | Me | H | Me | Me |
| 2 | 2 | H | Et | H | Me | Me |
| 3 | 2 | H | n-Pr | H | Me | Me |
| 4 | 2 | H | i-Pr | H | Me | Me |
| 5 | 2 | H | n-Bu | H | Me | Me |
| 6 | 2 | H | s-Bu | H | Me | Me |
| 7 | 2 | H | t-Bu | H | Me | Me |
| 8 | 2 | H | c-Pr | H | Me | Me |
| 9 | 2 | H | c-Pen | H | Me | Me |
| 10 | 2 | H | c-Hex | H | Me | Me |
| 11 | 2 | H | CH2CH=CH2 | H | Me | Me |
| 12 | 2 | H | CH2CCH | H | Me | Me |
| 13 | 2 | H | Ph | H | Me | Me |
| 14 | 2 | H | 2-Cl—C6H4 | 4-Cl | Me | Me |
| 15 | 2 | H | 3-Cl—C6H4 | H | Me | Me |
| 16 | 2 | H | 4-Cl—C6H4 | H | Me | Me |
| 17 | 2 | H | 2-Me—C6H4 | H | Me | Me |
| 18 | 2 | H | 3-Me—C6H4 | 6-Cl | Me | Me |
| 19 | 2 | H | 4-Me—C6H4 | H | Me | Me |
| 20 | 2 | H | 2-CF3—C6H4 | H | Me | Me |
| 21 | 2 | H | 3-CF3—C6H4 | H | Me | Me |
| 22 | 2 | H | 4-CF3—C6H4 | H | Me | Me |
| 23 | 2 | H | 2-OCF3—C6H4 | 4-MeO | Me | Me |
| 24 | 2 | H | 3-OCF3—C6H4 | H | Me | Me |

TABLE 1-3-continued

| No. | position of ACH2 | R4 | R5 | Xn | R1 | R2 |
|---|---|---|---|---|---|---|
| 25 | 2 | H | 4-OCF3—C6H4 | H | Me | Me |
| 26 | 2 | H | 2-OMe—C6H4 | H | Me | Me |
| 27 | 2 | H | 3-OMe—C6H4 | H | Me | Me |
| 28 | 2 | H | 4-OMe—C6H4 | H | Me | Me |
| 29 | 2 | H | 2-CN—C6H4 | H | Me | Me |
| 30 | 2 | H | 3-CO2Me—C6H4 | H | Me | Me |
| 31 | 2 | H | Bn | H | Me | Me |
| 32 | 2 | H | 2-Cl—C6H4—CH2 | H | Me | Me |
| 33 | 2 | H | 3-Cl—C6H4—CH2 | H | Me | Me |
| 34 | 2 | H | 4-Cl—C6H4—CH2 | H | Me | Me |
| 35 | 2 | H | 2-Me—C6H4—CH2 | 4-Cl | Me | Me |
| 36 | 2 | H | 3-OMe—C6H4—CH2 | H | Me | Me |
| 37 | 2 | H | 4-Me—C6H4—CH2 | H | Me | Me |
| 38 | 2 | H | 2-CF3—C6H4—CH2 | H | Me | Me |
| 39 | 2 | H | 3-CF3—C6H4—CH2 | H | Me | Me |
| 40 | 2 | H | 4-CF3—C6H4—CH2 | H | Me | Me |
| 41 | 2 | H | 2-Pyridyl | H | Me | Me |
| 42 | 2 | H | 3-Pyridyl | H | Me | Me |
| 43 | 2 | H | 4-Pyridyl | H | Me | Me |
| 44 | 2 | H | 2-Thienyl | H | Me | Me |
| 45 | 2 | H | 3-Thienyl | H | Me | Me |
| 46 | 2 | H | 2-Furyl | 4-Cl | Me | Me |
| 47 | 2 | H | PhO | H | Me | Me |
| 48 | 2 | H | 2-Cl—C6H4—O | H | Me | Me |
| 49 | 2 | H | 3-Me—C6H4—O | H | Me | Me |
| 50 | 2 | H | 2,4-Cl2—C6H3—O | H | Me | Me |
| 51 | 2 | H | BnO | H | Me | Me |
| 52 | 2 | H | 4-Me—C6H4—CH2O | H | Me | Me |
| 53 | 2 | H | 2-Me—C6H4—CH2O | H | Me | Me |
| 54 | 2 | H | 3-CF3—C6H4—CH2O | 4-Cl | Me | Me |
| 55 | 2 | H | 4-CF3—C6H4—CH2O | H | Me | Me |
| 56 | 2 | H | PhOCH2 | H | Me | Me |
| 57 | 2 | H | 2,4-Cl2—C6H3OCH2 | H | Me | Me |
| 58 | 2 | H | 4-PhO—C6H4 | H | Me | Me |
| 59 | 2 | H | BnO | H | Et | Et |
| 60 | 2 | H | 4-Me—C6H4—CH2O | H | Et | Et |
| 61 | 2 | Me | Me | 4-Cl | Me | Me |
| 62 | 2 | Me | i-Pr | H | Me | Me |
| 63 | 2 | Me | i-Bu | H | Me | Me |
| 64 | 2 | Me | c-Hex | H | Me | Me |
| 65 | 2 | Me | Ph | H | Me | Me |
| 66 | 2 | Me | 2-Cl—C6H4 | H | Me | Me |
| 67 | 2 | Me | 3-Cl—C6H4 | H | Me | Me |
| 68 | 2 | Me | 4-Cl—C6H4 | H | Me | Me |
| 69 | 2 | Me | 2-Me—C6H4 | H | Me | Me |
| 70 | 2 | Me | 3-Me—C6H4 | H | Me | Me |
| 71 | 2 | Me | 4-Cl—C6H4 | 4-Cl | Me | Me |
| 72 | 2 | Me | 2-CF3—C6H4 | H | Me | Me |
| 73 | 2 | Me | 3-CF3—C6H4 | H | Me | Me |
| 74 | 2 | Me | 4-CF3—C6H4 | H | Me | Me |
| 75 | 2 | Me | 2-OCF3—C6H4 | H | Me | Me |
| 76 | 2 | Me | 3-OCF3—C6H4 | H | Me | Me |
| 77 | 2 | Me | 4-OCF3—C6H4 | H | Me | Me |
| 78 | 2 | Me | 2-OMe—C6H4 | H | Me | Me |
| 79 | 2 | Me | 3-OMe—C6H4 | H | Me | Me |
| 80 | 2 | Me | 2,4-Cl2—C6H3 | 4-F | Me | Me |
| 81 | 2 | Me | 2-Br—C6H4 | H | Me | Me |
| 82 | 2 | Me | 3-Br—C6H4 | H | Me | Me |
| 83 | 2 | Me | 4-Br—C6H4 | H | Me | Me |
| 84 | 2 | Me | Bn | H | Me | Me |
| 85 | 2 | Me | 4-Cl—C6H4CH2 | H | Me | Me |
| 86 | 2 | Me | 2-Me—C6H4CH2 | H | Me | Me |
| 87 | 2 | Me | 3-CF3—C6H4CH2 | 4-CF3O | Me | Me |
| 88 | 2 | Me | PhCHMe | H | Me | Me |
| 89 | 2 | Me | PhCH2CH2 | H | Me | Me |
| 90 | 2 | Me | 4-EtO-2-Pyrimidyl | H | Me | Me |
| 91 | 2 | Me | 2—Pyrimidyl | H | Me | Me |
| 92 | 2 | Me | 4—Pyrimidyl | H | Me | Me |
| 93 | 2 | Me | 2-Pyridyl | H | Me | Me |
| 94 | 2 | Me | 3-Pyridyl | H | Me | Me |
| 95 | 2 | Me | 4-Pyridyl | H | Me | Me |
| 96 | 2 | Me | 2-Thienyl | H | Me | Me |
| 97 | 2 | Me | 3-Thienyl | H | Me | Me |
| 98 | 2 | Me | 2-Furyl | H | Me | Me |
| 99 | 2 | Me | BnO | H | Me | Me |
| 100 | 2 | Me | 2-Me—C6H4CH2 | H | Me | Me |

TABLE 1-3-continued

| No. | position of ACH2 | R4 | R5 | Xn | R1 | R2 |
|---|---|---|---|---|---|---|
| 101 | 2 | Me | 3-Me—C6H4CH2 | H | Me | Me |
| 102 | 2 | Me | 4-Me—C6H4CH2 | 5-Cl | Me | Me |
| 103 | 2 | Me | 2-CF3—C6H4CH2 | H | Me | Me |
| 104 | 2 | Me | 3-CF3—C6H4CH2 | H | Me | Me |
| 105 | 2 | Me | 4-CF3—C6H4CH2 | H | Me | Me |
| 106 | 2 | Me | 2-OMe—C6H4CH2 | H | Me | Me |
| 107 | 2 | Me | BnO | 4-Cl | Me | Me |
| 108 | 2 | Me | 4-OMe—C6H4CH2 | H | Me | Me |
| 109 | 2 | Me | 2-Cl—C6H4CH2 | H | Me | Me |
| 110 | 2 | Me | 3-Cl—C6H4CH2 | H | Me | Me |
| 111 | 2 | Me | 4-Cl—C6H4CH2 | H | Me | Me |
| 112 | 2 | Me | BnS | H | Me | Me |
| 113 | 2 | Me | PhO | 4-Cl | Me | Me |
| 114 | 2 | Me | PhS | H | Me | Me |
| 115 | 2 | Me | EtO | H | Me | Me |
| 116 | 2 | Me | EtS | H | Me | Me |
| 117 | 2 | Me | CH2=CHCH2O | H | Me | Me |
| 118 | 2 | Me | 2,4-Cl2—C6H3CH2O | H | Me | Me |
| 119 | 2 | Me | 2,4-Cl2—C6H3CH2 | H | Me | Me |
| 120 | 2 | Me | PhCHMe | H | Me | Me |
| 121 | 2 | CN | Ph | H | Me | Me |
| 122 | 2 | CN | 2-Cl—C6H4 | H | Me | Me |
| 123 | 2 | CN | 3-Cl—C6H4 | H | Me | Me |
| 124 | 2 | CN | 4-Cl—C6H4 | H | Me | Me |
| 125 | 2 | CN | 2-Me—C6H4 | H | Me | Me |
| 126 | 2 | CN | 3-Me—C6H4 | H | Me | Me |
| 127 | 2 | CN | 4-Me—C6H4 | H | Me | Me |
| 128 | 2 | CN | 2-CF3—C6H4 | 4-CF3 | Me | Me |
| 129 | 2 | CN | 3-CF3—C6H4 | H | Me | Me |
| 130 | 2 | CN | 4-CF3—C6H4 | H | Me | Me |
| 131 | 2 | CN | 2-OCF3—C6H4 | H | Me | Me |
| 132 | 2 | CN | 3-OCF3—C6H4 | H | Me | Me |
| 133 | 2 | CN | 4-OCF3—C6H4 | H | Me | Me |
| 134 | 2 | CN | 2-OMe—C6H4 | 4-OMe | Me | Me |
| 135 | 2 | CN | 3-OMe—C6H4 | H | Me | Me |
| 136 | 2 | CN | 2,4-Cl2—C6H3 | H | Me | Me |
| 137 | 2 | CN | 2-Br—C6H4 | H | Me | Me |
| 138 | 2 | CN | 3-Br—C6H4 | H | Me | Me |
| 139 | 2 | CN | 4-Br—C6H4 | 4-Cl | Me | Me |
| 140 | 2 | CN | 4-CO2Me—C6H4 | H | Me | Me |
| 141 | 2 | CN | 4-CN—C6H4 | H | Me | Me |
| 142 | 2 | CN | 2-CN—C6H4 | H | Me | Me |
| 143 | 2 | Et | Ph | H | Me | Me |
| 144 | 2 | Et | Bn | H | Me | Me |
| 145 | 2 | Et | PhO | 4,6-Cl2 | Me | Me |
| 146 | 2 | Et | BnO | H | Me | Me |
| 147 | 2 | Et | PhS | H | Me | Me |
| 148 | 2 | Et | BnS | H | Me | Me |
| 149 | 2 | Et | PhCHMeO | H | Me | Me |
| 150 | 2 | Et | Et | H | Me | Me |
| 151 | 2 | Et | 4-Pyrimidyl | H | Me | Me |
| 152 | 2 | Et | 2-Thienyl | H | Me | Me |
| 153 | 2 | Et | 2-Pyrimidyl | H | Me | Me |
| 154 | 2 | c-Pr | Ph | H | Me | Me |
| 155 | 2 | c-Pr | Bn | H | Me | Me |
| 156 | 2 | c-Pr | PhO | H | Me | Me |
| 157 | 2 | c-Pr | BnO | 4-Cl | Me | Me |
| 158 | 2 | c-Pr | PhS | H | Me | Me |
| 159 | 2 | c-Pr | BnS | H | Me | Me |
| 160 | 2 | c-Pr | PhCHMeO | H | Me | Me |
| 161 | 2 | c-Pr | Et | 3-Cl | Me | Me |
| 162 | 2 | c-Pr | 2-Pyrimidyl | H | Me | Me |
| 163 | 2 | c-Pr | 2-Thienyl | H | Me | Me |
| 164 | 2 | c-Pr | 2-Pyrimidyl | H | Me | Me |
| 165 | 2 | CH2=CHCH2 | CH2=CHCH2 | H | Me | Me |
| 166 | 2 | CH2=CHCH2 | Ph | H | Me | Me |
| 167 | 2 | CH2=CHCH2 | 4-OMe—C6H4 | H | Me | Me |
| 168 | 2 | CH2=CHCH2 | 4-Me—C6H4 | H | Me | Me |
| 169 | 2 | Ph | Ph | 4-Cl | Me | Me |
| 170 | 2 | Ph | Bn | H | Me | Me |
| 171 | 2 | Ph | PhO | H | Me | Me |
| 172 | 2 | Ph | BnO | H | Me | Me |
| 173 | 2 | Ph | PhS | H | Me | Me |
| 174 | 2 | Ph | BnS | H | Me | Me |
| 175 | 2 | Ph | MeO | H | Me | Me |
| 176 | 2 | Ph | EtO | H | Me | Me |

TABLE 1-3-continued

| No. | position of ACH2 | R4 | R5 | Xn | R1 | R2 |
|---|---|---|---|---|---|---|
| 177 | 2 | Ph | i-PrO | H | Me | Me |
| 178 | 2 | Ph | EtS | 4-F | Me | Me |
| 179 | 2 | Ph | CH2=CHCH2O | H | Me | Me |
| 180 | 2 | Ph | PhCH2CH2O | H | Me | Me |
| 181 | 3 | H | Me | H | Me | Me |
| 182 | 3 | H | Et | H | Me | Me |
| 183 | 3 | H | n-Pr | H | Me | Me |
| 184 | 3 | H | i-Pr | H | Me | Me |
| 185 | 3 | H | n-Bu | H | Me | Me |
| 186 | 3 | H | s-Bu | H | Me | Me |
| 187 | 3 | H | t-Bu | H | Me | Me |
| 188 | 3 | H | c-Pr | H | Me | Me |
| 189 | 3 | H | c-Pen | H | Me | Me |
| 190 | 3 | H | c-Hex | H | Me | Me |
| 191 | 3 | H | CH2CH=CH2 | H | Me | Me |
| 192 | 3 | H | CH2CCH | H | Me | Me |
| 193 | 3 | H | Ph | H | Me | Me |
| 194 | 3 | H | 2-Cl—C6H4 | H | Me | Me |
| 195 | 3 | H | 3-Cl—C6H4 | H | Me | Me |
| 196 | 3 | H | 4-Cl—C6H4 | H | Me | Me |
| 197 | 3 | H | 2-Me—C6H4 | H | Me | Me |
| 198 | 3 | H | 3-Me—C6H4 | H | Me | Me |
| 199 | 3 | H | 4-Me—C6H4 | H | Me | Me |
| 200 | 3 | H | 2-CF3—C6H4 | H | Me | Me |
| 201 | 3 | H | 3-CF3—C6H4 | H | Me | Me |
| 202 | 3 | H | 4-CF3—C6H4 | H | Me | Me |
| 203 | 3 | H | 2-OCF3—C6H4 | H | Me | Me |
| 204 | 3 | H | 3-OCF3—C6H4 | H | Me | Me |
| 205 | 3 | H | 4-OCF3—C6H4 | H | Me | Me |
| 206 | 3 | H | 2-OMe—C6H4 | H | Me | Me |
| 207 | 3 | H | 3-OMe—C6H4 | H | Me | Me |
| 208 | 3 | H | 4-OMe—C6H4 | H | Me | Me |
| 209 | 3 | H | 2-CN—C6H4 | H | Me | Me |
| 210 | 3 | H | 3-CO2Me—C6H4 | H | Me | Me |
| 211 | 3 | H | Bn | H | Me | Me |
| 212 | 3 | H | 2-Cl—C6H4—CH2 | H | Me | Me |
| 213 | 3 | H | 3-Cl—C6H4—CH2 | H | Me | Me |
| 214 | 3 | H | 4-Cl—C6H4—CH2 | H | Me | Me |
| 215 | 3 | H | 2-Me—C6H4—CH2 | H | Me | Me |
| 216 | 3 | H | 3-OMe—C6H4—CH2 | H | Me | Me |
| 217 | 3 | H | 4-Me—C6H4—CH2 | H | Me | Me |
| 218 | 3 | H | 2-CF3—C6H4—CH2 | H | Me | Me |
| 219 | 3 | H | 3-CF3—C6H4—CH2 | H | Me | Me |
| 220 | 3 | H | 4-CF3—C6H4—CH2 | H | Me | Me |
| 221 | 3 | H | 2-Pyridyl | H | Me | Me |
| 222 | 3 | H | 3-Pyridyl | H | Me | Me |
| 223 | 3 | H | 4-Pyridyl | H | Me | Me |
| 224 | 3 | H | 2-Thienyl | H | Me | Me |
| 225 | 3 | H | 3-Thienyl | H | Me | Me |
| 226 | 3 | H | 2-Furyl | H | Me | Me |
| 227 | 3 | H | PhO | H | Me | Me |
| 228 | 3 | H | 2-Cl—C6H4—O | H | Me | Me |
| 229 | 3 | H | 3-Me—C6H4—O | H | Me | Me |
| 230 | 3 | H | 2,4-Cl2—C6H3—O | H | Me | Me |
| 231 | 3 | H | BnO | H | Me | Me |
| 232 | 3 | H | 4-Me—C6H4—CH2O | H | Me | Me |
| 233 | 3 | H | 2-Me—C6H4—CH2O | H | Me | Me |
| 234 | 3 | H | 3-CF3—C6H4—CH2O | H | Me | Me |
| 235 | 3 | H | 4-CF3—C6H4—CH2O | H | Me | Me |
| 236 | 3 | H | PhOCH2 | H | Me | Me |
| 237 | 3 | H | 2,4-Cl2—C6H3OCH2 | H | Me | Me |
| 238 | 3 | H | 4-PhO—C6H4 | H | Me | Me |
| 239 | 3 | H | BnO | H | Et | Et |
| 240 | 3 | H | BnO | 4-Cl | Me | Me |
| 241 | 3 | Me | Me | H | Me | Me |
| 242 | 3 | Me | i-Pr | H | Me | Me |
| 243 | 3 | Me | i-Bu | H | Me | Me |
| 244 | 3 | Me | c-Hex | H | Me | Me |
| 245 | 3 | Me | Ph | H | Me | Me |
| 246 | 3 | Me | 2-Cl—C6H4 | H | Me | Me |
| 247 | 3 | Me | 3-Cl—C6H4 | H | Me | Me |
| 248 | 3 | Me | 4-Cl—C6H4 | H | Me | Me |
| 249 | 3 | Me | 2-Me—C6H4 | H | Me | Me |
| 250 | 3 | Me | 3-Me—C6H4 | H | Me | Me |
| 251 | 3 | Me | 4-Me—C6H4 | H | Me | Me |
| 252 | 3 | Me | 2-CF3—C6H4 | H | Me | Me |

TABLE 1-3-continued

| No. | position of ACH2 | R4 | R5 | Xn | R1 | R2 |
|---|---|---|---|---|---|---|
| 253 | 3 | Me | 3-CF3—C6H4 | H | Me | Me |
| 254 | 3 | Me | 4-CF3—C6H4 | H | Me | Me |
| 255 | 3 | Me | 2-OCF3—C6H4 | H | Me | Me |
| 256 | 3 | Me | 3-OCF3—C6H4 | H | Me | Me |
| 257 | 3 | Me | 4-OCF3—C6H4 | H | Me | Me |
| 258 | 3 | Me | 2-OMe—C6H4 | H | Me | Me |
| 259 | 3 | Me | 3-OMe—C6H4 | H | Me | Me |
| 260 | 3 | Me | 2,4-Cl2—C6H3 | H | Me | Me |
| 261 | 3 | Me | 2-Br—C6H4 | H | Me | Me |
| 262 | 3 | Me | 3-Br—C6H4 | H | Me | Me |
| 263 | 3 | Me | 4-Br—C6H4 | H | Me | Me |
| 264 | 3 | Me | Bn | H | Me | Me |
| 265 | 3 | Me | 4-Cl—C6H4CH2 | H | Me | Me |
| 266 | 3 | Me | 2-Me—C6H4CH2 | H | Me | Me |
| 267 | 3 | Me | 3-CF3—C6H4CH2 | H | Me | Me |
| 268 | 3 | Me | PhCHMe | H | Me | Me |
| 269 | 3 | Me | PhCH2CH2 | H | Me | Me |
| 270 | 3 | Me | 4-EtO-2-Pyrimidyl | H | Me | Me |
| 271 | 3 | Me | 2-Pyrimidyl | H | Me | Me |
| 272 | 3 | Me | 4-Pyrimidyl | H | Me | Me |
| 273 | 3 | Me | 2-Pyridyl | H | Me | Me |
| 274 | 3 | Me | 3-Pyridyl | H | Me | Me |
| 275 | 3 | Me | 4-Pyridyl | H | Me | Me |
| 276 | 3 | Me | 2-Thienyl | H | Me | Me |
| 277 | 3 | Me | 3-Thienyl | H | Me | Me |
| 278 | 3 | Me | 2-Furyl | H | Me | Me |
| 279 | 3 | Me | BnO | H | Me | Me |
| 280 | 3 | Me | 2-Me—C6H4CH2 | H | Me | Me |
| 281 | 3 | Me | 3-Me—C6H4CH2 | H | Me | Me |
| 282 | 3 | Me | 4-Me—C6H4CH2 | H | Me | Me |
| 283 | 3 | Me | 2-CF3—C6H4CH2 | H | Me | Me |
| 284 | 3 | Me | 3-CF3—C6H4CH2 | H | Me | Me |
| 285 | 3 | Me | 4-CF3—C6H4CH2 | H | Me | Me |
| 286 | 3 | Me | 2-OMe—C6H4CH2 | H | Me | Me |
| 287 | 3 | Me | 3-OMe—C6H4CM2 | H | Me | Me |
| 288 | 3 | Me | 4-OMe—C6H4CH2 | H | Me | Me |
| 289 | 3 | Me | 2-Cl—C6H4CH2 | H | Me | Me |
| 290 | 3 | Me | 3-Cl—C6H4CH2 | H | Me | Me |
| 291 | 3 | Me | 4-Cl—C6H4CH2 | H | Me | Me |
| 292 | 3 | Me | BnS | H | Me | Me |
| 293 | 3 | Me | PhO | H | Me | Me |
| 294 | 3 | Me | PhS | H | Me | Me |
| 295 | 3 | Me | EtO | H | Me | Me |
| 296 | 3 | Me | EtS | H | Me | Me |
| 297 | 3 | Me | CH2=CHCH2O | H | Me | Me |
| 298 | 3 | Me | 2,4-Cl2—C6H3CH2O | H | Me | Me |
| 299 | 3 | Me | 2,4-Cl2—C6H3CH2 | H | Me | Me |
| 300 | 3 | Me | PhCHMe | H | Me | Me |
| 301 | 3 | CN | Ph | H | Me | Me |
| 302 | 3 | CN | 2-Cl—C6H4 | H | Me | Me |
| 303 | 3 | CN | 3-Cl—C6H4 | H | Me | Me |
| 304 | 3 | CN | 4-Cl—C6H4 | H | Me | Me |
| 305 | 3 | CN | 2-Me—C6H4 | H | Me | Me |
| 306 | 3 | CN | 3-Me—C6H4 | H | Me | Me |
| 307 | 3 | CN | 4-Me—C6H4 | H | Me | Me |
| 308 | 3 | CN | 2-CF3—C6H4 | H | Me | Me |
| 309 | 3 | CN | 3-CF3—C6H4 | H | Me | Me |
| 310 | 3 | CN | 4-CF3—C6H4 | H | Me | Me |
| 311 | 3 | CN | 2-OCF3—C6H4 | H | Me | Me |
| 312 | 3 | CN | 3-OCF3—C6H4 | H | Me | Me |
| 313 | 3 | CN | 4-OCF3—C6H4 | H | Me | Me |
| 314 | 3 | CN | 2-OMe—C6H4 | H | Me | Me |
| 315 | 3 | CN | 3-OMe—C6H4 | H | Me | Me |
| 316 | 3 | CN | 2,4-Cl2—C6H3 | H | Me | Me |
| 317 | 3 | CN | 2-Br—C6H4 | H | Me | Me |
| 318 | 3 | CN | 3-Br—C6H4 | H | Me | Me |
| 319 | 3 | CN | 4-Br—C6H4 | H | Me | Me |
| 320 | 3 | CN | 4-CO2Me—C6H4 | H | Me | Me |
| 321 | 3 | CN | 4-CN—C6H4 | H | Me | Me |
| 322 | 3 | CN | 2-CN—C6H4 | H | Me | Me |
| 323 | 3 | Et | Ph | H | Me | Me |
| 324 | 3 | Et | Bn | H | Me | Me |
| 325 | 3 | Et | PhO | H | Me | Me |
| 326 | 3 | Et | BnO | H | Me | Me |
| 327 | 3 | Et | PhS | H | Me | Me |
| 328 | 3 | Et | BnS | H | Me | Me |

TABLE 1-3-continued

| No. | position of ACH2 | R4 | R5 | Xn | R1 | R2 |
|---|---|---|---|---|---|---|
| 329 | 3 | Et | PhCHMeO | H | Me | Me |
| 330 | 3 | Et | Et | H | Me | Me |
| 331 | 3 | Et | 4-Pyrimidyl | H | Me | Me |
| 332 | 3 | Et | 2-Thienyl | H | Me | Me |
| 333 | 3 | Et | 2-Pyrimidyl | H | Me | Me |
| 334 | 3 | c-Pr | Ph | H | Me | Me |
| 335 | 3 | c-Pr | Bn | H | Me | Me |
| 336 | 3 | c-Pr | PhO | H | Me | Me |
| 337 | 3 | c-Pr | BnO | H | Me | Me |
| 338 | 3 | c-Pr | PhS | H | Me | Me |
| 339 | 3 | c-Pr | BnS | H | Me | Me |
| 340 | 3 | c-Pr | PhCHMeO | H | Me | Me |
| 341 | 3 | c-Pr | Et | H | Me | Me |
| 342 | 3 | c-Pr | 2-Pyrimidyl | H | Me | Me |
| 343 | 3 | c-Pr | 2-Thienyl | H | Me | Me |
| 344 | 3 | c-Pr | 2-Pyrimidyl | H | Me | Me |
| 345 | 3 | CH2=CHCH2 | CH2=CHCH2 | H | Me | Me |
| 346 | 3 | CH2=CHCH2 | Ph | H | Me | Me |
| 347 | 3 | CH2=CHCH2 | 4-OMe—C6H4 | H | Me | Me |
| 348 | 3 | CH2=CHCH2 | 4-Me—C6H4 | H | Me | Me |
| 349 | 3 | Ph | Ph | H | Me | Me |
| 350 | 3 | Ph | Bn | H | Me | Me |
| 351 | 3 | Ph | PhO | H | Me | Me |
| 352 | 3 | Ph | BnO | H | Me | Me |
| 353 | 3 | Ph | PhS | H | Me | Me |
| 354 | 3 | Ph | BnS | H | Me | Me |
| 355 | 3 | Ph | MeO | H | Me | Me |
| 356 | 3 | Ph | EtO | H | Me | Me |
| 357 | 3 | Ph | i-PrO | H | Me | Me |
| 358 | 3 | Ph | EtS | H | Me | Me |
| 359 | 3 | Ph | CH2=CHCH2O | H | Me | Me |
| 360 | 3 | Ph | PhCH2CH2O | H | Me | Me |
| 361 | 4 | H | Me | H | Me | Me |
| 362 | 4 | H | Et | H | Me | Me |
| 363 | 4 | H | n-Pr | H | Me | Me |
| 364 | 4 | H | i-Pr | H | Me | Me |
| 365 | 4 | H | n-Bu | H | Me | Me |
| 366 | 4 | H | s-Bu | H | Me | Me |
| 367 | 4 | H | t-Bu | H | Me | Me |
| 368 | 4 | H | c-Pr | H | Me | Me |
| 369 | 4 | H | c-Pen | H | Me | Me |
| 370 | 4 | H | c-Hex | H | Me | Me |
| 371 | 4 | H | CH2CH=CH2 | H | Me | Me |
| 372 | 4 | H | CH2CCH | H | Me | Me |
| 373 | 4 | H | Ph | H | Me | Me |
| 374 | 4 | H | 2-Cl—C6H4 | H | Me | Me |
| 375 | 4 | H | 3-Cl—C6H4 | H | Me | Me |
| 376 | 4 | H | 4-Cl—C6H4 | H | Me | Me |
| 377 | 4 | H | 2-Me—C6H4 | H | Me | Me |
| 378 | 4 | H | 3-Me—C6H4 | H | Me | Me |
| 379 | 4 | H | 4-Me—C6H4 | H | Me | Me |
| 380 | 4 | H | 2-CF3—C6H4 | H | Me | Me |
| 381 | 4 | H | 3-CF3—C6H4 | H | Me | Me |
| 382 | 4 | H | 4-CF3—C6H4 | H | Me | Me |
| 383 | 4 | H | 2-OCF3—C6H4 | H | Me | Me |
| 384 | 4 | H | 3-OCF3—C6H4 | H | Me | Me |
| 385 | 4 | H | 4-OCF3—C6H4 | H | Me | Me |
| 386 | 4 | H | 2-OMe—C6H4 | H | Me | Me |
| 387 | 4 | H | 3-OMe—C6H4 | H | Me | Me |
| 388 | 4 | H | 4-OMe—C6H4 | H | Me | Me |
| 389 | 4 | H | 2-CN—C6H4 | H | Me | Me |
| 390 | 4 | H | 3-CO2Me—C6H4 | H | Me | Me |
| 391 | 4 | H | Bn | H | Me | Me |
| 392 | 4 | H | 2-Cl—C6H4—CH2 | H | Me | Me |
| 393 | 4 | H | 3-Cl—C6H4—CH2 | H | Me | Me |
| 394 | 4 | H | 4-Cl—C6H4—CH2 | H | Me | Me |
| 395 | 4 | H | 2-Me—C6H4—CH2 | H | Me | Me |
| 396 | 4 | H | 3-OMe—C6H4—CH2 | H | Me | Me |
| 397 | 4 | H | 4-Me—C6H4—CH2 | H | Me | Me |
| 398 | 4 | H | 2-CF3—C6H4—CH2 | H | Me | Me |
| 399 | 4 | H | 3-CF3—C6H4—CH2 | H | Me | Me |
| 400 | 4 | H | 4-CF3—C6H4—CH2 | H | Me | Me |
| 401 | 4 | H | 2-Pyridyl | H | Me | Me |
| 402 | 4 | H | 3-Pyridyl | H | Me | Me |
| 403 | 4 | H | 4-Pyridyl | H | Me | Me |
| 404 | 4 | H | 2-Thienyl | H | Me | Me |

TABLE 1-3-continued

| No. | position of ACH2 | R4 | R5 | Xn | R1 | R2 |
|---|---|---|---|---|---|---|
| 405 | 4 | H | 3-Thienyl | H | Me | Me |
| 406 | 4 | H | 2-Furyl | H | Me | Me |
| 407 | 4 | H | PhO | H | Me | Me |
| 408 | 4 | H | 2-Cl—C6H4—O | H | Me | Me |
| 409 | 4 | H | 3-Me—C6H4—O | H | Me | Me |
| 410 | 4 | H | 2,4-Cl2—C6H3—O | H | Me | Me |
| 411 | 4 | H | BnO | H | Me | Me |
| 412 | 4 | H | 4-Me—C6H4—CH2O | H | Me | Me |
| 413 | 4 | H | 2-Me—C6H4—CH2O | H | Me | Me |
| 414 | 4 | H | 3-CF3—C6H4—CH2O | H | Me | Me |
| 415 | 4 | H | 4-CF3—C6H4—CH2O | H | Me | Me |
| 416 | 4 | H | PhOCH2 | H | Me | Me |
| 417 | 4 | H | 2,4-Cl2—C6H3OCH2 | H | Me | Me |
| 418 | 4 | H | 4-PhO—C6H4 | H | Me | Me |
| 419 | 4 | H | BnO | H | Et | Et |
| 420 | 4 | H | BnO | 4-Cl | Me | Me |
| 421 | 4 | Me | Me | H | Me | Me |
| 422 | 4 | Me | i-Pr | H | Me | Me |
| 423 | 4 | Me | i-Bu | H | Me | Me |
| 424 | 4 | Me | c-Hex | H | Me | Me |
| 425 | 4 | Me | Ph | H | Me | Me |
| 426 | 4 | Me | 2-Cl—C6H4 | H | Me | Me |
| 427 | 4 | Me | 3-Cl—C6H4 | H | Me | Me |
| 428 | 4 | Me | 4-Cl—C6H4 | H | Me | Me |
| 429 | 4 | Me | 2-Me—C6H4 | H | Me | Me |
| 430 | 4 | Me | 3-Me—C6H4 | H | Me | Me |
| 431 | 4 | Me | 4-Me—C6H4 | H | Me | Me |
| 432 | 4 | Me | 2-CF3—C6H4 | H | Me | Me |
| 433 | 4 | Me | 3-CF3—C6H4 | H | Me | Me |
| 434 | 4 | Me | 4-CF3—C6H4 | H | Me | Me |
| 435 | 4 | Me | 2-OCF3—C6H4 | H | Me | Me |
| 436 | 4 | Me | 3-OCF3—C6H4 | H | Me | Me |
| 437 | 4 | Me | 4-OCF3—C6H4 | H | Me | Me |
| 438 | 4 | Me | 2-OMe—C6H4 | H | Me | Me |
| 439 | 4 | Me | 3-OMe—C6H4 | H | Me | Me |
| 440 | 4 | Me | 2,4-Cl2—C6H3 | H | Me | Me |
| 441 | 4 | Me | 2-Br—C6H4 | H | Me | Me |
| 442 | 4 | Me | 3-Br—C6H4 | H | Me | Me |
| 443 | 4 | Me | 4-Br—C6H4 | H | Me | Me |
| 444 | 4 | Me | Bn | H | Me | Me |
| 445 | 4 | Me | 4-Cl—C6H4CH2 | H | Me | Me |
| 446 | 4 | Me | 2-Me—C6H4CH2 | H | Me | Me |
| 447 | 4 | Me | 3-CF3—C6H4CH2 | H | Me | Me |
| 448 | 4 | Me | PhCHMe | H | Me | Me |
| 449 | 4 | Me | PhCH2CH2 | H | Me | Me |
| 450 | 4 | Me | 4-EtO-2-Pyrimidyl | H | Me | Me |
| 451 | 4 | Me | 2-Pyrimidyl | H | Me | Me |
| 452 | 4 | Me | 4-Pyrimidyl | H | Me | Me |
| 453 | 4 | Me | 2-Pyridyl | H | Me | Me |
| 454 | 4 | Me | 3-Pyridyl | H | Me | Me |
| 455 | 4 | Me | 4-Pyridyl | H | Me | Me |
| 456 | 4 | Me | 2-Thienyl | H | Me | Me |
| 457 | 4 | Me | 3-Thienyl | H | Me | Me |
| 458 | 4 | Me | 2-Furyl | H | Me | Me |
| 459 | 4 | Me | BnO | H | Me | Me |
| 460 | 4 | Me | 2-Me—C6H4CH2 | H | Me | Me |
| 461 | 4 | Me | 3-Me—C6H4CH2 | H | Me | Me |
| 462 | 4 | Me | 4-Me—C6H4CH2 | H | Me | Me |
| 463 | 4 | Me | 2-CF3—C6H4CH2 | H | Me | Me |
| 464 | 4 | Me | 3-CF3—C6H4CH2 | H | Me | Me |
| 465 | 4 | Me | 4-CF3—C6H4CH2 | H | Me | Me |
| 466 | 4 | Me | 2-OMe—C6H4CH2 | H | Me | Me |
| 467 | 4 | Me | 3-OMe—C6H4CH2 | H | Me | Me |
| 468 | 4 | Me | 4-OMe—C6H4CH2 | H | Me | Me |
| 469 | 4 | Me | 2-Cl—C6H4CH2 | H | Me | Me |
| 470 | 4 | Me | 3-Cl—C6H4CH2 | H | Me | Me |
| 471 | 4 | Me | 4-Cl—C6H4CH2 | H | Me | Me |
| 472 | 4 | Me | BnS | H | Me | Me |
| 473 | 4 | Me | PhO | H | Me | Me |
| 474 | 4 | Me | PhS | H | Me | Me |
| 475 | 4 | Me | EtO | H | Me | Me |
| 476 | 4 | Me | EtS | H | Me | Me |
| 477 | 4 | Me | CH2=CHCH2O | H | Me | Me |
| 478 | 4 | Me | 2,4-Cl2—C6H3CH2O | H | Me | Me |
| 479 | 4 | Me | 2,4-Cl2—C6H3CH2 | H | Me | Me |
| 480 | 4 | Me | PhCHMe | H | Me | Me |

TABLE 1-3-continued

| No. | position of ACH2 | R4 | R5 | Xn | R1 | R2 |
|---|---|---|---|---|---|---|
| 481 | 4 | CN | Ph | H | Me | Me |
| 482 | 4 | CN | 2-Cl—C6H4 | H | Me | Me |
| 483 | 4 | CN | 3-Cl—C6H4 | H | Me | Me |
| 484 | 4 | CN | 4-Cl—C6H4 | H | Me | Me |
| 485 | 4 | CN | 2-Me—C6H4 | H | Me | Me |
| 486 | 4 | CN | 3-Me—C6H4 | H | Me | Me |
| 487 | 4 | CN | 4-Me—C6H4 | H | Me | Me |
| 488 | 4 | CN | 2-CF3—C6H4 | H | Me | Me |
| 489 | 4 | CN | 3-CF3—C6H4 | H | Me | Me |
| 490 | 4 | CN | 4-CF3—C6H4 | H | Me | Me |
| 491 | 4 | CN | 2-OCF3—C6H4 | H | Me | Me |
| 492 | 4 | CN | 3-OCF3—C6H4 | H | Me | Me |
| 493 | 4 | CN | 4-OCF3—C6H4 | H | Me | Me |
| 494 | 4 | CN | 2-OMe—C6H4 | H | Me | Me |
| 495 | 4 | CN | 3-OMe—C6H4 | H | Me | Me |
| 496 | 4 | CN | 2,4-Cl2—C6H3 | H | Me | Me |
| 497 | 4 | CN | 2-Br—C6H4 | H | Me | Me |
| 498 | 4 | CN | 3-Br—C6H4 | H | Me | Me |
| 499 | 4 | CN | 4-Br—C6H4 | H | Me | Me |
| 500 | 4 | CN | 4-CO2Me—C6H4 | H | Me | Me |
| 501 | 4 | CN | 4-CN—C6H4 | H | Me | Me |
| 502 | 4 | CN | 2-CN—C6H4 | H | Me | Me |
| 503 | 4 | Et | Ph | H | Me | Me |
| 504 | 4 | Et | Bn | H | Me | Me |
| 505 | 4 | Et | PhO | H | Me | Me |
| 506 | 4 | Et | BnO | H | Me | Me |
| 507 | 4 | Et | PhS | H | Me | Me |
| 508 | 4 | Et | BnS | H | Me | Me |
| 509 | 4 | Et | PhCHMeO | H | Me | Me |
| 510 | 4 | Et | Et | H | Me | Me |
| 511 | 4 | Et | 4-Pyrimidyl | H | Me | Me |
| 512 | 4 | Et | 2-Thienyl | H | Me | Me |
| 513 | 4 | Et | 2-Pyrimidyl | H | Me | Me |
| 514 | 4 | c-Pr | Ph | H | Me | Me |
| 515 | 4 | c-Pr | Bn | H | Me | Me |
| 516 | 4 | c-Pr | PhO | H | Me | Me |
| 517 | 4 | c-Pr | BnO | H | Me | Me |
| 518 | 4 | c-Pr | PhS | H | Me | Me |
| 519 | 4 | c-Pr | BnS | H | Me | Me |
| 520 | 4 | c-Pr | PhCHMeO | H | Me | Me |
| 521 | 4 | c-Pr | Et | H | Me | Me |
| 522 | 4 | c-Pr | 2-Pyrimidyl | H | Me | Me |
| 523 | 4 | c-Pr | 2-Thienyl | H | Me | Me |
| 524 | 4 | c-Pr | 2-Pyrimidyl | H | Me | Me |
| 525 | 4 | CH2=CHCH2 | CH2=CHCH2 | H | Me | Me |
| 526 | 4 | CH2=CHCH2 | Ph | H | Me | Me |
| 527 | 4 | CH2=CHCH2 | 4-OMe—C6H4 | H | Me | Me |
| 528 | 4 | CH2=CHCH2 | 4-Me—C6H4 | H | Me | Me |
| 529 | 4 | Ph | Ph | H | Me | Me |
| 530 | 4 | Ph | Bn | H | Me | Me |
| 531 | 4 | Ph | PhO | H | Me | Me |
| 532 | 4 | Ph | BnO | H | Me | Me |
| 533 | 4 | Ph | PhS | H | Me | Me |
| 534 | 4 | Ph | BnS | H | Me | Me |
| 535 | 4 | Ph | MeO | H | Me | Me |
| 536 | 4 | Ph | EtO | H | Me | Me |
| 537 | 4 | Ph | i-PrO | H | Me | Me |
| 538 | 4 | Ph | EtS | H | Me | Me |
| 539 | 4 | Ph | CH2=CHCH2O | H | Me | Me |
| 540 | 4 | Ph | PhCH2CH2O | H | Me | Me |
| 541 | 2 | Et | BnO | 4-Cl | Me | Me |
| 542 | 2 | Et | 4-CO2Me—C6H4CH2O | H | Me | Me |
| 543 | 2 | Et | 3-CN—C6H4CH2O | H | Me | Me |
| 544 | 2 | Et | 4-CN—C6H4CH2O | H | Me | Me |
| 545 | 2 | Et | 2-F—C6H4CH2O | H | Me | Me |
| 546 | 2 | Et | 3-F—C6H4CH2O | H | Me | Me |
| 547 | 2 | Et | 4-F—C6H4CH2O | H | Me | Me |
| 548 | 2 | Et | 2-Cl-4-F—C6H3CH2O | H | Me | Me |
| 549 | 2 | Et | 4-Cl-2-F—C6H3CH2O | H | Me | Me |
| 550 | 2 | Et | 3-CF3—C6H4CH2O | 4-Cl | Me | Me |
| 551 | 2 | Et | 4-OCF3—C6H4CH2O | 4-Cl | Me | Me |
| 552 | 2 | Et | 3-Me—C6H4CH2O | 4-Cl | Me | Me |
| 553 | 2 | Et | 2-Cl—C6H4CH2O | H | Me | Me |
| 554 | 2 | Et | 2-Cl—C6H4CH2O | 4-Cl | Me | Me |
| 555 | 2 | Et | 3-Cl—C6H4CH2O | H | Me | Me |
| 556 | 2 | Et | 4-Cl—C6H4CH2O | H | Me | Me |

TABLE 1-3-continued

| No. | position of ACH2 | R4 | R5 | Xn | R1 | R2 |
|---|---|---|---|---|---|---|
| 557 | 2 | Et | 2-Me—C6H4CH2O | H | Me | Me |
| 558 | 2 | Et | 3-Me—C6H4CH2O | 6-Cl | Me | Me |
| 559 | 2 | Et | 4-Me—C6H4CH2O | H | Me | Me |
| 560 | 2 | Et | 2-CF3—C6H4CH2O | H | Me | Me |
| 561 | 2 | Et | 3-CF3—C6H4CH2O | H | Me | Me |
| 562 | 2 | Et | 4-CF3—C6H4CH2O | H | Me | Me |
| 563 | 2 | Et | 2-OCF3—C6H4CH2O | 4-MeO | Me | Me |
| 564 | 2 | Et | 3-OCF3—C6H4CH2O | H | Me | Me |
| 565 | 2 | Et | 4-OCF3—C6H4CH2O | H | Me | Me |
| 566 | 2 | Et | 2-OMe—C6H4CH2O | H | Me | Me |
| 567 | 2 | Et | 3-OMe—C6H4CH2O | H | Me | Me |
| 568 | 2 | Et | 4-OMe—C6H4CH2O | H | Me | Me |
| 569 | 2 | Et | 2-CN—C6H4CH2O | H | Me | Me |
| 570 | 2 | Et | 3-CO2Me—C6H4CH2O | H | Me | Me |
| 571 | 2 | c-Pr | 2-CO2Me—C6H4CH2O | H | Me | Me |
| 572 | 2 | c-Pr | 4-CO2Me—C6H4CH2O | H | Me | Me |
| 573 | 2 | c-Pr | 3-CN—C6H4CH2O | H | Me | Me |
| 574 | 2 | c-Pr | 4-CN—C6H4CH2O | H | Me | Me |
| 575 | 2 | c-Pr | 2-F—C6H4CH2O | H | Me | Me |
| 576 | 2 | c-Pr | 3-F—C6H4CH2O | H | Me | Me |
| 577 | 2 | c-Pr | 4-F—C6H4CH2O | H | Me | Me |
| 578 | 2 | c-Pr | 2-Cl-4-F—C6H3CH2O | H | Me | Me |
| 579 | 2 | c-Pr | 4-Cl-2-F—C6H3CH2O | H | Me | Me |
| 580 | 2 | c-Pr | 3-CF3—C6H4CH2O | 4-Cl | Me | Me |
| 581 | 2 | c-Pr | 4-OCF3—C6H4CH2O | 4-Cl | Me | Me |
| 582 | 2 | c-Pr | 3-Me—C6H4CH2O | 4-Cl | Me | Me |
| 583 | 2 | c-Pr | 2-Cl—C6H4CH2O | H | Me | Me |
| 584 | 2 | c-Pr | 2-Cl—C6H4CH2O | 4-Cl | Me | Me |
| 585 | 2 | c-Pr | 3-Cl—C6H4CH2O | H | Me | Me |
| 586 | 2 | c-Pr | 4-Cl—C6H4CH2O | H | Me | Me |
| 587 | 2 | c-Pr | 2-Me—C6H4CH2O | H | Me | Me |
| 588 | 2 | c-Pr | 3-Me—C6H4CH2O | 6-Cl | Me | Me |
| 589 | 2 | c-Pr | 4-Me—C6H4CH2O | H | Me | Me |
| 590 | 2 | c-Pr | 2-CF3—C6H4CH2O | H | Me | Me |
| 591 | 2 | c-Pr | 3-CF3—C6H4CH2O | H | Me | Me |
| 592 | 2 | c-Pr | 4-CF3—C6H4CH2O | H | Me | Me |
| 593 | 2 | c-Pr | 2-OCF3—C6H4CH2O | 4-MeO | Me | Me |
| 594 | 2 | c-Pr | 3-OCF3—C6H4CH2O | H | Me | Me |
| 595 | 2 | c-Pr | 4-OCF3—C6H4CH2O | H | Me | Me |
| 596 | 2 | c-Pr | 2-OMe—C6H4CH2O | H | Me | Me |
| 597 | 2 | c-Pr | 3-OMe—C6H4CH2O | H | Me | Me |
| 598 | 2 | c-Pr | 4-OMe—C6H4CH2O | H | Me | Me |
| 599 | 2 | c-Pr | 2-CN—C6H4CH2O | H | Me | Me |
| 600 | 2 | c-Pr | 3-CO2Me—C6H4CH2O | H | Me | Me |
| 601 | 3 | Et | 2-CO2Me—C6H4CH2O | H | Me | Me |
| 602 | 3 | Et | 4-CO2Me—C6H4CH2O | H | Me | Me |
| 603 | 3 | Et | 3-CN—C6H4CH2O | H | Me | Me |
| 604 | 3 | Et | 4-CN—C6H4CH2O | H | Me | Me |
| 605 | 3 | Et | 2-F—C6H4CH2O | H | Me | Me |
| 606 | 3 | Et | 3-F—C6H4CH2O | H | Me | Me |
| 607 | 3 | Et | 4-F—C6H4CH2O | H | Me | Me |
| 608 | 3 | Et | 2-Cl-4-F—C6H3CH2O | H | Me | Me |
| 609 | 3 | Et | 4-Cl-2-F—C6H3CH2O | H | Me | Me |
| 610 | 3 | Et | 3-CF3—C6H4CH2O | 4-Cl | Me | Me |
| 611 | 3 | Et | 4-OCF3—C6H4CH2O | 4-Cl | Me | Me |
| 612 | 3 | Et | 3-Me—C6H4CH2O | 4-Cl | Me | Me |
| 613 | 3 | Et | 2-Cl—C6H4CH2O | H | Me | Me |
| 614 | 3 | Et | 2-Cl—C6H4CH2O | 4-Cl | Me | Me |
| 615 | 3 | Et | 3-Cl—C6H4CH2O | H | Me | Me |
| 616 | 3 | Et | 4-Cl—C6H4CH2O | W | Me | Me |
| 617 | 3 | Et | 2-Me—C6H4CH2O | H | Me | Me |
| 618 | 3 | Et | 3-Me—C6H4CH2O | 6-Cl | Me | Me |
| 619 | 3 | Et | 4-Me—C6H4CH2O | H | Me | Me |
| 620 | 3 | Et | 2-CF3—C6H4CH2O | H | Me | Me |
| 621 | 3 | Et | 3-CF3—C6H4CH2O | H | Me | Me |
| 622 | 3 | Et | 4-CF3—C6H4CH2O | H | Me | Me |
| 623 | 3 | Et | 2-OCF3—C6H4CH2O | 4-MeO | Me | Me |
| 624 | 3 | Et | 3-OCF3—C6H4CH2O | H | Me | Me |
| 625 | 3 | Et | 4-OCF3—C6H4CH2O | H | Me | Me |
| 626 | 3 | Et | 2-OMe—C6H4CH2O | H | Me | Me |
| 627 | 3 | Et | 3-OMe—C6H4CH2O | H | Me | Me |
| 628 | 3 | Et | 4-OMe—C6H4CH2O | H | Me | Me |
| 629 | 3 | Et | 2-CN—C6H4CH2O | H | Me | Me |
| 630 | 3 | Et | 3-CO2Me—C6H4CH2O | H | Me | Me |
| 631 | 3 | c-Pr | 2-CO2Me—C6H4CH2O | H | Me | Me |
| 632 | 3 | c-Pr | 4-CO2Me—C6H4CH2O | H | Me | Me |

TABLE 1-3-continued

| No. | position of ACH2 | R4 | R5 | Xn | R1 | R2 |
|---|---|---|---|---|---|---|
| 633 | 3 | c-Pr | 3-CN—C6H4CH2O | H | Me | Me |
| 634 | 3 | c-Pr | 4-CN—C6H4CH2O | H | Me | Me |
| 635 | 3 | c-Pr | 2-F—C6H4CH2O | H | Me | Me |
| 636 | 3 | c-Pr | 3-F—C6H4CH2O | H | Me | Me |
| 637 | 3 | c-Pr | 4-F—C6H4CH2O | H | Me | Me |
| 638 | 3 | c-Pr | 2-Cl-4-F—C6H3CH2O | H | Me | Me |
| 639 | 3 | c-Pr | 4-Cl-2-F—C6H3CH2O | H | Me | Me |
| 640 | 3 | c-Pr | 3-CF3—C6H4CH2O | 4-Cl | Me | Me |
| 641 | 3 | c-Pr | 4-OCF3—C6H4CH2O | 4-Cl | Me | Me |
| 642 | 3 | c-Pr | 3-Me—C6H4CH2O | 4-Cl | Me | Me |
| 643 | 3 | c-Pr | 2-Cl—C6H4CH2O | H | Me | Me |
| 644 | 3 | c-Pr | 2-Cl—C6H4CH2O | 4-Cl | Me | Me |
| 645 | 3 | c-Pr | 3-Cl—C6H4CH2O | H | Me | Me |
| 646 | 3 | c-Pr | 4-Cl—C6H4CH2O | H | Me | Me |
| 647 | 3 | c-Pr | 2-Me—C6H4CH2O | H | Me | Me |
| 648 | 3 | c-Pr | 3-Me—C6H4CH2O | 6-Cl | Me | Me |
| 649 | 3 | c-Pr | 4-Me—C6H4CH2O | H | Me | Me |
| 650 | 3 | c-Pr | 2-CF3—C6H4CH2O | H | Me | Me |
| 651 | 3 | c-Pr | 3-CF3—C6H4CH2O | H | Me | Me |
| 652 | 3 | c-Pr | 4-CF3—C6H4CH2O | H | Me | Me |
| 653 | 3 | c-Pr | 2-OCF3—C6H4CH2O | 4-MeO | Me | Me |
| 654 | 3 | c-Pr | 3-OCF3—C6H4CH2O | H | Me | Me |
| 655 | 3 | c-Pr | 4-OCF3—C6H4CH2O | H | Me | Me |
| 656 | 3 | c-Pr | 2-OMe—C6H4CH2O | H | Me | Me |
| 657 | 3 | c-Pr | 3-OMe—C6H4CH2O | H | Me | Me |
| 658 | 3 | c-Pr | 4-OMe—C6H4CH2O | H | Me | Me |
| 659 | 3 | c-Pr | 2-CN—C6H4CH2O | H | Me | Me |
| 660 | 3 | c-Pr | 3-CO2Me—C6H4CH2O | H | Me | Me |
| 661 | 4 | Et | 2-CO2Me—C6H4CH2O | H | Me | Me |
| 662 | 4 | Et | 4-CO2Me—C6H4CH2O | H | Me | Me |
| 663 | 4 | Et | 3-CN—C6H4CH2O | H | Me | Me |
| 664 | 4 | Et | 4-CN—C6H4CH2O | H | Me | Me |
| 665 | 4 | Et | 2-F—C6H4CH2O | H | Me | Me |
| 666 | 4 | Et | 3-F—C6H4CH2O | H | Me | Me |
| 667 | 4 | Et | 4-F—C6H4CH2O | H | Me | Me |
| 668 | 4 | Et | 2-Cl-4-F—C6H3CH2O | H | Me | Me |
| 669 | 4 | Et | 4-Cl-2-F—C6H3CH2O | H | Me | Me |
| 670 | 4 | Et | 3-CF3—C6H4CH2O | 2-Cl | Me | Me |
| 671 | 4 | Et | 4-OCF3—C6H4CH2O | 2-Cl | Me | Me |
| 672 | 4 | Et | 3-Me—C6H4CH2O | 2-Cl | Me | Me |
| 673 | 4 | Et | 2-Cl—C6H4CH2O | H | Me | Me |
| 674 | 4 | Et | 2-Cl—C6H4CH2O | 2-Cl | Me | Me |
| 675 | 4 | Et | 3-Cl—C6H4CH2O | H | Me | Me |
| 676 | 4 | Et | 4-Cl—C6H4CH2O | H | Me | Me |
| 677 | 4 | Et | 2-Me—C6H4CH2O | H | Me | Me |
| 678 | 4 | Et | 3-Me—C6H4CH2O | 2-Cl | Me | Me |
| 679 | 4 | Et | 4-Me—C6H4CH2O | H | Me | Me |
| 680 | 4 | Et | 2-CF3—C6H4CH2O | H | Me | Me |
| 681 | 4 | Et | 3-CF3—C6H4CH2O | H | Me | Me |
| 682 | 4 | Et | 4-CF3—C6H4CH2O | H | Me | Me |
| 683 | 4 | Et | 2-OCF3—C6H4CH2O | 2-MeO | Me | Me |
| 684 | 4 | Et | 3-OCF3—C6H4CH2O | H | Me | Me |
| 685 | 4 | Et | 4-OCF3—C6H4CH2O | H | Me | Me |
| 686 | 4 | Et | 2-OMe—C6H4CH2O | H | Me | Me |
| 687 | 4 | Et | 3-OMe—C6H4CH2O | H | Me | Me |
| 688 | 4 | Et | 4-OMe—C6H4CH2O | H | Me | Me |
| 689 | 4 | Et | 2-CN—C6H4CH2O | H | Me | Me |
| 690 | 4 | Et | 3-CO2Me—C6H4CH2O | H | Me | Me |
| 691 | 4 | c-Pr | 2-CC2Me—C6H4CH2O | H | Me | Me |
| 692 | 4 | c-Pr | 4-CO2Me—C6H4CH2O | H | Me | Me |
| 693 | 4 | c-Pr | 3-CN—C6H4CH2O | H | Me | Me |
| 694 | 4 | c-Pr | 4-CN—C6H4CH2O | H | Me | Me |
| 695 | 4 | c-Pr | 2-F—C6H4CH2O | H | Me | Me |
| 696 | 4 | c-Pr | 3-F—C6H4CH2O | H | Me | Me |
| 697 | 4 | c-Pr | 4-F—C6H4CH2O | H | Me | Me |
| 698 | 4 | c-Pr | 2-Cl-4-F—C6H3CH2O | H | Me | Me |
| 699 | 4 | c-Pr | 4-Cl-2-F—C6H3CH2O | H | Me | Me |
| 700 | 4 | c-Pr | 3-CF3—C6H4CH2O | 2-Cl | Me | Me |
| 701 | 4 | c-Pr | 4-OCF3—C6H4CH2O | 2-Cl | Me | Me |
| 702 | 4 | c-Pr | 3-Me—C6H4CH2O | 2-Cl | Me | Me |
| 703 | 4 | c-Pr | 2-Cl—C6H4CH2O | H | Me | Me |
| 704 | 4 | c-Pr | 2-Cl—C6H4CH2O | 2-Cl | Me | Me |
| 705 | 4 | c-Pr | 3-Cl—C6H4CH2O | H | Me | Me |
| 706 | 4 | c-Pr | 4-Cl—C6H4CH2O | H | Me | Me |
| 707 | 4 | c-Pr | 2-Me—C6H4CH2O | H | Me | Me |
| 708 | 4 | c-Pr | 3-Me—C6H4CH2O | 2-Cl | Me | Me |

TABLE 1-3-continued

| No. | position of ACH2 | R4 | R5 | Xn | R1 | R2 |
|---|---|---|---|---|---|---|
| 709 | 4 | c-Pr | 4-Me—C6H4CH2O | H | Me | Me |
| 710 | 4 | c-Pr | 2-CF3—C6H4CH2O | H | Me | Me |
| 711 | 4 | c-Pr | 3-CF3—C6H4CH2O | H | Me | Me |
| 712 | 4 | c-Pr | 4-CF3—C6H4CH2O | H | Me | Me |
| 713 | 4 | c-Pr | 2-OCF3—C6H4CH2O | 2-MeO | Me | Me |
| 714 | 4 | c-Pr | 3-OCF3—C6H4CH2O | H | Me | Me |
| 715 | 4 | c-Pr | 4-OCF3—C6H4CH2O | H | Me | Me |
| 716 | 4 | c-Pr | 2-OMe—C6H4CH2O | H | Me | Me |
| 717 | 4 | c-Pr | 3-OMe—C6H4CH2O | H | Me | Me |
| 718 | 4 | c-Pr | 4-OMe—C6H4CH2O | H | Me | Me |
| 719 | 4 | c-Pr | 2-CN—C6H4CH2O | H | Me | Me |
| 720 | 4 | c-Pr | 3-CO2Me—C6H4CH2O | H | Me | Me |

Compounds of formula (I) above may be prepared by the application or adaptation of known methods (i.e. methods heretofore used or described in the literature).

It is to be understood that in the descriptions of the following processes the sequences may be performed in different orders, and that suitable protecting groups may be required to achieve the compounds sought.

According to a feature of this present invention compounds of formula (I-1) wherein $R_1$, $R_2$ and Xn are as defined above in the general formula (I), and B represents a halogen atom, may be prepared by the reaction of a compound of general formula (III):

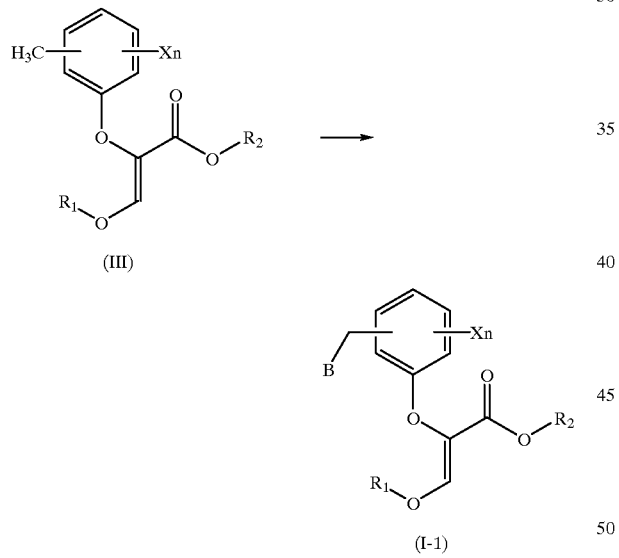

wherein $R_1$, $R_2$ and Xn are as defined above, with a suitable halogenating agent generally in an inert solvent or with no solvent, optionally with a radical initiator, and optionally in the presence of light. Suitable halogenating agents are for example, chlorine, bromine, N-bromosuccinimide, N-chlorosuccinimide or N-iodosuccinimide. Although there is no special limitation for the proportion of a halogenating agent to a compound of formula (III), it is convenient to use the halogenating agent in the range from 0.5 to 2 moles, more preferably 0.9 to 1.1 moles per mole of compound of formula (III).

Suitable radical initiators are for example, benzoylperoxide or azobisisobutyronitrile. Suitable solvents are for example, aliphatic hydrocarbons such as pentane, hexane, heptane or octane; aromatic hydrocarbons such as benzene; halogenated hydrocarbons such as dichloromethane, chloroform or dichloroethane. These solvents can be used alone or in admixture.

The reaction temperature is generally in the range from −80 C. to 150 C. or the boiling point of solvent used. The reaction time is generally in the range from 0.1 to 24 hours.

According to a further feature of this present invention compounds of formula (I-2):

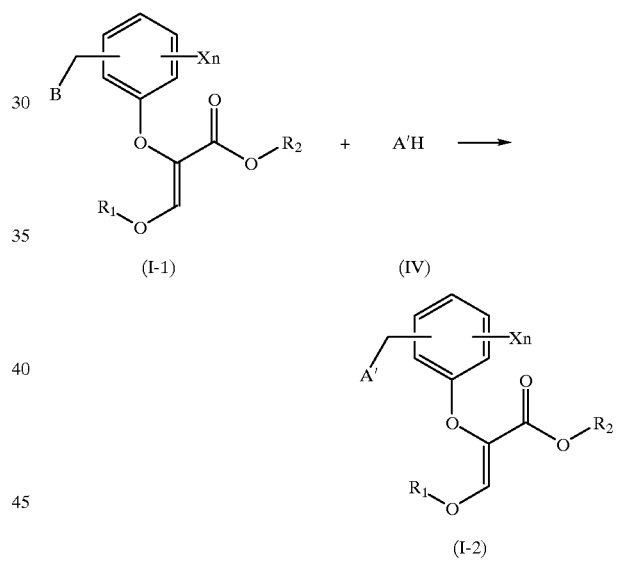

wherein $R_1$, $R_2$ and Xn are as defined above in the general formula (I), and A' represents $OR_3$, $SR_3$, A-1 or A-2, wherein $R_1$, $R_2$, A-1 and A-2 are as defined above, and $R_3$ represents optionally substituted lower alkyl, optionally substituted lower alkenyl, optionally substituted lower alkynyl, optionally substituted cycloalkyl, optionally substituted phenyl, optionally substituted heteroaryl, optionally substituted cycloalkenyl, —$C_pH_{2p}$ (optionally substituted phenyl), —$C_qH_{2q}$ (optionally substituted heteroaryl), —$(C_rH_{2r})$ $CO_2$alkyl, —$(C_sH_{2s})$ cycloalkyl, —$(C_uH_{2u})$ $COCH_2$ (optionally substituted phenyl), —$(C_fH_{2f})$ O (optionally substituted phenyl), —$(C_gH_{2g})$ S (optionally substituted phenyl), or —$(C_jH_{2j})$ O $(C_zH_{2z})$(optionally substituted phenyl);

may be prepared by the reaction of a compound of general formula (I-1) wherein, Xn, $R_1$ and $R_2$ are as defined above, and B represents a halogen atom, with a compound of formula (IV). In the case where A' represents A-2 the compound A'H is the amide $R_4C(=O)NHR_5$ when the alkylation reaction to give (I-2) occurs on the oxygen atom of the amide. The reaction is generally performed in a suitable solvent or without solvent, and preferably in the presence of an acid binding agent. Suitable acid binding agents are for example alkali or alkaline earth metal hydroxides such as sodium hydroxide, potassium hydroxide or calcium hydroxide; alkali or alkaline earth metal carbonates or bicarbonates such as sodium carbonate, potassium carbonate, cesium carbonate, calcium carbonate, sodium bicarbonate or potassium bicarbonate; alkali metal hydrides such as sodium hydride or potassium hydride; alkali metal alkoxides such as sodium methoxide, sodium ethoxide or potassium tert-butoxide; or organic bases such as pyridine, triethylamine, 4-N,N-dimethylaminopyridine, diazabicycloundecene or diazabicylooctane. The molar ratio of the compound of formula (IV) to the compound of formula (I-1) is preferably in the range from 0.5 to 2 moles and more preferably from 0.9 to 1.1 moles. Suitable solvents are for example aliphatic hydrocarbons such as pentane, hexane, heptane or octane; aromatic hydrocarbons such as benzene, toluene or xylene; ethers such as diethyl ether, tetrahydrofuran, dioxane or dimethoxyethane; halogenated hydrocarbons such as dichloromethane, chloroform or dichloroethane; alcohols such as methanol, ethanol or isopropanol; esters such as methyl acetate or ethyl acetate; nitrites such as acetonitrile or propionitrile; N,N-dimethylformamide, dimethylsulfoxide or water. The reaction temperature is generally in the range from –80 C. to 150 C. or the boiling point of solvent used. The reaction time is generally in the range of 0.1 to 24 hours.

According to a further feature of this present invention the E-isomers conforming to formula (VI):

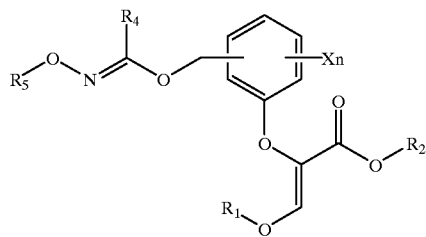

wherein $R_1$, $R_2$, $R_4$, $R_5$ and Xn are as defined above in the general formula (I), may be prepared by isomerisation of the corresponding Z isomers conforming to formula (V):

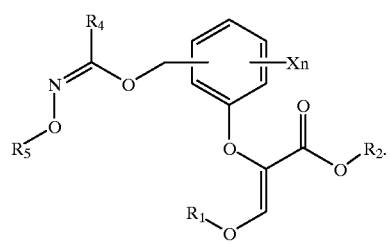

The isomerisation of the Z isomers of formula (V) to give the E isomers of formula (VI) may be performed using an acid. Suitable acids for the reaction are for example organic acid such as formic acid, acetic acid, propionic acid or trifluoroacetic acid; sulfonic acids such as benzenesulfonic acid or paratoluenesulfonic acid; or inorganic acids such as hydrochloric acid, sulfuric acid or hydrobromic acid. Suitable solvents are for example aliphatic hydrocarbons such as pentane, hexane, heptane or octane; aromatic hydrocarbons such as benzene, toluene or xylene; ethers such as diethyl ether, tetrahydrofuran, dioxane or dimethoxyethane; halogenated hydrocarbons such as dichloromethane, chloroform or dichloroethane; alcohols such as methanol, ethanol or isopropanol; esters such as methyl acetate or ethyl acetate; nitriles such as acetonitrile or propionitrile; or N,N-dimethylformamide, dimethylsulfoxide or water. The solvents can be used alone or in admixture. The reaction temperature is generally from –80 C. to 150 C. or the boiling point of the solvent used. The reaction time is generally in the range from 0.1 to 24 hours.

According to a further feature of this present invention compounds of formula (I-4):

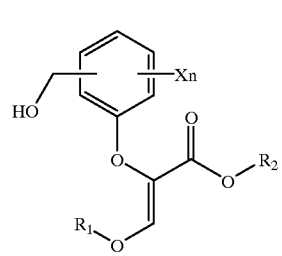

wherein $R_1$, $R_2$ and Xn are as defined above in the general formula (I), may be prepared by the hydrolysis of a compound of general formula (I-3):

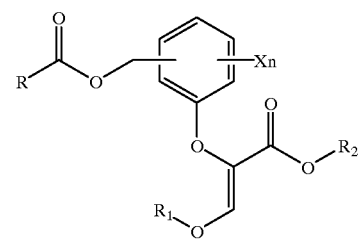

wherein, $R_1$, $R_2$ and Xn are as defined and R represents an alkyl group preferably lower alkyl for example methyl or ethyl.

The hydrolysis is generally performed in the presence of a base. Suitable bases are for example alkali or alkaline earth metal hydroxides such as sodium hydroxide, potassium hydroxide or calcium hydroxide; or alkali or alkaline earth metal carbonates such as sodium carbonate, potassium carbonate, cesium carbonate or calcium carbonate. The proportion of base to compound of formula (I-3) is generally from 1.0 to 10 moles of base per mole of compound of formula (I-3). Suitable solvents include water optionally in admixture with alcohols such as methanol or ethanol, and ethers such as dioxan or tetrahydrofuran. The reaction temperature is generally from –80 C. to 150 C. or boiling the point of solvent used (preferably from 0 C. to 50 C.).

According to a further feature of this present invention compounds of formula (I) wherein $R_1$, $R_2$ and Xn are as defined above and A represents $OR_3$ or $SR_3$ wherein $R_3$ represents optionally substituted lower alkylcarbonyl, optionally substituted lower alkenylcarbonyl, optionally substituted lower alkynylcarbonyl, optionally substituted cycloalkylcarbonyl, optionally substituted phenylcarbonyl, optionally substituted heteroarylcarbonyl, optionally substituted cycloalkenylcarbonyl or —CO($C_rH_{2r}$) Y and Y is as defined above, may be prepared by the acylation of the corresponding compound of formula (I) wherein A represents OH or is replaced by SH. The reaction is generally performed using an acid halide (preferably chloride) of formula (VII):

R₃COW  (VII)

wherein W represents a halide group, in an inert solvent such as dichloromethane or tetrahydrofuran at a temperature of from 0 to 80 C.

According to a further feature of this present invention compounds of formula (I) wherein R₁, R₂, Xn are as defined above and A represents a group S(O)ₖR₃ wherein k is one or two may be prepared by the oxidation of the corresponding compounds in which k represents zero or one. The reaction is generally performed using an oxidant such as m-chloroperbenzoic acid in a solvent such as chloroform at a temperature of from 0 to the reflux temperature of the solvent.

Intermediates of formula (III) may be prepared by the alkylation of compounds of formula (VIII) which are in tautomeric equilibrium with compounds of formula (VIIIa):

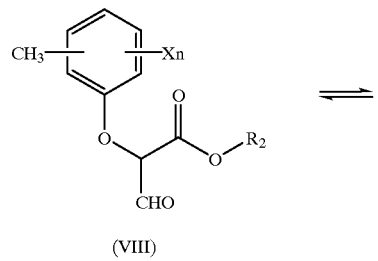

(VIII)

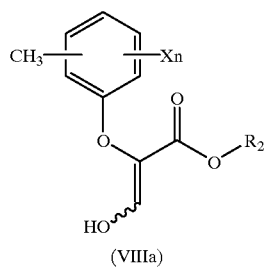

(VIIIa)

using an alkylating agent of formula R₁Q wherein Q represents a leaving group such as a halide (preferably iodide) or for example dialkylsulfate of formula (R₁)₂SO₄, generally in the presence of a base such as potassium carbonate, in a solvent such as N,N-dimethylformamide or acetone at 0–80 C. Compounds of formula (III) are novel and as such form a further feature of the present invention.

Intermediates of formula (VIII) may be prepared by the formylation of phenoxyacetic acid derivatives of formula (IX):

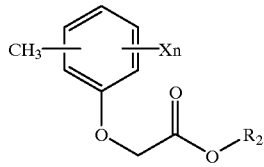

(IX)

generally using an alkyl formate of formula (X):

HCO₂Ra  (X)

wherein Ra represents lower alkyl preferably methyl or ethyl, generally in the presence of a base such as sodium hydride or an alkali metal alkoxide such as sodium methoxide, in a solvent such as tetrahydrofuran or N,N-dimethylformamide at a temperature of from 0–80 C.

Intermediates of formula (I) wherein A is replaced by a group SH may be prepared by the reaction of the corresponding compound of formula (I-1) wherein B represents a halogen atom preferably bromide, with a thiolating agent for example sodium hydrosulfide, according to methods described in the references cited in Advanced Organic Chemistry, third edition by Jerry March, page 360.

Compounds of formula (IV), (VII), (IX) and (X) are known or may be prepared by known methods. Compounds of formula (I-3) may be prepared according to the above method for the preparation of compounds of formula (I) wherein A represents OR3 and R3 represents lower alkylcarbonyl.

The following Examples illustrate the preparation of compounds of formula (I). It is to be understood that the present invention is not limited by these examples. All of the compounds described in the following Preparative Examples and in Table 2 are the Z isomers (at the double bond which is substituted by the OR1 group).

PREPARATION EXAMPLE 1

Preparation of Methyl 2-(3-Bromomethylphenoxy)-3-methoxyacrylate (Compound No. 1. 181)

A mixture of 9.6 g of methyl 2-(3-methylphenoxy)-3-methoxyacrylate, 8.0 g of N-bromosuccinimide and a catalytic amount of azobisisobutyronitrile was heated at reflux in carbon tetrachloride for 4 hours. After cooling, the solid was filtered, the filtrate evaporated, and purified by silica gel column chromatography to give methyl 2-(3-bromomethylphenoxy)-3-methoxyacrylate (6.5 g).

PREPARATION EXAMPLE 2

Preparation of Methyl 2-[2-(2-Methylphenoxy) methylphenoxy]-3-methoxyacrylate (Compound No. 2.6)

A mixture of 1.1 g of methyl 2-(2-methylphenoxy)-3-methoxyacrylate, 0.95 g of N-bromosuccinimide, and a catalytic amount of azobisisobutyronitrile was heated at reflux in carbon tetrachloride for 4 hours. The solid was filtered, and the solvent evaporated to give a crude sample of methyl 2-(2-bromomethylphenoxy)-3-methoxyacrylate. A mixture of this crude sample together with 0.6 g of o-cresol, and 1.0 g of potassium carbonate was heated at reflux in acetonitrile for 20 hours. The solid was filtered, the solvent evaporated, and the residue purified by silica gel chromatography to give methyl 2-[2-(2 -methylphenoxy) methylphenoxy]-3-methoxyacrylate (0.47 g).

PREPARATION EXAMPLE 3

Preparation of Methyl 2-{2-[(1-Benzyloxyiminopropyl)oxymethyl]phenoxy}-3-methoxyacrylate (Compound No. 5.146; Isomer Z)

A mixture of 2.2 g of methyl 2-(2-methylphenoxy)-3-methoxyacrylate, 1.78 g of N-bromosuccinimide, and a catalytic amount of azobisisobutyronitrile was heated at reflux in carbon tetrachloride for 4 hours. The solid was filtered, and the solvent evaporated to give crude methyl 2-(2-bromomethylphenoxy)-3-methoxyacrylate. A mixture of this crude material, 2.0 g of N-benzyloxy propionamide, and 3.9 g of caesium carbonate was heated at reflux in acetonitrile for 20 hours. The solid was filtered, the solvent evaporated, and the residue purified by silica gel chromatography to give methyl 2-{2-[(1-benzyloxyiminopropyl) oxymethyl]phenoxy}-3-methoxyacrylate (isomer Z) (0.75 g).

PREPARATION EXAMPLE 4

Preparation of Methyl 2-{2-[(1-Benzyloxyiminopropyl)oxymethyl]phenoxy}-3-methoxyacrylate (Compound No. 5.146; Isomer E)

A mixture of 0.47 g of methyl 2-{2-[(1-benzyloxyiminopropyl)oxymethyl]phenoxy}-3-methoxyacrylate (isomer Z), and a catalytic amount of acetic acid was heated at reflux in toluene for 6 hours. The solvent was evaporated and the residue purified by silica gel chromatography to give methyl 2-{2-[(1-benzyloxyiminopropyl) oxymethyl phenoxy}-3-methoxyacrylate (isomer E) (0.32 g).

PREPARATION EXAMPLE 5

Preparation of Methyl 2-(2-Acetyloxymethyl-4-chlorophenoxy)-3-methoxyacrylate (Compound No. 2.619)

A mixture of 5.13 g of methyl 2-(2-methyl-4-chlorophenoxy)-3-methoxyacrylate, 3.56 g of N-bromosuccinimide, and a catalytic amount of azobisisobutyronitrile was heated at reflux with light irradiation for 4 hours. The mixture was filtered through silica gel, and the solvent evaporated to give a crude sample of methyl 2-(2-bromomethylphenoxy)-3-methoxyacrylate. A mixture of this crude material and 2.46 g of sodium acetate in N,N-dimethylformamide was heated at 100 C. for 4 hours. Water was added and the mixture extracted with ethyl acetate, dried with anhydrous sodium sulfate, evaporated and the residue purified by silica gel column chromatography to give methyl 2-(2-acetyloxymethyl-4-chlorophenoxy)-3-methoxyacrylate) (3.2 g).

PREPARATION EXAMPLE 6

Preparation of Methyl 2-(2-Hydroxymethyl-4-chlorophenoxy)-3-methoxyacrylate (Compound No. 1.313)

Water was added to a solution of 1.42 g of methyl 2-(2-acetyloxymethyl-4-chlorophenoxy)-3-methoxyacrylate in methanol, and stirred at room temperature. Sodium carbonate (0.53 g) was added. After a further 0.5 hour water and ethyl acetate were added. The organic phase was dried with anhydrous sodium sulfate, evaporated and the residue purified by silica gel column chromatography to give methyl 2-(2-hydroxymethyl-4-chlorophenoxy)-3-methoxyacrylate (1.04 g).

PREPARATION EXAMPLE 7

Preparation of 2-[4-Chloro-2-(2-methylphenoxymethyl)]phenoxy-3-methoxyacrylic Acid (Compound No. 2.135)

Methyl 2-[4-chloro-2-(2-methylphenoxymethyl)] phenoxy-3-methoxyacrylate (3.3 g) was dissolved in tetrahydrofuran, a 2 N aqueous solution of sodium hydroxide added, and the mixture stirred at room temperature for 4 days. Diethyl ether and an aqueous solution of sodium bicarbonate were added, and the mixture stirred and transferred to a separation funnel and shaken vigorously. After removal of the organic layer, the water layer was acidified with a small amount of an aqueous solution of citric acid, and extracted with dichloromethane. The organic layer was dried with anhydrous sodium sulfate, and evaporated to give 2-[4-chloro-2-(2-methylphenoxymethyl)]phenoxy-3-methoxyacrylic acid (2.2 g).

Proton NMR details for the above preparative examples and for other compounds obtained by the above methods are shown in Table 2. Compounds 4.61, 4.68, 4.71, 4.99, 4.107, 4.248, 4.279, 4.428 and 4.459 were prepared according to the method of Example 3 but using sodium carbonate instead of cesium carbonate.

In Table 2 the following symbols are used: s=singlet, d=doublet, t=triplet, m=multiplet, dd=double doublet and td=triple doublet.

TABLE 2

| No. | NMR ppm in CDCl3 |
|---|---|
| 1.31 | 3.71(3H, s)3.88(3H, s)4.69(2H, s)6.78(1H, dd)6.99(1H, td) 7.10(1H, t)7.35(1H, s)7.38(1H, dd) |
| 1.73 | 3.71(3H, s)3.89(3H, s)4.61(2H, s)6.71(1H, d)7.15(1H, dd) 7.34(1H, s)7.37(1H, d) |
| 1.181 | 3.73(3H, s)3.87(3H, s)4.44(2H, s)6.87(1H, dd)6.98(1H, d) 7.03(1H, dd)7.24(1H, t)7.33(1H, s) |
| 1.187 | 3.72(3H, s)3.87(3H, s)4.49(2H, s)6.91(2H, d)7.31(2H, d) 7.32(1H, s) |
| 1.313 | 3.73(3H, s)3.92(3H, s)4.71(2H, bs)6.73(1H, d)7.16(1H, dd) 7.32(1H, d)7.35(1H, s) |
| 2.6 | 2.34(3H, s)3.71(3H, s)3.88(3H, s)5.31(2H, s)6.80(1H, dd) 6.85(1H, td)6.96(1H, dd)7.03(1H, td)7.10–7.21(3H, m) 7.34(1H, s)7.55(1H, dd) |
| 2.129 | 2.35(3H, s)3.72(3H, s)3.89(3H, s)5.26(2H, s)6.74(1H, d) 6.88(1H, td)6.94(1H, dd)7.12–7.19(3H, m)7.34(1H, s) 7.53(1H, d) |
| 2.135 | 2.33(3H, s)3.92(3H, s)5.23(2H, s)6.75(1H, d)6.85– 6.95(2H, m) 7.09–7.18(3H, m)7.43(1H, s)7.50(1H, d) |
| 2.333 | 2.26(3H, s)3.73(3H, s)3.87(3H, s)5.01(2H, s)6.87(2H, m) 6.97(2H, d)7.16(2H, m)7.33(1H, s)7.36(2H, d) |
| 2.619 | 2.14(3H, s)3.70(3H, s)3.87(3H, s)5.27(2H, s)6.72(1H, d) 7.16(1H, dd)7.31(1H, s)7.34(1H, d) |
| 4.61 | 1.90(3H, s)1.95(3H, s)3.69(3H, s)3.86(3H, s)5.24(2H, s) 6.68(1H, d)7.10(1H, dd)7.30(1H, s)7.31(1H, d) |
| 4.68 | 2.27(3H, s)3.70(3H, s)3.86(3H, s)5.45(2H, s)6.79(1H, dd) 7.00(1H, td)7.20(1H, td)7.31(2H, d)7.32(1H, s)7.40(1H, dd) 7.61(2H, d) |
| 4.71 | 2.29(3H, s)3.70(3H, s)3.87(3H, s)5.40(2H, s)6.71(1H, d) 7.13(1H, dd)7.32(2H, d)7.34(1H, s)7.37(1H, d)7.60(2H, d) |
| 4.99 | 2.04(3H, s)2.68(3H, s)3.84(3H, s)5.01(2H, s)5.18(2H, s) 6.77(1H, dd)6.99(1H, td)7.18(1H, td)7.26–7.40(7H, m) |
| 4.107 | 2.05(3H, s)3.70(3H, s)3.85(3H, s)5.00(2H, s)5.14(2H, s) 6.71(1H, d)7.13(1H, dd)7.31(1H, s)7.30–7.38(6H, m) |
| 4.248 | 2.24(3H, 5)3.69(3H, s)3.84(3H, s)5.20(2H, s)6.89(1H, dd) 7.02(1H, d)7.03(1H, dd)7.24(1H, t)7.31(1H, s)7.32(2H, d) 7.58(2H, d) |
| 4.279 | 2.00(3H, s)3.70(3H, s)3.85(3H, s)4.94(2H, s)4.98(2H, s) 6.99(1H, dd)7.00(1H, d)7.01(1H, dd)7.26(1H, t)7.32(1H, s) 7.30–7.39(5H, m) |
| 4.428 | 2.21(3H, s)3.72(3H, s)3.86(3H, s)5.15(2H, s)6.95(2H, d) 7.31–7.36(5H, m)7.58(2H, d) |
| 4.459 | 1.98(3H, s)3.72(3H, s)3.87(3H, s)4.89(2H, s)4.99(2H, s) 6.93(2H, d)7.33(1H, s)7.26–7.38(7H, m) |
| 5.506 E isomer* | 1.07(3H, t)2.43(2H, q)3.72(3H, s)3.86(3H, s)4.91(2H, s) 4.95(2H, s)4.92(2H, d)7.26(2H, d)7.32(1H, s) 7.27–7.38(5H, m) |
| 5.506 Z isomer* | 1.07(3H, t)2.19(2H, q)3.72(3H, s)3.86(3H, s)4.99(2H, s) 5.14(2H, s)6.92(2H, d)7.23(2H, d)7.32(1H, s) 7.29–7.40(5H, m) |
| 5.146 Z isomer* | 1.10(3H, t)2.27(2H, q)3.68(3H, s)3.84(3H, s)5.04(2H, s) 5.39(2H, s)6.75(1H, dd)6.98(1H, t)d7.17(1H, td) 7.31(1H, s)7.26–7.43(6H, m) |
| 5.146 | 1.11(3H, t)2.47(2H, q)3.68(3H, s)3.85(3H, s)4.97(2H, s) |

TABLE 2-continued

| No. | NMR ppm in CDCl3 |
|---|---|
| E isomer* | 5.19(2H, s)6.77(1H, dd)6.99(1H, td)7.17(1H, td)7.31(1H, s)7.27–7.40(6H, m) |
| 5.541 | 1.11(3H, s)2.47(2H, q)3.68(3H, 5)3.84(3H, s)4.94(2H, s) |
| E isomer* | 5.13(2H, s)6.69(1H, d)7.12(1H, dd)7.28–7.38(7H, m) |

*Z and E isomers around the C=N bond.

According to a feature of the present invention, there is provided a method for controlling the growth of weeds (i.e. undesired vegetation) at a locus which comprises applying to the locus a herbicidally effective amount of at least one phenoxyacetic acid derivative of formula I or an agriculturally acceptable salt thereof. For this purpose, the phenoxyacetic acid derivatives are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis,* and sedges, for example, *Cyperus esculentus.*

The compounds of this invention represented by the general formula (I) show excellent herbicidal effects at very low doses against a wide range of growth stages including paddy field annual weeds such as *Echinochloa orizicola, Cyperus difformis, Monochoria varinalis* var. *plantaginea, Rotaria indica* var. *uliginosa, Lindernia procumbens* and *Dopatrium junceum;* and paddy field perennial weeds such as *Scirpus juncoides* var. *hotarui, Eleocharis acicularis* var. *longiseta, Alisma canaliculatum* and *Cyperus serotinus.*

In addition the compounds of formula (I) are highly selective giving low levels of damage to transplanted rice plants and directly sown rice plants in either paddy or upland fields.

Further, the compounds of formula (I) exhibit very high herbicidal effects by soil or foliar application, on various upland broadleaf weeds such as *Persicaria longiseta, Amaranthus viridis* and *Chenopodium album;* on annual and perennial Cyperus weeds such as *Cyperus rotundus, Cyperus esculantus, Cyperus brevifolius* var. *leiolepis, Cyperus microiris* and *Cyperus iria;* and on upland gramineous weeds such as *Echinochloa crus-galli, Digitaria ciiaris, Setaria viridis, Poa annua, Sorghum halepense, Avena sativa* and *Alopecurus aequalis* var. *amerensis.*

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop.

The compounds of this invention can also be used in orchards, mulberry fields, turf, and non-farming lands.

According to a further feature of the present invention, there are provided compositions suitable for herbicidal use comprising one or more of the phenoxyacetic acid derivatives of formula I or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use.

When the compounds of this invention are used as herbicides, they can be mixed with carriers, diluents, additives and auxiliaries by methods known per se and formed into a formula which is acceptable as usual agricultural chemicals, for example, dust, granule, wettable powder, emulsifiable concentrate, soluble powder, flowable, etc. They can be used as mixture or in combination with other agricultural chemicals, for example, fungicides, insecticides, acaricides, herbicides, plant growth regulators, fertilizers and soil conditioners.

In particular, the use of the compounds of this invention as mixture with other herbicides can lead not only to reduction in dosage, or reduction in manpower, but also to broadening of herbicidal spectrum attributable to co-operative activities and further improved effects attributable to herbicidal activity by the both chemicals.

The carriers used for formulation includes generally using solid or liquid carriers.

As solid carriers, there can be cited, for example, clays represented by kaolinites, montmorillonites, illites and polygroskites; more specifically, pyrophyllite, attapulgite, sepiolite, kaolinite, bentonite, vermiculite, mica and talc; and other inorganic substances such as gypsum, calcium carbonate, dolomite, diatomaceus earth, magnesium lime, phosphorus lime, zeolite, silicic anhydrite and synthetic calcium silicate; organic substances of vegetable origin, such as soybean flour, tobacco flour, walnut flour, wheat flour, sawdust, starch and crystalline cellulose; synthetic or natural polymers such as coumarone resin, petroleum resin, alkyd resin, polyvinylchloride, polyalkylene glycol, ketone resin, ester gum, copal gum and dammar gum; waxes such as carnauba wax and bee wax; or urea and the like.

As liquid carriers, there can be cited, for example, paraffin or naphthene hydrocarbons such as kerosine, mineral oil, spindle oil and white oil; aromatic hydrocarbons such as xylene, ethylbenzene, cumene and methylnaphthalene; chlorinated hydrocarbons such as trichloroethylene, monochlorobenzene and o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, diethyleneglycol acetate, dibutyl maleate and diethyl succinate; alcohols such as methanol, n-hexanol, ethylene glycol, diethylene glycol, cyclohexanol and benzyl alcohol; ether alcohols such as ethylene glycol ethyl ether and diethylene glycol butyl ether; polar solvents such as N,N-dimethylformamide and dimethylsulfoxide; or water.

In addition, one or more surfactants and/or other auxiliary agents may be used for various purposes such as emulsification, dispersion, humidification, spreading, dilution, binding, destruction control, stabilization of active ingredients, improvement of flowability, prevention of corrosion and prevention of freezing, of the compounds of the present invention.

As surfactant, there can be used one of any types among nonionic, anionic, cationic and amphoteric surfactants. Usually, nonionic and/or anionic surfactants are used.

As suitable noninoic surfactants, there can be cited, for example, additive polymerization products of ethylene oxide with higher alcohols such as lauryl alcohol, stearyl alcohol and oleyl alcohol; additive polymerization products of ethylene oxide with alkylnaphthols such as butylnaphthol and octylnaphthol; additive polymerization products of ethylene oxide with higher fatty acids such as palmitic acid, stearic acid and oleic acid; esters of higher fatty acids and polyhydric alcohols such as sorbiten, and additive polymerization products of ethylene oxide, therewith; block polymerization products of ethylene oxide and propyleneoxide.

As suitable anionic surfactants, there can be cited, for example, salts of alkyl sulfuric acid ester such as sodium laurylsulfate and amine salts of sulfuric acid ester of oleyl alcohol; alkyl sulfonate salts such as sodium dioctyl sulfosuccinate and sodium 2-ethylhexene sulfonate; arylsulfonate salts such as sodium isopropylnaphthalene sulfonate and sodium methylenebisnaphthalene sulfonate; and the like.

Furthermore, for the purpose of improvement of properties of formulae or enhancement of effects, the herbicides of the present invention may be used in combination with polymers and other auxiliary agents such as cassein, gelatin, albumin, glue, sodium alginate, carboxymethylcellulose, methylcellulose, hydroxyethylcellulose and poly(vinyl alcohol).

The above-described carriers or various auxiliary agents are used alone or in combination with others depending on the purposes taking into consideration, for example, forms of formulae or conditions of application.

The contents of active ingredients in the various formulae of the present invention thus prepared may vary widely depending on forms of formulae, and suitable content is within the range of usually from 0.1 to 99% by weight, and preferably from 1 to 80% by weight.

In the case of wettable powders, the formula contains active ingredient in the range from 20 to 90%, and the remainder solid carrier and dispersion wetting agent. If necessary, colloid protection agent or defoaming agent may added thereto.

In the case of granules, the formula contains active ingredient usually in the range from 1 to 35% by weight, and the remainder may be solid carrier and surfactant. The active ingredient may be mixed with solid carrier uniformly, or fixed to or adsorbed uniformly on the surface of solid carrier. The diameter of granules is in the range from 0.2 to 1.5 mm, and preferably in the range from 0.7 to 1.2 mm.

In the case of emulsifiable concentrates, the formula contains active ingredient usually in the range from 1 to 30% by weight, in addition emulsifier in the range from 5 to 20% by weight, and the remainder liquid carrier. If necessary, spreading agent and anticorrosive agent may be added thereto.

In the case of flowables, the formula contains active ingredient usually in the range from 5 to 50% by weight, in addition dispersion wetting agent in the range from 3 to 10% by weight, and the remainder being water. If necessary, protective colloid agent, preservative or defoaming agent may be added thereto.

The compounds of the present invention may be used as herbicides as they are or in any forms of formulae described above.

The dosage is generally, as amount of active ingredient, in the range from 1 to 10,000 g/ha, preferably in the range from 10 to 5,000 g/ha and more preferably in the range from 20 to 1000 g/ha. The application dosage may be varied properly depending for example on the species of targeting weeds and their growth stage, application site or weather.

The following non-limiting examples illustrate herbicidal compositions according to the present invention. The "part" in the following formulation means a portion by weight.

Formulation Example 1 (emulsifiable concentrate)

| | |
|---|---|
| Compound No. 2.333 | 20 parts |
| Xylene | 50 parts |
| Cyclohexane | 20 parts |
| Calcium dodecylbenzene sulfonate | 5 parts |
| Polyoxyethylenestyryl phenyl ether | 5 parts |

The above mixture was mixed and dissolved homogeneously to obtain 100 parts of emulsifiable concentrate.

Formulation Example 2 (wettable powder)

| | |
|---|---|
| Compound No. 4.99 | 20 parts |
| Clay | 70 parts |
| Calcium lignine sulfonate | 5 parts |
| Condensation product of naphthalenesulfonic acid and hormalin | 5 parts |

The above mixture was mixed and ground to obtain 100 parts of wettable powder formula.

Formulation Example 3 (granule formula)

| | |
|---|---|
| Compound No. 2.6 | 5 parts |
| Bentonite | 50 parts |
| Talc | 42 parts |
| Sodium lignosulfonate | 2 parts |
| Polyoxyethylene alkylaryl ether | 1 part |

The above mixture was mixed well, an appropriate amount of water added thereto, and granulated with a pushing-type granulator to obtain 100 parts of granule formula.

Formulation Example 4 (flowable formula)

| | |
|---|---|
| Compound No. 5.541 | 30 parts |
| Sodium di-(2-ethylhexyl)sulfosuccinate | 2 parts |
| Polyoxyethylene nonylphenyl ether | 2 parts |
| Defoaming agent | 1 part |
| Propylene glycol | 5 parts |
| Water | 60 parts |

The above mixture was mixed well, and pulverised uniformly using a wet ball mill to obtain 100 parts of flowable formula.

METHOD OF USE OF HERBICIDAL COMPOUNDS

Test Method 1 (Soil Application in Paddy Fields)

A suitable amount of water and chemical fertiliser were added to paddy field soil. A plastic pot (1/5000 a; 200 cm2) was filled with a portion of this soil followed by kneading to convert it to a state of a paddy field. A stock of paddy field rice plant (variety: Koshihikari) comprising a pair of two seedlings, which had been grown in advance in a greenhouse to the stage of two leaves, was transplanted into each pot. Furthermore, in each pot, there were sown predetermined amounts of seeds of *Echinochloa orizicola, Monochoria vaginalis* var. *plantaginea, Lindernia procunbens* and *Scirpus jundoides* var. *hotarui,* respectively, and water was added to a depth of 3 cm. On the next day a wettable powder formula was prepared by the method described in the Formulation Example 2, and diluted with a suitable amount of water to give a concentration of active ingredient of 1 kg per ha. The diluted formula was applied by dropping with a pipette.

After 28 days from the application with the chemicals, herbicidal effects on each weeds and phytotoxicity on paddy field rice plants were assessed according to the following criteria of Table 3. The results obtained are shown in Table 4.

TABLE 3

| | Criteria of assessment | |
|---|---|---|
| Point | Efficacy: % control | Phytotoxicity: % damage |
| 0 | 0 | 0 |
| 1 | 0–10 | 0–10 |
| 2 | 10–20 | 10–20 |
| 3 | 20–30 | 20–30 |
| 4 | 30–40 | 30–40 |
| 5 | 40–50 | 40–50 |
| 6 | 50–60 | 50–60 |
| 7 | 60–70 | 60–70 |
| 8 | 70–80 | 70–80 |
| 9 | 80–90 | 80–90 |
| 10 | 90–100 | 90–100 |

TABLE 4

| | | Application effects in paddy fields | | | | |
|---|---|---|---|---|---|---|
| No. of | Dose | Herbicidal efficacy (Point) | | | | Phytotoxicity |
| Compound | kg ai/ha | ECHOR | MOOVA | LIDPY | SCPJU | ORYSA |
| 1.73 | 1 | 10 | 10 | 7 | 9 | 2 |
| 1.313 | 1 | 10 | 10 | 10 | 10 | 3 |
| 2.6 | 1 | 10 | 10 | 8 | 7 | 3 |
| 2.129 | 1 | 10 | 10 | 9 | 8 | 2 |
| 2.135 | 1 | 4 | 9 | 0 | 4 | 0 |
| 2.619 | 1 | 10 | 10 | 10 | 9 | 3 |
| 4.61 | 1 | 10 | 9 | 10 | 9 | 1 |
| 4.68 | 1 | 10 | 10 | 8 | 6 | 3 |
| 4.71 | 1 | 10 | 10 | 9 | 9 | 3 |
| 4.99 | 1 | 9 | 10 | 8 | 5 | 3 |
| 4.107 | 1 | 10 | 10 | 5 | 9 | 1 |
| 5.146 Z isomer | 1 | 10 | 10 | 9 | 3 | 3 |
| 5.146 E isomer | 1 | 9 | 10 | 8 | 3 | 2 |
| 5.541 E isomer | 1 | 10 | 10 | 10 | 9 | 1 |

In Table 4 the following abbreviations are used:
ai: active ingredient
ECHOR: *Echinochloa oryzicola*
MOOVA: *Monochoria vaginalis*
LIDPY: *Lindemia procunbens*
SCPJU: *Scirpus juncoides*
ORYSA: *Oryza sativa*

TEST METHOD 2 a) General

Appropriate quantities of the compounds used to treat the plants were dissolved in acetone to give solutions equivalent to application rates of up to 250 g test compound per hectare (g/ha). These solutions were applied from an automatic laboratory herbicide sprayer delivering the equivalent of 720 liters of spray fluid per hectare.

b) Weed control: Pre-emergence

The seeds were sown in 70 mm square, 75 mm deep plastic pots in non-sterile soil, 3 species per pot. The quantities of seed per pot were as follows:

| | | Approx no. of seeds/species |
|---|---|---|
| Weed species | | |
| 1) | Broad-leafed weeds | |
| | *Abutilon theophrasti* | 7–8 |
| | *Amaranthus retroflexus* | 20 (pinch) |
| | *Galium aparine* | 4–5 |
| | *Ipomoea purpurea* | 5 |
| 2) | Grass weeds | |
| | *Alopecurus myosuroides* | 15–20 |
| | *Avena fatua* | 10 |
| | *Echinochloa crus-galli* | 15 |
| | *Setaria viridis* | 15 |
| Crop | | |
| 1) | Broad-leafed | |
| | Soya | 2 |
| 2) | Grass | |
| | Maize | 2 |
| | Rice | 5 |
| | Wheat | 5 |

The compounds of the invention were applied to the soil surface, containing the seeds, as described in (a). Pots containing the species represented were allocated to each treatment, with unsprayed controls and controls sprayed with acetone alone.

After treatment the pots were placed on capillary matting kept in a glass house, and watered overhead. Visual assessment of crop damage was made 17 days after spraying. The results were expressed as the percentage reduction in growth or damage to the crop or weeds, in comparison with the plants in the control pots.

When applied at 250 g/hectare or less pre- or post-emergence in Test Method 2, compounds 5.541, 4.107, 2.129, 4.71, 1.73, 2.619 and 1.313 of the invention gave at least 90% reduction in growth of one or more of the weed species listed above; at levels of applications toxic to the weeds these compounds were selective in at least one crop species.

What is claimed is:

1. A phenoxyacetic acid derivative of formula (I):

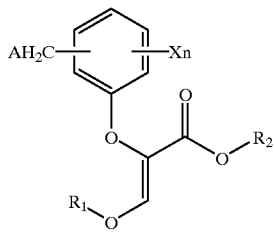

(I)

wherein $R_1$ and $R_2$ each represents independently a hydrogen atom, optionally substituted lower alkyl, optionally substituted lower alkenyl, optionally substituted lower alkynyl, optionally substituted cycloalkyl or —$C_mH_{2m}$ (optionally substituted phenyl);

X represents a halogen atom, cyano, lower alkoxycarbonyl, lower alkyl, lower alkenyl, lower alkynyl, cycloalkyl, lower alkoxy, lower alkylthio, lower alkylsulphinyl, lower alkylsulfonyl, lower haloalkoxycarbonyl, lower haloalkyl, lower haloalkenyl, lower haloalkynyl, halocycloalkyl, lower haloalkoxy, lower haloalkylthio, lower haloalkylsulphinyl, lower haloalkylsulfonyl, nitro, amino, lower alkylamino, lower dialkylamino, optionally substituted phenoxy, lower alkylcarbonylamino, carbamoyl, lower alkylcarbamoyl, lower dialkylcarbamoyl or $SF_5$;

n and m represent 0, 1 or 2;

A represents halogen atom, hydroxy, or A' wherein A' represents $OR_3$, $S(O)_kR_3$; or represents a formula II:

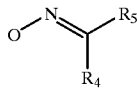

A-1

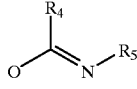

A-2

$R_3$ represents optionally substituted lower alkyl, optionally substituted lower alkenyl, optionally substituted lower alkynyl, optionally substituted cycloalkyl, optionally substituted phenyl, optionally substituted heteroaryl, optionally substituted lower alkylcarbonyl, optionally substituted lower alkenylcarbonyl, optionally substituted lower alkynylcarbonyl, optionally substituted cycloalkylcarbonyl, optionally substituted phenylcarbonyl, optionally substituted heteroarylcarbonyl, optionally substituted cycloalkenyl, optionally substituted cycloalkenylcarbonyl, —$C_pH_{2p}$ (optionally substituted phenyl), —$C_qH_{2q}$ (optionally substituted heteroaryl), —($C_rH_{2r}$) $CO_2$alkyl, —($C_sH_{2s}$)cycloalkyl, —CO ($C_tH_{2t}$)Y, —($C_uH_{2u}$) $COCH_2$ (optionally substituted phenyl), $C_fH_{2f}$ O (optionally substituted phenyl), —($C_gH_{2g}$) S (optionally substituted phenyl), or —($C_jH_{2j}$) O ($C_zH_{2z}$) (optionally substituted phenyl);

k represents zero, one or two;

f, g, j, z, p, q, r, s, t and u represent one or two;

Y represents optionally substituted phenyl, optionally substituted phenoxy, optionally substituted heteroaryl, optionally substituted phenylthio, alkoxy or optionally substituted heteroaryloxy;

$R_4$ represents a hydrogen atom, cyano, optionally substituted lower alkyl, optionally substituted lower alkenyl, optionally substituted lower alkynyl, optionally substituted cycloalkyl, optionally substituted phenyl, or optionally substituted heteroaryl;

$R_5$ represents optionally substituted lower alkyl, optionally substituted lower alkenyl, optionally substituted lower alkynyl, optionally substituted cycloalkyl, optionally substituted phenyl, optionally substituted lower alkoxy, optionally substituted lower alkenyloxy, optionally substituted lower alkynyloxy, optionally substituted cycloalkyloxy, optionally substituted heteroaryloxy, optionally substituted cycloalkenyloxy,, optionally substituted heteroaryl, —$C_vH_{2v}$ (optionally substituted phenyl), —$OC_wH_{2w}$ (optionally substituted phenyl), —($C_xH_{2x}$) O(optionally substituted phenyl), optionally substituted lower alkylthio, optionally substituted phenylthio, —$SC_yH_{2y}$ (optionally substituted phenyl) or optionally substituted phenoxy;

v, w, x and y represent one or two;

a geometric isomer thereof;

or an agriculturally acceptable salt thereof.

2. A phenoxyacetic acid derivative of formula (I) as defined in claim 1 in which:

$R_1$ and $R_2$ each represent independently a hydrogen atom, optionally substituted lower alkyl, optionally substituted lower alkenyl, optionally substituted lower alkynyl, or optionally substituted cycloalkyl;

X represents a halogen atom, cyano, lower alkoxycarbonyl, lower alkyl, lower alkenyl, lower alkynyl, cycloalkyl, lower alkoxy, lower alkylthio, lower alkylsulphinyl, lower alkylsulfonyl, lower haloalkoxycarbonyl, lower haloalkyl, lower haloalkenyl, lower haloalkynyl, halocycloalkyl, lower haloalkoxy, lower haloalkylthio, lower haloalkylsulphinyl, or lower haloalkylsulfonyl;

n represents 0, 1 or 2;

A represents halogen atom, or A' wherein A' means $OR_3$, $SR_3$, or the following general formula (A-1) or (A-2),

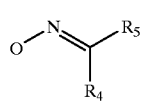
(A-1)

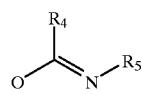
(A-2)

$R_3$ represents optionally substituted lower alkyl, optionally substituted lower alkenyl, optionally substituted lower alkynyl, optionally substituted lower cycloalkyl, optionally substituted phenyl, optionally substituted heteroaryl, optionally substituted lower alkylcarbonyl, optionally substituted lower alkenylcarbonyl, optionally substituted lower alkynylcarbonyl, optionally substituted lower cycloalkylcarbonyl, optionally substituted phenylcarbonyl, or optionally substituted heteroarylcarbonyl;

$R_4$ represents a hydrogen atom, cyano, optionally substituted lower alkyl, optionally substituted lower alkenyl, optionally substituted lower alkynyl, optionally substituted lower cycloalkyl, optionally substituted phenyl, or optionally substituted heteroaryl;

$R_5$ represents optionally substituted lower alkyl, optionally substituted lower alkenyl, optionally substituted lower alkynyl, optionally substituted lower cycloalkyl, optionally substituted phenyl group, optionally substituted lower alkoxy group, optionally substituted lower alkenyloxy, optionally substituted lower alkynyloxy, optionally substituted cycloalkyloxy, or optionally substituted heteroaryloxy.

3. A compound according to claim 1 in which the group $CH_2A$ is located at the ortho position of the phenyl ring.

4. A compound according to claim 1 in which $R_1$ and $R_2$ represent lower alkyl.

5. A compound according to claim 4 in which $R_1$ and $R_2$ represent methyl.

6. A compound according to claim 1 in which X represents halogen.

7. A compound according to claim 6 in which X represents chlorine.

8. A compound according to claim 1 in which A represents a group selected from halogen; hydroxy; A-1 wherein $R_4$ represents lower alkyl and $R_5$ represents $—OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl; A-2 wherein $R_4$ represents lower alkyl and $R_5$ represents $—OCH_2$ (optionally substituted phenyl); and $SR_3$ wherein $R_3$ represents optionally substituted phenyl, $CH_2$ (optionally substituted phenyl), lower alkyl or cycloalkyl.

9. A compound according to claim 8 in which A represents halogen or hydroxy.

10. A compound according to claim 1 in which:

$R_1$ and $R_2$ represent lower alkyl;

the group $CH_2A$ is located at the ortho position of the phenyl ring; and

A represents a group selected from halogen; hydroxy; A-1 wherein $R_4$ represents lower alkyl and $R_5$ represents $—OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl; A-2 wherein $R_4$ represents lower alkyl and $R_5$ represents $—OCH_2$ (optionally substituted phenyl); and $SR_3$ wherein $R_3$ represents optionally substituted phenyl, $—CH_2$ (optionally substituted phenyl), lower alkyl or cycloalkyl.

11. A compound according to claim 1 in which:

$R_1$ and $R_2$ represent lower alkyl;

X represents halogen; and $CH_2A$ is located at the ortho position of the phenyl ring and A represents a group selected from halogen; hydroxy; A-1 wherein $R_4$ represents lower alkyl and $R_5$ represents $—OC_wH_{2w}$ (optionally substituted phenyl), optionally substituted phenoxy or lower alkyl; $OR_3$ wherein $R_3$ represents optionally substituted phenyl, optionally substituted lower alkylcarbonyl or lower alkyl; A-2 wherein $R_4$ represents lower alkyl and $R_5$ represents $—OCH_2$ (optionally substituted phenyl); and $SR_3$ wherein $R_3$ represents optionally substituted phenyl, $CH_2$ (optionally substituted phenyl), lower alkyl or cycloalkyl.

12. A compound according to claim 1 in which:

$R_1$ and $R_2$ represent lower alkyl;

X represents halogen;

$CH_2A$ is located at the ortho position of the phenyl ring; and

A represents a group selected from halogen; hydroxy; A-1 wherein $R_4$ represents lower alkyl and $R_5$ represents $—OCH_2$ (optionally substituted phenyl), optionally substituted phenoxy or lower alkyl; $OR_3$ wherein $R_3$ represents optionally substituted phenyl, lower alkylcarbonyl or lower alkyl; and A-2 where $R_4$ represents lower alkyl and $R_5$ represents $—OCH_2$ (optionally substituted phenyl).

13. A herbicidal composition comprising an effective amount of a phenoxyacetic acid derivative according to claim 1 or an agriculturally acceptable salt thereof, in association with an agriculturally acceptable diluent or carrier and/or surface active agent.

14. A method for the control of weeds at a locus which comprises applying to said locus an effective amount of a phenoxyacetic acid derivative according to claim 1 or an agriculturally acceptable salt thereof, or a herbicidal composition according to claim 13.

15. A method according to claim 14 wherein the locus is an area used, or to be used for the growing of crops and the phenoxyacetic acid derivative is applied at an application rate of from 20 g to 1.0 kg/ha.

16. A process for the preparation of a phenoxyacetic acid derivative of formula (I) as defined in claim 1 which comprises:

(a) where formula (I) conforms to a formula (I-1):

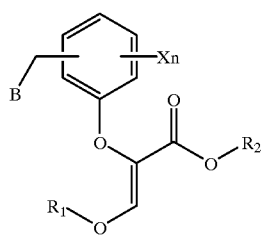

(I-1)

wherein B represents a halogen atom, the halogenation of the corresponding compound of formula (I) in which A is replaced by hydrogen, and $R_1$, $R_2$ and Xn are as defined in claim 1;

(b) where formula (I) conforms to a formula (I-2):

(I) conforms to a formula (I-2):

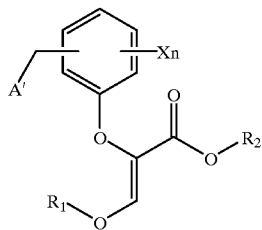

(I-2)

and A' represents $OR_3$, $SR_3$, A-1 or A-2 wherein $R_1$, $R_2$, A-1 and A-2 are as defined in claim 1, and $R_3$ represents optionally substituted lower alkyl, optionally substituted lower alkenyl, optionally substituted lower alkynyl, optionally substituted cycloalkyl, optionally substituted phenyl, optionally substituted heteroaryl, optionally substituted cycloalkenyl, —$C_pH_{2p}$ (optionally substituted phenyl), —$C_qH_{2q}$ (optionally substituted heteroaryl), —$(C_rH_{2r})$ $CO_2$alkyl, —$(C_sH_{2s})$ cycloalkyl, —$(C_uH_{2u})COCH_2$ (optionally substituted phenyl), —$(C_fH_{2f})$ O (optionally substituted phenyl), —$(C_gH_{2g})$ S(optionally substituted phenyl), or —$(C_jH_{2j})$ O $(C_zH_{2z})$ (optionally substituted phenyl); the alkylation of the corresponding compound of formula (I-1):

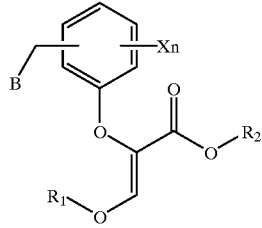

(I-1)

wherein B represents a halogen atom, with a compound of formula (IV):

A'H  (IV)

wherein A' is as defined in claim 1;

(c) where formula (I) represents the E-isomer conforming to formula (VI):

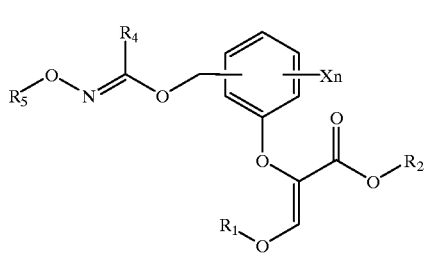

(VI)

wherein $R_1$, $R_2$, $R_4$, $R_5$ and Xn are as defined in claim 1, the isomerisation of the corresponding Z isomer conforming to formula (V):

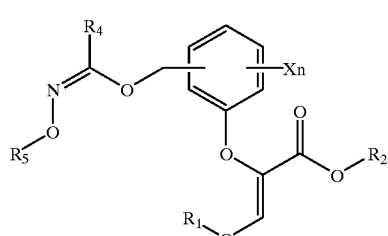

(V)

wherein $R_1$, $R_2$, $R_4$, $R_5$ and Xn are as defined in claim 1; where formula (I) represents a compound of formula (I-4):

a compound of formula (I-4):

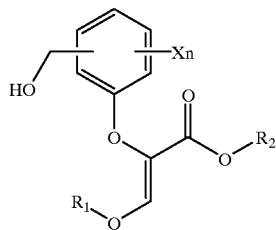

(I-4)

wherein $R_1$, $R_2$ and Xn are as defined in claim 1, the hydrolysis of the corresponding ester of formula (I-3):

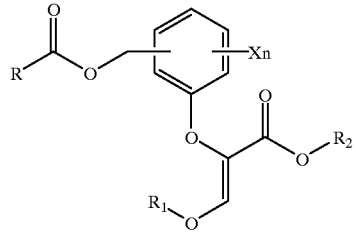

(I-3)

wherein R represents an alkyl group and $R_1$ $R_2$ and Xn are as defined in claim 1;

(e) where A represents $OR_3$ or $SR_3$, in which $R_3$ represents optionally substituted lower alkylcarbonyl, optionally substituted lower alkenylcarbonyl, optionally substituted lower alkynylcarbonyl, optionally substituted cycloalkylcarbonyl, optionally substituted phenylcarbonyl, optionally substituted heteroarylcarbonyl, optionally substituted cycloalkenylcarbonyl or —CO($C_rH_{2r}$) Y and Y is as defined in claim 1; the acylation of the corresponding compound of formula (I) wherein A represents OH or is replaced by SH, with an acid halide of formula (VII):

$$R_3COW \qquad (VII)$$

wherein W represents a halide; and (f) where A represents $S(O)_kR_3$ and k represents one or two, the oxidation of the corresponding compound of formula (I) in which k represents zero or one.

* * * * *